(12) United States Patent
Pettus et al.

(10) Patent No.: US 7,846,944 B2
(45) Date of Patent: Dec. 7, 2010

(54) PYRAZOLO-PYRIDINONE COMPOUNDS AND METHODS OF USE THEREOF

(75) Inventors: Liping Pettus, Thousand Oaks, CA (US); Andrew Tasker, Simi Valley, CA (US); Shimin Xu, San Diego, CA (US); Ryan Wurz, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 45 days.

(21) Appl. No.: 12/151,478

(22) Filed: May 6, 2008

(65) Prior Publication Data

US 2009/0012299 A1 Jan. 8, 2009

Related U.S. Application Data

(60) Provisional application No. 60/928,155, filed on May 7, 2007, provisional application No. 61/066,424, filed on Feb. 19, 2008, provisional application No. 61/043,089, filed on Apr. 7, 2008.

(51) Int. Cl.
*C07D 487/04* (2006.01)
*A01N 43/42* (2006.01)
*A61K 31/44* (2006.01)

(52) U.S. Cl. ...................... 514/303; 546/119
(58) Field of Classification Search ................. 546/119; 514/303
See application file for complete search history.

(56) References Cited

U.S. PATENT DOCUMENTS

| 6,635,644 B2 | 10/2003 | Salituro | |
| 2005/0026946 A1* | 2/2005 | Wager | ......................... 514/303 |
| 2006/0035897 A1 | 2/2006 | Caravatti | |

FOREIGN PATENT DOCUMENTS

| WO | 2004010995 A1 | 2/2004 |
| WO | 2007089634 | * 8/2007 |

OTHER PUBLICATIONS

Rivkin et al., Tetrahedron Letters (2006), 47(14), 2395-2398.*
Schmidt et al., Helvetica Chimica Acta (1962), 45, 1620-7.*
Shohami et al., J. Cereb. Blood Flow Metab. 14:615 (1994).
Feurstein et al., Neurosci. Lett. 164:125 (1993).
Feurstein, Stroke 25:1481 (1994).
Clouse et al., J. Immunol. 142:431 (1989).
Lahdevirta et al., (Am. J. Med. 85:289 (1988).
Abraham, Lancet, 351:929 (1998).
Couriel, Curr. Opinion Oncology, 12:582 (2000).
Labiache, Rheumatology, 43:531 (2004).
Ruan, Cytokine GF Review, 14:447 (2003).
Roberts, Chest, 124:2028 (2003).
Wget, New England J. Med., 352:351 (2005).
Sugano et al, Mol. Cell Bioch., 266:127 (2004).
Chandrasekhar et al., Clinical Immunol Immunopathol., 55:382 (1990).
Firestein, Am. J. Pathol., 140:1309 (1992).
Dinarello, Eur. Cytokine Netw., 5:517-531 (1994).
Folks et al., J. Immunol., 136:40 (1986).
Beutler et al. (J. Immunol., 135:3969 (1985).
Baracos et al. (New Eng. J. Med., 308:553 (1983).
Brahn et al., Lymphokine Cytokine Res. 11:253 (1992).
Cooper, Clin. Exp. Immunol., 898:244 (1992).
Feldmann et al., Immunological Reviews, pp. 195-223 (1995).
Berge et al., J. Pharm. Sci., 66, 1 (1977).
J. Org. Chem. 2005, 70, pp. 5721-5724.
C. A. Winter et al., Proc. Soc. Exp. Biol. Med., 111:544 (1962).
D. E. Trentham et al., J. Exp. Med., 146:857 (1977).
J. S. Courtenay, Nature (New Biol.), 283:666 (1980).

* cited by examiner

*Primary Examiner*—D. Margaret Seaman
*Assistant Examiner*—Niloofar Rahmani
(74) *Attorney, Agent, or Firm*—G. Prabhakar Reddy

(57) ABSTRACT

The present invention comprises a new class of compounds useful for the prophylaxis and treatment of protein kinase mediated diseases, including inflammation and related conditions. The compounds have a general Formula I

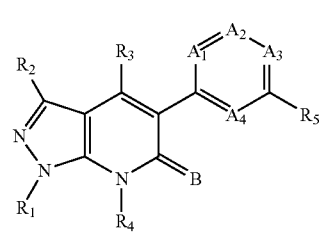

wherein $A^1$, $A^2$, $A^3$, $A^4$, B, $R^1$, $R^2$, $R^3$, $R^4$ and $R^5$ are defined herein. The invention also comprises pharmaceutical compositions including one or more compounds of Formula I, uses of such compounds and compositions for treatment of P38 map kinase mediated diseases including rheumatoid arthritis, psoriasis, chronic obstructive pulmonary disease, pain and other inflammatory disorders, as well as intermediates and processes useful for the preparation of compounds of Formula I.

18 Claims, No Drawings

PYRAZOLO-PYRIDINONE COMPOUNDS AND METHODS OF USE THEREOF

This application claims the benefit of U.S. Provisional Application No. 60/928,155, filed May 7, 2007, U.S. Provisional Application No. 61/066,424, filed Feb. 19, 2008 and U.S. Provisional Application No. 61/043,089, filed Apr. 7, 2008 which are hereby incorporated by reference.

FIELD OF THE INVENTION

The invention relates generally to the field of pharmaceutical agents and, more specifically, to pharmaceutically active compounds, pharmaceutical compositions and methods of use thereof, to treat various disorders, including TNF-α, IL-1β, IL-6 and/or IL-8 mediated diseases and other maladies, such as inflammation and pain. The invention also relates to intermediates and processes useful in the preparation of such compounds.

BACKGROUND OF THE INVENTION

Protein kinases represent a large family of enzymes, which catalyze the phosphorylation of target protein substrates. The phosphorylation is a transfer reaction of a phosphate group from ATP to the protein substrate. Common points of attachment for the phosphate group to the protein substrate include, for example, a tyrosine, serine or threonine residue. Protein tyrosine kinases (PTKs) are enzymes, which catalyze the phosphorylation of specific tyrosine residues in cellular proteins. Examples of kinases in the protein kinase family include, without limitation, abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRafl, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Due to their activity in numerous cellular processes, protein kinases have emerged as important therapeutic targets.

Protein kinases play a central role in the regulation and maintenance of a wide variety of cellular processes and cellular function. For example, kinase activity acts as molecular switches regulating inflammatory cytokine production via various pathways. Uncontrolled or excessive cytokine production has been observed in many disease states, and particularly in those related to inflammation.

The p38 protein kinase has been reported to be involved in the regulation of inflammatory cytokines. Interleukin-1 (IL-1) and Tumor Necrosis Factor α (also referred to herein as TNF-α or TNF) are pro-inflammatory cytokines secreted by a variety of cells, including monocytes and macrophages, in response to many inflammatory stimuli (e.g., lipopolysaccharide (LPS)) or external cellular stress (e.g., osmotic shock and peroxide).

Elevated levels of TNF-α over basal levels have been implicated in mediating or exacerbating a number of disease states including rheumatoid arthritis (RA); osteoarthritis; rheumatoid spondylitis; gouty arthritis; inflammatory bowel disease (IBD); adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

TNF-α has been reported to play a role in head trauma, stroke, and ischemia. For instance, in animal models of head trauma (rat), TNF-α levels increased in the contused hemisphere (Shohami et al., J. Cereb. Blood Flow Metab. 14:615 (1994)). In a rat model of ischemia wherein the middle cerebral artery was occluded, the levels of TNF-α mRNA of TNF-α increased (Feurstein et al., Neurosci. Lett., 164:125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area-(Feurstein, Stroke 25:1481 (1994)).

TNF-α appears to play a role in promoting certain viral life cycles and disease states associated therewith. For instance, TNF-α secreted by monocytes induced elevated levels of HIV expression in a chronically infected T cell clone (Clouse et al., J. Immunol. 142:431 (1989)). Lahdevirta et al., (Am. J. Med. 85:289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8. Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

Antagonism of TNF-α has been reported to be beneficial for treating uveitis (Reiff et al, A&R 44:141-145 (2001)); Sepsis (Abraham, Lancet, 351:929 (1998)); Systemic Lupus Erythrematosis (SLE) (Aringer, A&R, 50:3161 (2004)); Graft vs Host Disease (Couriel, Curr. Opinion Oncology, 12:582 (2000)); Polymyositis and Dermatomyositis (Labiache, Rheumatology, 43:531 (2004)); Type II diabetes (Ruan, Cytokine GF Review, 14:447 (2003)); Sjogren's disease (Marriette, A&R, 50:1270 (2004)), Sarcoidosis (Roberts, Chest, 124:2028 (2003)); Wegener's granulomatosis (WGET, New England J. Med., 352:351 (2005)) and post MI cardiac dysfunction (Sugano et al, Mol. Cell. Bioch., 266:127 (2004)). In addition, TNF-α has been reported to play a role in SAPHO, periodic fever, relapsing polychrondritis, multicentric reticulohistiocytosis, macrophage activation syndrome, Hyper IgD syndrome, familial Hibernian fever, Pyoderma gangrenosum, Cochleovestibular disorders, Cicatrical pemphigoid, Herniated intervertebral disc diseases, amyloidosis, CINCA syndrome, myelodisplastic syndrome, alcoholic hepatitis, and endometriosis. Finally, indications which have already been approved for treatment with a therapeutic agent which modulates TNF-α levels in the plasma, and/or other pro-inflammatory cytokines, include without limitation, inflammatory bowel disease (IBD), psoriatis arthritis, ankylosing spondylitis and juvenile RA.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus, glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production. Elevation of glucose levels along with the reduced expression of IL-1Ra, an antagonist of IL-1 signaling, leads to impaired insulin secretion, decreased cell proliferation and apoptosis. Inhibiton of IL-1 action has been shown to improve glycemia, b-cell secretory function and reduce markers of systemic inflammation (Larsen, New England J. Med., 356: 1517 (2007).

In rheumatoid arthritis models in animals, multiple intra-articular injections of IL-1 led to an acute and destructive form of arthritis (Chandrasekhar et al., Clinical Immunol Immunopathol., 55:382 (1990)). In studies using cultured rheumatoid synovial cells, IL-1 is a more potent inducer of stromelysin than is TNF-$\alpha$ (Firestein, Am. J. Pathol., 140: 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, Eur. Cytokine Netw., 5:517-531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., J. Immunol., 136:40 (1986)). Beutler et al. (J. Immunol., 135:3969 (1985)) discussed the role of IL-1 in cachexia. Baracos et al. (New Eng. J. Med., 308:553 (1983)) discussed the role of IL-1 in muscle degeneration.

In rheumatoid arthritis (RA), both IL-1 and TNF-$\alpha$ induce synoviocytes and chondrocytes to produce collagenase and neutral proteases, which leads to tissue destruction within the arthritic joints. In an in-vivo animal model of arthritis, i.e., collagen-induced arthritis (CIA) in rats and mice, intra-articular administration of TNF-$\alpha$ either prior to or after the induction of CIA led to an accelerated onset of arthritis and a more severe course of the disease (Brahn et al., Lymphokine Cytokine Res. 11:253 (1992); and Cooper, Clin. Exp. Immunol., 898:244 (1992)). IL-1 and TNF-$\alpha$ have been implicated in pro-inflammatory mechanisms in many human diseases including inflammatory arthritis, inflammatory bowel disease sepsis syndrome and both acute and cheonis inflammation of many organs. (Vassali P., The Pathophysiology of Tumor Necrosis Factors, Ann. Rev. Immunology 10: 411-452 (1992) and Dinarello Calif., Biologic Basis for Interluekin-1 in disease, Blood, 87:2095-2147 (1996)).

IL-6 also appears to play a role in, and therefore have applications to, pro-inflammatory and other malignant diseases. Particularly, deregulated levels of IL-6 are associated with various immunological diseases, such as RA, systemic juvenile idiopathic arthritis (sJIA), polyarticular type JIA, systemic lupus erythematosus (SLE), vasculitis syndrome, Castleman Disease and Crohn's Disease; transplantation conditions such as acute rejection and graft-versus-host disease (GVHD); respiratory diseases such as interstitial pneumonia and bronchial; asthma; bone diseases such as osteoporosis and Paget's disease, as well as various malignant disease including multiple myeloma, renal cancer, prostate cancer, cardiac mixoma, Kaposis sarcoma, Mesothelioma, Malignant lymphoma, lung cancer and gastric cancer. (Nishimoto and Kishimoto, Review, 2: 619-625 (2006)). It follows that the reduction and/or regulation of IL-6 levels may be useful for treatment of one or more of the above diseases.

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

The role and activity of the p38 protein in RA and other pro-inflammatory cytokine mediated diseases and conditions are becoming better understood. For example, Korb et al., Arthritis and Rheumatism, 54: 2745-2756 (2006) describes the activation of the p38 alpha (p38$\alpha$) and p38 gamma (p38$\gamma$) and the role which these two isoforms play in the development and progression of RA. Korb further describes the correlation between expression of p38 and the incidence of CRP in RA. Korb has found that the expression of these isoforms dominate in patients with chronic inflammation and, therefore, concludes that effective strategies to inhibit p38 kinase should aim to specifically target either or both of the isoforms. Medicherla et al., J. Pharmacology and Experimental Therapeutics, 318, 132-141 (2006) and Nishikawa et al., Arthritis & Rheumatism, 48, 2670-2681 (2003) describe results of an in-vivo collegan-induced arthritis (CIA) model in the rat and mouse. More specifically, they report that, in both animals, inhibition of p38$\alpha$ activity and related signaling improved clinical score and reversed bone and cartilage destruction. Ferrari, Cardiovascular Research 37:554 (1998) and Jacobsson et al., J Rheum. 32:1213 (2005) describe how pro-inflammatory cytokines, such as TNF and IL-1, play a role in cadiovascular disease. More specifically, they have found that blocking or reducing the levels of TNF-$\alpha$ have a protective effect, and reduce the incidence of cardiovascular disease in RA patients. Behr et al., Circulation, 104, 1292 (2001) describes the ability and efficacy of a p38 kinase inhibitor in treating hypertensive cardiac hypertrophy.

Several approaches have been taken to block the effect of TNF-$\alpha$. One approach involves using soluble receptors for TNF-$\alpha$ (e.g., TNFR-55 or TNFR-75), which have demonstrated efficacy in animal models of TNF-$\alpha$-mediated disease states. A second approach to neutralizing TNF-$\alpha$ using a monoclonal antibody specific to TNF-$\alpha$, cA2, has demonstrated improvement in swollen joint count in a Phase II human trial of rheumatoid arthritis (Feldmann et al., *Immunological Reviews*, pp. 195-223-(1995)). These approaches block the effects of TNF-$\alpha$ and IL-1 by either protein sequestration or receptor antagonism.

Yet another approach to block the effect of TNF-$\alpha$, and other pro-inflammatory cytokines, has been to modulate the activity of the p38 kinase enzyme. For example, the PCT publication, WO 04/010995, published on Feb. 5, 2004, describes fused heteroaryl derivatives for use as p38 kinase inhibitors in the treatment of I.A. and rheumatoid arthritis; PCT publication, WO 2005/009937, published on Feb. 3, 2005, describes 5-membered heterocycle-based p38 kinase inhibitors; U.S. Pat. No. 6,635,644, issued Oct. 21, 2003, describes fused nitrogen-containing bicyclic ring systems as p38 inhibitors; and U.S. Pat. No. 6,794,380, issued Sep. 21, 2004, describes amide derivatives as p38 inhibitors. Despite the ongoing efforts, there needs to be effective anti-inflammatory agents which regulate the production of pro-inflammatory cytokines, including TNF-α, IL-1β, IL-6 and/or IL-8.

BRIEF DESCRIPTION OF THE INVENTION

The present invention provides a new class of compounds useful in the prophylaxis and treatment of diseases mediated by pro-inflammatory cytokines, such as TNF-α, IL-1β, IL-6 and/or IL-8. The compounds, including stereoisomers, tautomers, solvates, pharmaceutically acceptable salts, derivatives or prodrugs thereof, are generally defined by Formula I

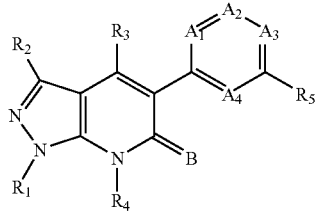

I wherein $A^1$, $A^2$, $A^3$, $A^4$, B, $R^1$, $R^2$, $R^3$, $R^4$ and $R^5$ are as described below. The invention also provides procedures for making compounds of Formula I, compounds of Formula II, and intermediates useful in such procedures.

The compounds provided by the invention are capable of modulating the p38 kinase protein. To this end, the compounds of the invention are useful for regulating the levels of pro-inflammatory cyclokines and for therapeutic, prophylactic, acute and/or chronic treatment of TNF-α, IL-1β, IL-6 and/or IL-8 mediated diseases, such as those described herein. For example, the compounds are useful for the prophylaxis and treatment of RA, pain, and other conditions involving inflammation. In another embodiment, the invention provides pharmaceutical compositions, also commonly referred to as "medicaments", comprising one or more of the compounds of the invention in combination with one or more pharmaceutically acceptable carrier(s) or excipient(s). Such pharmaceutical compositions are useful to attenuate, alleviate, or treat p38 kinase-mediated disorders through inhibition of the activity of the p38 kinase enzyme.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are defined by general Formula I:

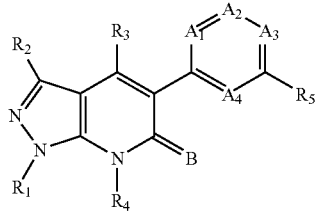

I wherein
each of $A^1$, $A^2$, $A^1$ and $A^4$, independently, is $CR^6$ or N, provided that no more than two of $A^1$, $A^2$, $A^3$ and $A^4$ is N;
B is O, S or N—CN;
$R^1$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$,
or $R^1$ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^9$;
each of $R^2$ and $R^3$, independently, is H, halo, haloalkyl, $NO_2$, CN, $OR^7$, $SR^7$, $NR^7R^7$, $NR^7R^8$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$;
$R^4$ is CN, $C(O)R^7$, $C_{1-10}$-alkyl, $C_{2-10}$-alkenyl, $C_{2-10}$-alkynyl or $C_{3-8}$-cycloalkyl, each of the $C_{1-10}$-alkyl, $C_{2-10}$-alkenyl, $C_{2-10}$-alkynyl and $C_{3-8}$-cycloalkyl optionally comprising 1-4 heteroatoms selected from N, O and S and optionally substituted with one or more substituents of $R^9$;
$R^5$ is $R^7$, $NR^7R^7$, $NR^7R^8$, $R^7SR^7$, $OR^8$, $SR^8$, $C(O)R^7$, $C(NCN)R^7$, $C(O)R^8$, $C(NCN)R^8$, $C(O)C(O)R^7$, $OC(O)R^7$, $COOR^8$, $C(O)C(O)R^8$, $OC(O)R^8$, $COOR^8$, $C(O)NR^7R^7$, $C(O)NR^7R^8$, $OC(O)NR^7R^8$, $NR^7C(O)R^7$, $NR^7C(O)R^8$, $NR^7C(O)NR^7R^7$, $NR^7C(O)NR^7R^8$, $NR^7(COOR^7)$, $NR^7(COOR^8)$, $S(O)_2R^7$, $S(O)_2R^8$, $S(O)NR^7R^7$, $S(O)_2NR^7R^8$, $NR^7S(O)_2NR^7R^8$, $NR^7S(O)R^7$ or $NR^7S(O)_2R^8$;
each $R^6$, independently, is H, halo, haloalkyl, $NO_2$, CN, $OR^1$, $NR^7R^7$ or $C_{1-10}$-alkyl, the $C_{1-10}$-alkyl optionally comprising 1-4 heteroatoms selected from N, O and S and optionally substituted with one or more substituents of $R^9$;
each $R^7$, independently, is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^9$, $COOR^9$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;
$R^8$ is a partially or fully saturated or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;
alternatively, $R^7$ and $R^8$ taken together form a saturated or partially or fully unsaturated 0.5-6 membered monocyclic or 7-10 membered bicyclic ring of carbon atoms optionally including 1-3 heteroatoms selected from O, N, or S, and the ring optionally substituted independently with 1-5 substituents of $R^9$; and $R^9$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In another embodiment, the compounds of Formula I include compounds wherein $A^1$ is $CR^6$, in conjunction with any of the above or below embodiments.

In another embodiment, the compounds of Formula I include compounds wherein $A^2$ is $CR^6$, in conjunction with any of the above or below embodiments.

In another embodiment, the compounds of Formula I include compounds wherein $A^3$ is $CR^6$, in conjunction with any of the above or below embodiments.

In another embodiment, the compounds of Formula I include compounds wherein $A^4$ is $CR^6$, in conjunction with any of the above or below embodiments.

In another embodiment, the compounds of Formula I include compounds wherein $A^1$ is N, in conjunction with any of the above or below embodiments.

In another embodiment, the compounds of Formula I include compounds wherein $A^2$ is N, in conjunction with any of the above or below embodiments.

In another embodiment, the compounds of Formula I include compounds wherein $A^3$ is N, in conjunction with any of the above or below embodiments.

In another embodiment, the compounds of Formula I include compounds wherein $A^4$ is N, in conjunction with any of the above or below embodiments.

In another embodiment, the compounds of Formula I include compounds wherein each of $A^1$, $A^2$, $A^3$ and $A^4$, independently, as $CR^6$, in conjunction with any of the above or below embodiments.

In another embodiment, the compounds of Formula I include compounds wherein three of $A^1$, $A^2$, $A^3$ and $A^4$, independently, is $CR^6$ and the other one of $A^1$, $A^2$, $A^3$ and $A^4$, independently, as N, in conjunction with any of the above or below embodiments.

In another embodiment, the compounds of Formula I include compounds wherein two of $A^1$, $A^2$, $A^3$ and $A^4$, independently, is $CR^6$ and the other two of $A^1$, $A^2$, $A^3$ and $A^4$, independently, as N, in conjunction with any of the above or below embodiments.

In another embodiment, the compounds of Formula I include compounds wherein two of $A^1$, $A^2$, $A^3$ and $A^4$, independently, is $CR^6$ and the other two of $A^1$, $A^2$, $A^1$ and $A^4$, independently, as CH, in conjunction with any of the above or below embodiments.

In another embodiment, the compounds of Formula I include compounds wherein each of $A^1$ and $A^2$, independently, is $CR^6$ and each of $A^3$ and $A^4$, independently, is CH, in conjunction with any of the above or below embodiments.

In another embodiment, the compounds of Formula I include compounds wherein each of $A^1$ and $A^2$, independently, is $CR^6$ wherein each $R^6$, independently, is H, F, Cl, Br, $CF_3$, —$OCF_3$, $C_2F_5$, —$OC_2F_5$, —O—$C_{1-6}$-alkyl, —$C_{1-4}$-alkyl-O—$C_{1-6}$-alkyl, —S—$C_{1-6}$-alkyl, —$C_{1-4}$-alkyl-S—$C_{1-6}$-alkyl, —NH—$C_{1-6}$-alkyl, —N($C_{1-6}$-alkyl)$_2$, —$C_{1-4}$-alkyl-NH—$C_{1-6}$-alkyl, —$C_{1-3}$-alkyl-N ($C_{1-4}$-alkyl)$_2$, $NO_2$, $NH_2$, CN or $C_{1-10}$-alkyl, and each of $A^3$ and $A^4$, independently, is CH, in conjunction with any of the above or below embodiments.

In another embodiment, the compounds of Formula I include compounds wherein each of $A^1$ and $A^2$, independently, is $CR^6$ wherein each $R^6$, independently, is H, F, Cl, Br, $CF_3$, —$OCF_3$, $C_2F_5$, —$OC_2F_5$, —O—$C_{1-4}$-alkyl, —S—$C_{1-4}$-alkyl, —NH—$C_{1-4}$-alkyl, OH, $NO_2$, $NH_2$, CN, methyl, ethyl or propyl, and each of $A^3$ and $A^4$, independently, is CH, in conjunction with any of the above or below embodiments.

In another embodiment, the compounds of Formula I include compounds wherein each of $A^1$, $A^2$, $A^3$ and $A^4$, independently, is $CR^6$ and each $R^6$, independently, is H, F, Cl, Br, $CF_3$, —$OCF_3$, $C_2F_5$, —$OC_2F_5$, —O—$C_{1-6}$-alkyl, —$C_{1-4}$-alkyl-O—$C_{1-6}$-alkyl, —S—$C_{1-6}$-alkyl, —$C_{1-4}$-alkyl-S—$C_{1-6}$-alkyl, —NH—$C_{1-6}$-alkyl, —N($C_{1-6}$-alkyl)$_2$, —$C_{1-4}$-alkyl-NH—$C_{1-6}$-alkyl, —$C_{1-3}$-alkyl-N ($C_{1-4}$-alkyl)$_2$, $NO_2$, $NH_2$, CN or $C_{1-10}$-alkyl, in conjunction with any of the above or below embodiments.

In another embodiment, the compounds of Formula I include compounds wherein each of $A^1$, $A^2$, $A^3$ and $A^4$, independently, is $CR^6$ wherein each $R^6$, independently, is H, F, Cl, Br, $CF_3$, —$OCF_3$, $C_2F_5$, —$OC_2F_5$, —O—$C_{1-6}$-alkyl, —$C_{1-4}$-alkyl-O—$C_{1-6}$-alkyl, —S—$C_{1-6}$-alkyl, —$C_{1-4}$-alkyl-S—$C_{1-6}$-alkyl, —NH—$C_{1-6}$-alkyl, —N($C_{1-6}$-alkyl)$_2$, —$C_{1-4}$-alkyl-NH—$C_{1-6}$-alkyl, —$C_{1-3}$-alkyl-N($C_{1-4}$-alkyl)$_2$, $NO_2$, $NH_2$, CN, $C_{1-10}$-alkyl, the $C_{1-10}$-alkyl optionally substituted with one or more substituents of $R^9$; and each of $R^2$ and $A^3$, independently, is H or halo, in conjunction with any of the above or below embodiments.

In another embodiment, related to the immediately preceeding embodiments, the compounds of Formula I include compounds wherein each $R^6$, independently, is H, halo, haloalkyl, $NO_2$, CN, $OR^7$, $NR^7R^7$ or $C_{1-10}$-alkyl, the $C_{1-10}$-alkyl optionally comprising 1-4 heteroatoms selected from N, O and S and optionally substituted with one or more substituents of $R^9$, in conjunction with any of the above or below embodiments.

In another embodiment, related to the immediately preceeding embodiments, Formula I includes compounds wherein each $R^6$, independently, is H, F, Cl, Br, $CF_3$, —$OCF_3$, $C_2F_5$, —$OC_2F_5$, —O—$C_{1-4}$-alkyl, —$C_{1-4}$-alkyl-O—$C_{1-6}$-alkyl, —S—$C_{1-6}$-alkyl, —$C_{1-4}$-alkyl-S—$C_{1-6}$-alkyl, —NH—$C_{1-4}$-alkyl, —N($C_{1-6}$-alkyl)$_2$, —$C_{1-4}$-alkyl-NH—$C_{1-4}$-alkyl, —$C_{1-3}$-alkyl-N($C_{1-4}$-alkyl)$_2$, $NO_2$, $NH_2$, CN, $C_{1-10}$-alkyl or the $C_{1-10}$-alkyl optionally substituted with one or more substituents of $R^9$, in conjunction with any of the above or below embodiments.

In another embodiment, the compounds of Formula I include compounds wherein one of $A^1$, $A^2$, $A^3$ and $A^4$, independently, is N and the remaining of $A^1$, $A^2$, $A^3$ and $A^4$, independently, is $CR^6$ wherein each $R^6$, independently, is H, F, Cl, Br, $CF_3$, —$OCF_3$, $C_2F_5$, —$OC_2F_5$, —O—$C_{1-6}$-alkyl, —$C_{1-4}$-alkyl-O—$C_{1-6}$-alkyl, —S—$C_{1-6}$-alkyl, —$C_{1-4}$-alkyl-S—$C_{1-6}$-alkyl, —NH—$C_{1-6}$-alkyl, —N($C_{1-6}$-alkyl)$_2$, —$C_{1-4}$-alkyl-NH—$C_{1-6}$-alkyl, —$C_{1-3}$-alkyl-N($C_{1-4}$-alkyl)$_2$, $NO_2$, $NH_2$, CN, $C_{1-10}$-alkyl, the $C_{1-10}$-alkyl optionally substituted with one or more substituents of $R^9$, in conjunction with any of the above or below embodiments.

In another embodiment, the compounds of Formulas I include compounds wherein B is O, S or N—CN, in conjunction with any of the above or below embodiments.

In another embodiment, the compounds of Formulas I include compounds wherein B is O, in conjunction with any of the above or below embodiments.

In another embodiment, the compounds of Formulas I include compounds wherein B is S, in conjunction with any of the above or below embodiments.

In another embodiment, the compounds of Formulas I include compounds wherein B is N—CN, in conjunction with any of the above or below embodiments.

In another embodiment, the compounds of Formulas I include compounds wherein B is O or S, in conjunction with any of the above or below embodiments.

In another embodiment, the compounds of Formula I includes compounds wherein $R^1$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$, in conjunction with any of the above or below embodiments.

In another embodiment, the compounds of Formula I includes compounds wherein $R^1$ is $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$, in conjunction with any of the above or below embodiments.

In another embodiment, the compounds of Formula I includes compounds wherein $R^1$ is methyl, ethyl, propyl, isopropyl, butyl, isobutyl, sec-butyl, pentyl, neopenyl, hexyl, cyclopropyl, cyclopentyl, cyclohexyl or alkyl, each of which is optionally comprising 1-4 heteroatoms selected from N, O and S and optionally substituted with one or more substituents of $R^9$, in conjunction with any of the above or below embodiments.

In another embodiment, the compounds of Formula I includes compounds wherein $R^1$ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^9$, in conjunction with any of the above or below embodiments.

In another embodiment, the compounds of Formula I includes compounds wherein $R^1$ is phenyl, naphthyl, pyridyl, pyrimidyl, triazinyl, quinolinyl, isoquinolinyl, quinazolinyl, isoquinazolinyl, thiophenyl, furyl, tetrahydrofuryl, pyrrolyl, tetrahydropyrrolyl, pyrazolyl, imidazolyl, triazolyl, tetrazolyl, thiazolyl, oxazolyl, oxazolinyl, isoxazolyl, isoxazolinyl, oxadiazolyl, isothiazolyl, indolyl, indolinyl, isoindolyl, benzofuranyl, dihydrobenzofuranyl, benzothiophenyl, benzisoxazolyl, benzopyrazolyl, benzothiazolyl, benzimidazolyl, piperidinyl, pyranyl, cyclopropyl, cyclobutyl or cyclohexyl, each of which is optionally substituted independently with one or more substituents of $R^9$, in conjunction with any of the above or below embodiments.

In another embodiment, the compounds of Formula I includes compounds wherein $R^1$ is phenyl, pyridyl, pyrimidyl, triazinyl, pyridazinyl, pyrazinyl, thiophenyl, furyl, tetrahydrofuryl, pyrrolyl, tetrahydropyrrolyl, pyrazolyl, imidazolyl, triazolyl, tetrazolyl, thiazolyl, oxazolyl, oxazolinyl, isoxazolyl, isoxazolinyl, oxadiazolyl, isothiazolyl, piperidinyl, pyranyl, cyclopropyl, cyclobutyl or cyclohexyl, each of which is optionally substituted independently with one or more substituents of $R^9$, in conjunction with any of the above or below embodiments.

In another embodiment, the compounds of Formula I includes compounds wherein $R^1$ is phenyl, pyridyl, pyrimidyl, pyridazinyl, pyrazinyl, thiophenyl, furyl, pyrrolyl, pyrazolyl, imidazolyl, triazolyl, thiazolyl, oxazolyl, isoxazolyl, oxadiazolyl or isothiazolyl, each of which is optionally substituted independently with one or more substituents of $R^9$, in conjunction with any of the above or below embodiments.

In another embodiment, the compounds of Formula I includes compounds wherein $R^1$ is phenyl, pyridyl, pyrimidyl, pyridazinyl or pyrazinyl, each of which is optionally substituted independently with one or more substituents of $R^9$, in conjunction with any of the above or below embodiments.

In another embodiment, the compounds of Formula I includes compounds wherein $R^1$ is piperidinyl, pyranyl, cyclopropyl, cyclobutyl or cyclohexyl, each of which is optionally substituted independently with one or more substituents of $R^9$, in conjunction with any of the above or below embodiments.

In another embodiment, the compounds of Formula I includes compounds wherein $R^1$ is phenyl or pyridyl, each of which is optionally substituted independently with one or more substituents of $R^9$, in conjunction with any of the above or below embodiments.

In another embodiment, the compounds of Formula I includes compounds wherein $R^1$ is phenyl, optionally substituted independently with one or more substituents of $R^9$, in conjunction with any of the above or below embodiments.

In another embodiment, the compounds of Formula I includes compounds wherein $R^1$ is thiophenyl, furyl, pyrrolyl, pyrazolyl, imidazolyl, triazolyl, thiazolyl, oxazolyl, isoxazolyl, oxadiazolyl or isothiazolyl, each of which is optionally substituted independently with one or more substituents of $R^9$, in conjunction with any of the above or below embodiments.

In another embodiment, the compounds of Formula I includes compounds wherein $R^2$ is H, halo, haloalkyl, $NO_2$, CN, $OR^7$, $SR^7$, $NR^7R^7$, $NR^7R^8$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$, in conjunction with any of the above or below embodiments.

In another embodiment, the compounds of Formula I includes compounds wherein $R^2$ is H, halo, haloalkyl, $NO_2$, CN, $OR^7$, $NR^7R^7$ or $C_{1-10}$-alkyl, in conjunction with any of the above or below embodiments.

In another embodiment, the compounds of Formula I includes compounds wherein $R^2$ is H, halo, haloalkyl or $C_{1-10}$-alkyl, in conjunction with any of the above or below embodiments.

In another embodiment, the compounds of Formula I includes compounds wherein $R^2$ is H, halo, methyl or ethyl, in conjunction with any of the above or below embodiments.

In another embodiment, the compounds of Formula I includes compounds wherein $R^2$ is H, F, Cl, methyl or ethyl, in conjunction with any of the above or below embodiments.

In another embodiment, the compounds of Formula I includes compounds wherein $R^2$ is H, in conjunction with any of the above or below embodiments.

In another embodiment, the compounds of Formula I includes compounds wherein $R^3$ is H, halo, haloalkyl, $NO_2$, CN, $OR^7$, $SR^7$, $NR^7R^8$, $NR^7R^8$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$, in conjunction with any of the above or below embodiments.

In another embodiment, the compounds of Formula I includes compounds wherein $R^3$ is H, halo, haloalkyl, $NO_2$, CN, $OR^7$, $NR^7R^7$ or $C_{1-10}$-alkyl, in conjunction with any of the above or below embodiments.

In another embodiment, the compounds of Formula I includes compounds wherein $R^3$ is H, halo, haloalkyl or $C_{1-10}$-alkyl, in conjunction with any of the above or below embodiments.

In another embodiment, the compounds of Formula I includes compounds wherein $R^3$ is H, halo, methyl or ethyl, in conjunction with any of the above or below embodiments.

In another embodiment, the compounds of Formula I includes compounds wherein $R^3$ is H, F, Cl, methyl or ethyl, in conjunction with any of the above or below embodiments.

In another embodiment, the compounds of Formula I includes compounds wherein $R^3$ is H, in conjunction with any of the above or below embodiments.

In another embodiment, the compounds of Formula I includes compounds wherein each of $R^2$ and $R^3$, independently, is H or halo, in conjunction with any of the above or below embodiments.

In another embodiment, the compounds of Formula I includes compounds wherein each of $R^2$ and $R^3$, independently, is H, F, Cl, methyl or ethyl, in conjunction with any of the above or below embodiments.

In another embodiment, the compounds of Formula I includes compounds wherein each of $R^2$ and $R^3$, independently, is H or F, in conjunction with any of the above or below embodiments.

In another embodiment, the compounds of Formula I includes compounds wherein each of $R^2$ and $R^3$, independently, is H, in conjunction with any of the above or below embodiments.

In another embodiment, the compounds of Formula I includes compounds wherein $R^4$ is CN, $C(O)R^7$, $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally comprising 14 heteroatoms selected from N, O and S and optionally substituted with one or more substituents of $R^9$, in conjunction with any of the above or below embodiments.

In another embodiment, the compounds of Formula I includes compounds wherein $R^4$ is CN, $C(O)R^7$, $C_{1-4}$-alkylC(O)$R^7$, methyl, ethyl, propyl, isopropyl, cyclopropyl, butyl, isobutyl, tert-butyl, pentyl, neopentyl or $C_{1-4}$-alkyl-amino-$C_{1-4}$-alkyl or $C_{1-10}$-dialkylamino$C_{1-4}$-alkyl-, in conjunction with any of the above or below embodiments.

In another embodiment, the compounds of Formula I includes compounds wherein $R^4$ is methyl, ethyl, propyl, isopropyl, cyclopropyl, butyl, isobutyl, tert-butyl, pentyl or neopentyl, in conjunction with any of the above or below embodiments.

In another embodiment, the compounds of Formula I includes compounds wherein $R^5$ is $R^7$, $NR^7R^7$, $NR^7R^8$, $OR^7$, $SR^7$, $OR^8$, $SR^8$, $C(O)R^7$, $C(NCN)R^7$, $C(O)R^8$, $C(NCN)R^8$, $C(O)C(O)R^7$, $OC(O)R^7$, $COOR^7$, $C(O)C(O)R^8$, $OC(O)R^8$, $COOR^8$, $C(O)NR^7R^7$, $C(O)NR^7R^8$, $OC(O)NR^7R^8$, $NR^7C(O)R^7$, $NR^7C(O)R^8$, $NR^7C(O)NR^7R^7$, $NR^7C(O)NR^7R^8$, $NR^7(COOR^7)$, $NR^7(COOR^8)$, $S(O)_2R^7$, $S(O)_2R^8$, $S(O)_2NR^7R^7$, $S(O)_2NR^7R^8$, $NR^7S(O)_2NR^7R^8$, $NR^7S(O)_2R^7$ or $NR^7S(O)_2R^8$, in conjunction with any of the above or below embodiments.

In another embodiment, the compounds of Formula I includes compounds wherein $R^5$ is $NR^7R^7$, $NR^7R^8$, $C(O)R^7$, $C(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $NR^7(COOR^7)$, $NR^7(COOR^8)$, $S(O)_2R^7$, $S(O)_2R^8$, $S(O)_2NR^7R^7$, $S(O)_2NR^7R^8$, $NR^7S(O)_2NR^7R^8$, $NR^7S(O)_2R^7$ or $NR^7S(O)_2R^8$, in conjunction with any of the above or below embodiments.

In another embodiment, the compounds of Formula I includes compounds wherein $R^5$ is $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $S(O)_2NR^7R^7$, $S(O)_2NR^7R^8$, $NR^7S(O)_2NR^7R^8$, $NR^7S(O)_2R^7$ or $NR^7S(O)_2R^8$, in conjunction with any of the above or below embodiments.

In another embodiment, the compounds of Formula I includes compounds wherein $R^5$ is $NR^7R^7$, $NR^7R^8$, $C(O)R^7$, $C(O)R^8$, $C(O)NR^7R^7$, $C(O)NR^7R^8$, $NR^7C(O)R^7$, $NR^7C(O)R^8$, $S(O)_2R^7$, $S(O)_2R^8$, $S(O)_2NR^7R^7$, $S(O)_2NR^7R^8$, $NR^7S(O)_2R^7$ or $NR^7S(O)_2R^8$, in conjunction with any of the above or below embodiments.

In another embodiment, the compounds of Formula I includes compounds wherein $R^5$ is —$C(O)NR^7R^7$, $C(O)NR^7R^8$, $NR^7C(O)R^7$, $NR^7C(O)R^8$, $S(O)_2NR^7R^7$, $S(O)_2NR^7R^8$, $NR^7S(O)_2R^7$ or $NR^7S(O)_2R^8$, in conjunction with any of the above or below embodiments.

In another embodiment, the compounds of Formula I includes compounds wherein $R^5$ is $C(O)NR^7R^7$, $C(O)NR^7R^8$, $NR^7C(O)R^7$ or $NR^7C(O)R^8$, in conjunction with any of the above or below embodiments.

In another embodiment, the compounds of Formula I includes compounds wherein $R^5$ is —$C(O)NHC_{1-6}$-alkyl, $C(O)NHC_{2-6}$-alkenyl, $C(O)NHC_{2-6}$-alkynyl, $C(O)NHC_{3-6}$-cycloalkyl, $C(O)NHaryl$, $C(O)NHheteroaryl$, $NHC(O)C_{1-6}$-alkyl, $NHC(O)C_{2-6}$-alkenyl, $NHC(O)C_{2-6}$-alkynyl, $NHC(O)C_{3-6}$-cycloalkyl, $NHC(O)aryl$ or $NHC(O)heteroaryl$, in conjunction with any of the above or below embodiments.

In another embodiment, the compounds of Formula I includes compounds wherein $R^5$ is $C(O)NR^7R^7$ or $C(O)NR^7R^8$, in conjunction with any of the above or below embodiments.

In another embodiment, the compounds of Formula I includes compounds wherein $R^8$ is a ring selected from phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring is optionally substituted independently with 1-3 substituents of $R^9$, in conjunction with any of the above or below embodiments.

In another embodiment, the compounds of Formula I includes compounds wherein $R^1$ is phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, tetrahydrofuryl, pyrrblyl, tetrahydropyrrolyl, pyrazolyl, imidazolyl, triazolyl, tetrazolyl, thiazolyl, oxazolyl, oxazolinyl, isoxazolyl, isoxazolinyl, oxadiazolyl, isothiazolyl, indolyl, indolinyl, isoindolyl, benzofuranyl, dihydrobenzofuranyl, benzothiophenyl, benzisoxazolyl, benzopyrazolyl, benzothiazolyl, benzimidazolyl, piperidinyl, pyranyl, cyclopropyl, cyclobutyl or cyclohexyl, each of which is optionally substituted independently with 1-3 substituents of $R^9$;

each of $R^2$ and $R^3$, independently, is H, halo, haloalkyl or $C_{1-10}$-alkyl;

$R^4$ is CN, C(O)$R^7$, $C_{1-4}$-alkylC(O)$R^7$, methyl, ethyl, propyl, isopropyl, cyclopropyl, butyl, isobutyl, tert-butyl, pentyl, neopentyl or $C_{1-4}$-alkyl-amino-$C_{1-4}$-alkyl or $C_{1-10}$-dialkylamino$C_{1-4}$-alkyl-;

$R^5$ is $NR^7R^7$, $NR^7R^8$, C(O)$NR^7R^7$, C(O)$NR^7R^8$, $NR^7$C(O)$R^7$, $NR^7$C(O)$R^8$, $NR^7$C(O)$NR^7R^7$, $NR^7$C(O)$NR^7R^8$, $NR^7$(COOR$^7$), $NR^7$(COOR$^8$), S(O)$_2$$R^7$, S(O)$_2$$R^8$, S(O)$_2$$NR^7R^7$, S(O)$_2$$NR^7R^8$, $NR^7$S(O)$_2$$NR^7R^8$, $NR^7$S(O)$_2$$R^7$ or $NR^7$S(O)$_2$$R^8$;

each $R^6$, independently, is H, F, Cl, Br, CF$_3$, —OCF$_3$, C$_2$F$_5$, —OC$_2$F$_5$, —O—$C_{1-4}$-alkyl, —$C_{1-4}$-alkyl-O—$C_{1-6}$-alkyl, —S—$C_{1-6}$-alkyl, —$C_{1-4}$-alkyl-S—$C_{1-6}$-alkyl, —NH—$C_{1-6}$-alkyl, —N($C_{1-6}$-alkyl)$_2$, —$C_{1-4}$-alkyl-NH—$C_{1-4}$-alkyl, —$C_{1-3}$-alkyl-N($C_{1-4}$-alkyl)$_2$, NO$_2$, NH$_2$, CN, $C_{1-10}$-alkyl, the $C_{1-10}$-alkyl optionally substituted with one or more substituents of $R^9$;

each $R^7$, independently, is H, $C_{1-10}$-alkyl or $C_{3-10}$-cycloalkyl, wherein the $C_{1-10}$-alkyl and $C_{3-10}$-cycloalkyl optionally comprising 1-4 heteroatoms selected from N, O and S and optionally substituted with 1-3 substituents of $R^9$;

$R^8$ is a ring selected from phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring is optionally substituted independently with 1-3 substituents of $R^9$; and $R^9$ is H, halo, haloalkyl, CN, OH, NO$_2$, NH$_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-allyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In another embodiment, the compounds of Formula I includes compounds wherein $R^1$ is phenyl, naphthyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, oxazolinyl, isoxazolyl, isoxazolinyl, oxadiazolyl, isothiazolyl, piperidinyl, pyranyl, cyclopropyl, cyclobutyl or cyclohexyl, each of which is optionally substituted independently with 1-3 substituents of $R^9$;

each of $R^2$ and $R^3$, independently, is H, F, Cl, CF$_3$, methyl or ethyl;

$R^4$ is CN, C(O)$R^7$, $C_{1-4}$-alkylC(O)$R^7$, methyl, ethyl, propyl, isopropyl, cyclopropyl, butyl, isobutyl, tert-butyl, pentyl, neopentyl or $C_{1-4}$-alkyl-amino-$C_{1-4}$-alkyl or $C_{1-10}$-dialkylamino$C_{1-4}$-alkyl-;

$R^5$ is C(O)$NR^7R^7$, C(O)$NR^7R^8$, $NR^7$C(O)$R^7$, $NR^7$C(O)$R^8$, $NR^7$C(O)$NR^7R^7$, $NR^7$C(O)$NR^7R^8$, S(O)$_2$$NR^7R^7$, S(O)$_2$$NR^7R^8$, $NR^7$S(O)$_2$$NR^7R^8$, $NR^7$S(O)$_2$$R^7$ or $NR^7$S(O)$_2$$R^8$;

each $R^6$, independently, is H, F, Cl, Br, CF$_3$, —OCF$_3$, C$_2$F$_5$, —O—$C_{1-3}$-alkyl, —S—$C_{1-3}$-alkyl, —NH—$C_{1-3}$-alkyl, NO$_2$, NH$_2$, OH, CN, methyl, ethyl propyl or isopropyl;

each $R^7$, independently, is H, $C_{1-10}$-allyl or $C_{3-4}$-cycloalkyl, wherein the $C_{1-6}$-alkyl and $C_{3-6}$-cycloalkyl optionally comprising 1-4 heteroatoms selected from N, O and S and optionally substituted with 1-3 substituents of $R^9$;

$R^8$ is a ring selected from phenyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, isoxazolyl, isothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring is optionally substituted independently with 1-3 substituents of $R^9$; and $R^9$ is H, halo, haloalkyl, CN, OH, NO$_2$, NH$_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the Cl$_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, Cl$_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In another embodiment, the compounds of Formula I includes compounds wherein $R^1$ is phenyl, pyridyl, pyrimidyl, pyridazinyl, pyrazinyl, thiophenyl, furyl, pyrrolyl, pyrazolyl, imidazolyl, triazolyl, thiazolyl, oxazolyl, oxazolinyl, isoxazolyl, isoxazolinyl, oxadiazolyl or isothiazolyl, each of which is optionally substituted independently with 1-3 substituents of $R^9$;

each of $R^2$ and $R^3$, independently, is H, F, Cl, CF$_3$ or methyl;

$R^4$ is $C_{1-4}$-alkylC(O)$R^7$, methyl, ethyl, propyl, isopropyl, cyclopropyl, butyl, isobutyl, tert-butyl, pentyl, neopentyl or $C_{1-4}$-alkyl-amino-$C_{1-4}$-alkyl or $C_{1-4}$-dialkylamino$C_{1-4}$-alkyl-;

$R^5$ is C(O)$NR^7R^7$, C(O)$NR^7R^8$, $NR^7$C(O)$R^7$, $NR^7$C(O)$R^8$, $NR^7$C(O)$NR^7R^7$, $NR^7$C(O)$NR^7R^8$, S(O)$_2$$NR^7R^7$, S(O)$_2$$NR^7R^8$, $NR^7$S(O)$_2$$NR^7R^8$, $NR^7$S(O)$_2$$R^7$ or $NR^7$S(O)$_2$$R^8$;

each $R^6$, independently, is H, F, Cl, Br, CF$_3$, —OCF$_3$, C$_2$F$_5$, —O—$C_{1-3}$-alkyl, —S—$C_{1-3}$-alkyl, —NH—$C_{1-3}$-alkyl, NO$_2$, NH$_2$, OH, CN, methyl, ethyl propyl or isopropyl;

each $R^7$, independently, is H, methyl, ethyl, propyl, isopropyl, cyclopropyl, cyclobutyl, cyclopentyl or cyclohexyl, each of the cyclopropyl, cyclobutyl, cyclopentyl or cyclohexyl optionally substituted with 1-3 substituents of $R^9$;

R⁸ is a ring selected from phenyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, isoxazolyl, isothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring is optionally substituted independently with 1-3 substituents of $R^9$; and $R^9$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In another embodiment, the compounds of Formula I includes compounds, and pharmaceutically acceptable salts thereof, selected from N-cyclopropyl-3-(7-ethyl-1-(2-fluorophenyl)-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-4-methylbenzamide;

3-(1-(2-chlorophenyl)-7-methyl-6-oxo-6,7-dihydro-1H-pyrazolo[3,4-b]pyridin-5-yl)-N-cyclopropyl-5-fluoro-4-methylbenzamide;

N-cyclopropyl-3-fluoro-5-(1-(2-fluorophenyl)-7-methyl-6-oxo-6,7-dihydro-1H-pyrazolo[3,4-b]pyridin-5-yl)-4-methylbenzamide;

3-(1-(2,6-difluorophenyl)-7-methyl-6-oxo-6,7-dihydro-1H-pyrazolo[3,4-b]pyridin-5-yl)-4-methyl-N-(1-methyl-1H-pyrazol-5-yl)benzamide;

N-cyclopropyl-3-(1-(2,4-difluorophenyl)-7-methyl-6-oxo-6,7-dihydro-1H-pyrazolo[3,4-b]pyridin-5-yl)-5-fluoro-4-methylbenzamide;

3-(1-(2-chlorophenyl)-7-methyl-6-oxo-6,7-dihydro-1H-pyrazolo[3,4-b]pyridin-5-yl)-N-cyclopropyl-4-methylbenzamide;

N-cyclopropyl-3-(1-(2,4-difluorophenyl)-7-methyl-6-oxo-6,7-dihydro-1H-pyrazolo[3,4-b]pyridin-5-yl)-4-methylbenzamide;

N-cyclopropyl-4-methyl-3-(7-methyl-1-(2-methylphenyl)-6-oxo-6,7-dihydro-1H-pyrazolo[3,4-b]pyridin-5-yl)benzamide;

N-cyclopropyl-3-fluoro-4-methyl-5-(7-methyl-1-(2-methylphenyl)-6-oxo-6,7-dihydro-1H-pyrazolo[3,4-b]pyridin-5-yl)benzamide;

N-(3-(1-(2,4-difluorophenyl)-7-methyl-6-oxo-6,7-dihydro-1H-pyrazolo[3,4-b]pyridin-5-yl)-4-methylphenyl)cyclopropanecarboxamide;

N-cyclopropyl-3-fluoro-4-methyl-5-(7-methyl-1-(1-methylethyl)-6-oxo-6,7-dihydro-1H-pyrazolo[3,4-b]pyridin-5-yl)benzamide;

3-(1-(2,6-difluorophenyl)-7-methyl-6-oxo-6,7-dihydro-1H-pyrazolo[3,4-b]pyridin-5-yl)-N-3-isoxazolyl-4-methylbenzamide;

3-(1-(2,6-difluorophenyl)-7-methyl-6-oxo-6,7-dihydro-1H-pyrazolo[3,4-b]pyridin-5-yl)-5-fluoro-N-3-isoxazolyl-4-methylbenzamide;

N-cyclopropyl-4-(1-(2,6-difluorophenyl)-7-methyl-6-oxo-6,7-dihydro-1H-pyrazolo[3,4-b]pyridin-5-yl)-5-methyl-2-pyridinecarboxamide;

4-chloro-N-cyclopropyl-3-(1-(2,6-difluorophenyl)-7-methyl-6-oxo-6,7-dihydro-1H-pyrazolo[3,4-b]pyridin-5-yl)benzamide;

3-(1-(2,6-difluorophenyl)-7-methyl-6-oxo-6,7-dihydro-1H-pyrazolo[3,4-b]pyridin-5-yl)-5-fluoro-4-methyl-N-(1-methylethyl)benzamide;

3-(1-(2,6-difluorophenyl)-7-methyl-6-oxo-6,7-dihydro-1H-pyrazolo[3,4-b]pyridin-5-yl)-5-fluoro-N,4-dimethylbenzamide;

N-cyclopropyl-3-(1-(2,5-difluorophenyl)-7-methyl-6-oxo-6,7-dihydro-1H-pyrazolo[3,4-b]pyridin-5-yl)-5-fluoro-4-methylbenzamide;

N-cyclopropyl-3-(1-(2,5-difluorophenyl)-7-methyl-6-oxo-6,7-dihydro-1H-pyrazolo[3,4-b]pyridin-5-yl)-4-methylbenzamide;

3-(1-(2,5-difluorophenyl)-7-methyl-6-oxo-6,7-dihydro-1H-pyrazolo[3,4-b]pyridin-5-yl)-4-methyl-N-(1-methylcyclopropyl)benzamide;

3-(1-(2,5-difluorophenyl)-7-methyl-6-oxo-6,7-dihydro-1H-pyrazolo[3,4-b]pyridin-5-yl)-N-3-isoxazolyl-4-methylbenzamide;

3-(1-(2,4-difluorophenyl)-7-methyl-6-oxo-6,7-dihydro-1H-pyrazolo[3,4-b]pyridin-5-yl)-N-3-isoxazolyl-4-methylbenzamide;

3-(1-(2,6-difluorophenyl)-7-methyl-6-oxo-6,7-dihydro-1H-pyrazolo[3,4-b]pyridin-5-yl)-4-methyl-N-1,3-thiazol-2-ylbenzamide;

4-chloro-N-cyclopropyl-3-(1-(2,5-difluorophenyl)-7-methyl-6-oxo-6,7-dihydro-1H-pyrazolo[3,4-b]pyridin-5-yl)benzamide;

3-(1-(2,6-difluorophenyl)-7-methyl-6-oxo-6,7-dihydro-1H-pyrazolo[3,4-b]pyridin-5-yl)-4-methyl-N-(1-methylcyclopropyl)benzamide;

3-(1-(2,6-difluorophenyl)-7-methyl-6-oxo-6,7-dihydro-1H-pyrazolo[3,4-b]pyridin-5-yl)-5-fluoro-4-methylbenzamide;

3-(1-(2,6-difluorobenzyl)-7-methyl-6-oxo-6,7-dihydro-1H-pyrazolo[3,4-b]pyridin-5-yl)-4-methylbenzamide;

3-(1-(2,6-difluorophenyl)-7-methyl-6-oxo-6,7-dihydro-1H-pyrazolo[3,4-b]pyridin-5-yl)-4-methyl-N-(2-(methyloxy)-5-(trifluoromethyl)phenyl)benzamide;

N-cyclopropyl-3-(1-(2,6-difluorophenyl)-7-methyl-6-oxo-6,7-dihydro-1H-pyrazolo[3,4-b]pyridin-5-yl)-4-(hydroxymethyl)benzamide;

N-cyclopropyl-3-(1-(2,4-difluorophenyl)-7-ethyl-6-oxo-6,7-dihydro-1H-pyrazolo[3,4-b]pyridin-5-yl)-4-methylbenzamide;

N-cyclopropyl-3-(1-(2,6-difluorophenyl)-7-methyl-6-thioxo-6,7-dihydro-1H-pyrazolo[3,4-b]pyridin-5-yl)-4-methylbenzamide;

N-cyclopropyl-3-(1-(2,4-difluorophenyl)-7-(2,3-dihydroxypropyl)-6-oxo-6,7-dihydro-1H-pyrazolo[3,4-b]pyridin-5-yl)-4-methylbenzamide;

N-cyclopropyl-3-(1-(4-fluorophenyl)-7-methyl-6-oxo-6,7-dihydro-1H-pyrazolo[3,4-b]pyridin-5-yl)-4-methylbenzamide;

4-chloro-N-cyclopropyl-3-(1-(4-fluorophenyl)-7-methyl-6-oxo-6,7-dihydro-1H-pyrazolo[3,4-b]pyridin-5-yl)benzamide; and 1-cyclopropyl-3-(3-(1-(2,6-difluorophenyl)-7-methyl-6-oxo-6,7-dihydro-1H-pyrazolo[3,4-b]pyridin-5-yl)-4-methylphenyl)urea.

In another embodiment, the compounds of Formula I include compounds, and pharmaceutically acceptable salts thereof, selected from N-cyclopropyl-3-(7-ethyl-1-(2-fluorophenyl)-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-4-methylbenzamide;

3-(1-(2-chlorophenyl)-7-methyl-6-oxo-6,7-dihydro-1H-pyrazolo[3,4-b]pyridin-5-yl)-N-cyclopropyl-5-fluoro-4-methylbenzamide;

N-cyclopropyl-3-fluoro-5-(1-(2-fluorophenyl)-7-methyl-6-oxo-6,7-dihydro-1H-pyrazolo[3,4-b]pyridin-5-yl)-4-methylbenzamide;

3-(1-(2,6-difluorophenyl)-7-methyl-6-oxo-6,7-dihydro-1H-pyrazolo[3,4-b]pyridin-5-yl)-4-methyl-N-(1-methyl-1H-pyrazol-5-yl)benzamide;

N-cyclopropyl-3-(1-(2,4-difluorophenyl)-7-methyl-6-oxo-6,7-dihydro-1H-pyrazolo[3,4-b]pyridin-5-yl)-5-fluoro-4-methylbenzamide;

3-(1-(2-chlorophenyl)-7-methyl-6-oxo-6,7-dihydro-1H-pyrazolo[3,4-b]pyridin-5-yl)-N-cyclopropyl-4-methylbenzamide;

N-cyclopropyl-3-(1-(2,4-difluorophenyl)-7-methyl-6-oxo-6,7-dihydro-1H-pyrazolo[3,4-b]pyridin-5-yl)-4-methylbenzamide;

N-cyclopropyl-4-methyl-3-(7-methyl-1-(2-methylphenyl)-6-oxo-6,7-dihydro-1H-pyrazolo[3,4-b]pyridin-5-yl)benzamide;

N-cyclopropyl-3-fluoro-4-methyl-5-(7-methyl-1-(2-methylphenyl)-6-oxo-6,7-dihydro-1H-pyrazolo[3,4-b]pyridin-5-yl)benzamide;

N-(3-(1-(2,4-difluorophenyl)-7-methyl-6-oxo-6,7-dihydro-1H-pyrazolo[3,4-b]pyridin-5-yl)-4-methylphenyl)cyclopropanecarboxamide;

N-cyclopropyl-3-fluoro-4-methyl-5-(7-methyl-1-(1-methylethyl)-6-oxo-6,7-dihydro 1H-pyrazolo[3,4-b]pyridin-5-yl)benzamide;

N-cyclopropyl-3-(1-(2,5-difluorophenyl)-7-methyl-6-oxo-6,7-dihydro-1H-pyrazolo[3,4-b]pyridin-5-yl)-5-fluoro-4-methylbenzamide;

N-cyclopropyl-3-(1-(2,5-difluorophenyl)-7-methyl-6-oxo-6,7-dihydro-1H-pyrazolo[3,4-b]pyridin-5-yl)-4-methylbenzamide;

3-(1-(2,5-difluorophenyl)-7-methyl-6-oxo-6,7-dihydro-1H-pyrazolo[3,4-b]pyridin-5-yl)-4-methyl-N-(1-methylcyclopropyl)benzamide;

3-(1-(2,6-difluorophenyl)-7-methyl-6-oxo-6,7-dihydro-1H-pyrazolo[3,4-b]pyridin-5-yl)-4-methyl-N-(1-methylcyclopropyl)benzamide;

N-cyclopropyl-3-(1-(2,4-difluorophenyl)-7-ethyl-6-oxo-6,7-dihydro-1H-pyrazolo[3,4-b]pyridin-5-yl)-4-methylbenzamide;

N-cyclopropyl-3-(1-(2,6-difluorophenyl)-7-methyl-6-thioxo-6,7-dihydro-1H-pyrazolo[3,4-b]pyridin-5-yl)-4-methylbenzamide;

N-cyclopropyl-3-(1-(2,4-difluorophenyl)-7-(2,3-dihydroxypropyl)-6-oxo-6,7-dihydro-1H-pyrazolo[3,4-b]pyridin-5-yl)-4-methylbenzamide;

N-cyclopropyl-3-(1-(4-fluorophenyl)-7-methyl-6-oxo-6,7-dihydro-1H-pyrazolo[3,4-b]pyridin-5-yl)-4-methylbenzamide;

4-chloro-N-cyclopropyl-3-(1-(4-fluorophenyl)-7-methyl-6-oxo-6,7-dihydro-1H-pyrazolo[3,4-b]pyridin-5-yl)benzamide; and 1-cyclopropyl-3-(3-(1,2,6-difluorophenyl)-7-methyl-6-oxo-6,7-dihydro-1H-pyrazolo[3,4-b]pyridin-5-yl)-4-methylphenyl)urea.

In another embodiment, the compounds of Formula I include compounds, and pharmaceutically acceptable salts thereof, selected from N-cyclopropyl-3-(7-ethyl-1-(2-fluorophenyl)-6-oxo-6,7-dihydro-1H-pyrazolo[3,4-b]-pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-4-methylbenzamide;

3-(1-(2-chlorophenyl)-7-methyl-6-oxo-6,7-dihydro-1H-pyrazolo[3,4-b]pyridin-5-yl)-N-cyclopropyl-5-fluoro-4-methylbenzamide;

N-cyclopropyl-3-(1-(2,4-difluorophenyl)-7-methyl-6-oxo-6,7-dihydro-1H-pyrazolo[3,4-b]pyridin-5-yl)-5-fluoro-4-methylbenzamide;

3-(1-(2-chlorophenyl)-7-methyl-6-oxo-6,7-dihydro-1H-pyrazolo[3,4-b]pyridin-5-yl)-N-cyclopropyl-4-methylbenzamide;

N-cyclopropyl-3-(1-(2,4-difluorophenyl)-7-methyl-6-oxo-6,7-dihydro-1H-pyrazolo[3,4-b]pyridin-5-yl)-4-methylbenzamide;

N-cyclopropyl-4-methyl-3-(7-methyl-1-(2-methylphenyl)-6-oxo-6,7-dihydro-1H-pyrazolo[3,4-b]pyridin-5-yl)benzamide;

N-cyclopropyl-3-fluoro-4-methyl-5-(7-methyl-1-(2-methylphenyl)-6-oxo-6,7-dihydro-1H-pyrazolo[3,4-b]pyridin-5-yl)benzamide;

N-(3-(1-(2,4-difluorophenyl)-7-methyl-6-oxo-6,7-dihydro-1H-pyrazolo[3,4-b]pyridin-5-yl)-4-methylphenyl)cyclopropanecarboxamide;

N-cyclopropyl-3-(1-(2,5-difluorophenyl)-7-methyl-6-oxo-6,7-dihydro-1H-pyrazolo[3,4-b]pyridin-5-yl)-5-fluoro-4-methylbenzamide;

N-cyclopropyl-3-(1-(2,5-difluorophenyl)-7-methyl-6-oxo-6,7-dihydro-1H-pyrazolo[3,4-b]pyridin-5-yl)-4-methylbenzamide;

N-cyclopropyl-3-(1-(2,4-difluorophenyl)-7-ethyl-6-oxo-6,7-dihydro-1H-pyrazolo[3,4-b]pyridin-5-yl)-4-methylbenzamide;

N-cyclopropyl-3-(1-(4-fluorophenyl)-7-methyl-6-oxo-6,7-dihydro-1H-pyrazolo[3,4-b]pyridin-5-yl)-4-methylbenzamide;

4-chloro-N-cyclopropyl-3-(1-2,6-difluorophenyl)-7-methyl-6-oxo-6,7-dihydro-1H-pyrazolo[3,4-b]pyridin-5-yl)benzamide; and 4-chloro-N-cyclopropyl-3-(1-(4-fluorophenyl)-7-methyl-6-oxo-6,7-dihydro-1H-pyrazolo[3,4-b]pyridin-5-yl)benzamide.

In another embodiment, the invention provides the compound N-cyclopropyl-3-(1-(2,4-difluorophenyl)-7-methyl- 6-oxo-6,7-dihydro-1H-pyrazolo[3,4-b]pyridin-5-yl)-5-fluoro-4-methylbenzamide, or a pharmaceutically acceptable salt form thereof.

In another embodiment, the invention provides the compound N-cyclopropyl-3-(1-(2,4-difluorophenyl)-7-methyl-6-oxo-6,7-dihydro-1H-pyrazolo[3,4-b]pyridin-5-yl)-4-methylbenzamide, or a pharmaceutically acceptable salt form thereof.

In another embodiment, the invention provides the compound N-(3-(1-(2,4-difluorophenyl)-7-methyl-6-oxo-6,7-dihydro-1H-pyrazolo[3,4-b]pyridin-5-yl)-4-methylphenyl)cyclopropanecarboxamide, or a pharmaceutically acceptable salt form thereof.

In another embodiment, the invention provides the compound N-cyclopropyl-3-(1-(2,6-difluorophenyl)-7-methyl-6-oxo-6,7-dihydro-1H-pyrazolo[3,4-b]pyridin-5-yl)-4-methylbenzamide, or a pharmaceutically acceptable salt form thereof.

In another embodiment, the invention provides the compound 4-chloro-N-cyclopropyl-3-(1-(2,6-difluorophenyl)-7-methyl-6-oxo-6,7-dihydro-1H-pyrazolo[3,4-b]pyridin-5-yl)benzamide, or a pharmaceutically acceptable salt form thereof.

In another embodiment, the invention provides the compound 3-(1-(2,6-difluorophenyl)-7-methyl-6-oxo-6,7-dihydro-1H-pyrazolo[3,4-b]pyridin-5-yl)-4-methyl-N-(1-methyl-1H-pyrazol-5-yl)benzamide, or a pharmaceutically acceptable salt form thereof.

In another embodiment, the compounds of Formula I includes compounds, and pharmaceutically acceptable salts thereof, selected from 3-(1-(2,6-difluorophenyl)-7-methyl-6-oxo-6,7-dihydro-1H-pyrazolo[3,4-b]pyridin-5-yl)-N-3-isoxazolyl-4-methylbenzamide;

3-(1-(2,6-difluorophenyl)-7-methyl-6-oxo-6,7-dihydro-1H-pyrazolo[3,4-b]pyridin-5-yl)-5-fluoro-N-3-isoxazolyl-4-methylbenzamide;

N-cyclopropyl-4-(1-(2,6-difluorophenyl)-7-methyl-6-oxo-6,7-dihydro-1H-pyrazolo[3,4-b]pyridin-5-yl)-5-methyl-2-pyridinecarboxamide;

4-chloro-N-cyclopropyl-3-(1-(2,6-difluorophenyl)-7-methyl-6-oxo-6,7-dihydro-1H-pyrazolo[3,4-b]pyridin-5-yl)benzamide;

3-(1-(2,6-difluorophenyl)-7-methyl-6-oxo-6,7-dihydro-1H-pyrazolo[3,4-b]pyridin-5-yl)-5-fluoro-4-methyl-N-(1-methylethyl)benzamide;

3-(1-(2,6-difluorophenyl)-7-methyl-6-oxo-6,7-dihydro-1H-pyrazolo[3,4-b]pyridin-5-yl)-5-fluoro-N,4-dimethylbenzamide;

3-(1-(2,5-difluorophenyl)-7-methyl-6-oxo-6,7-dihydro-1H-pyrazolo[3,4-b]pyridin-5-yl)-N-3-isoxazolyl-4-methylbenzamide;

3-(1-(2,4-difluorophenyl)-7-methyl-6-oxo-6,7-dihydro-1H-pyrazolo[3,4-b]pyridin-5-yl)-N-3-isoxazolyl-4-methylbenzamide;

3-(1-(2,6-difluorophenyl)-7-methyl-6-oxo-6,7-dihydro-1H-pyrazolo[3,4-b]pyridin-5-yl)-4-methyl-N-1,3-thiazol-2-ylbenzamide;

4-chloro-N-cyclopropyl-3-(1-(2,5-difluorophenyl)-7-methyl-6-oxo-6,7-dihydro-1H-pyrazolo[3,4-b]pyridin-5-yl)benzamide;

3-(1-(2,6-difluorophenyl)-7-methyl-6-oxo-6,7-dihydro-1H-pyrazolo[3,4-b]pyridin-5-yl)-5-fluoro-4-methylbenzamide;

3-(1-(2,6-difluorophenyl)-7-methyl-6-oxo-6,7-dihydro-1H-pyrazolo[3,4-b]pyridin-5-yl)-4-methylbenzamide;

3-(1-(2,6-difluorophenyl)-7-methyl-6-oxo-6,7-dihydro-1H-pyrazolo[3,4-b]pyridin-5-yl)-4-methyl-N-(2-(methyloxy)-5-(trifluoromethyl)phenyl)benzamide; and N-cyclopropyl-3-(1-(2,6-difluorophenyl)-7-methyl-6-oxo-6,7-dihydro-1H-pyrazolo[3,4-b]pyridin-5-yl)-4-(hydroxymethyl)benzamide.

In another embodiment, the invention provides compounds of Formula I-B, and pharmaceutically acceptable salts thereof, wherein

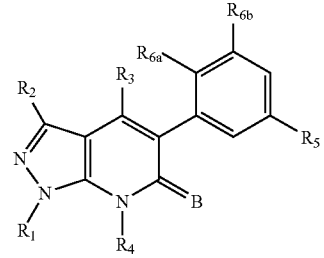

I-B

B is O, S or N—CN;

$R^1$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$, or $R^1$ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^9$;

each of $R^2$ and $R^3$, independently, is H or halo;

$R^4$ is CN, C(O)$R^7$, $C_{1-4}$-alkyl, $C_{2-6}$-alkenyl, $C_{2-6}$-alkynyl or $C_{3-8}$-cycloalkyl, each of the $C_{1-6}$-alkyl, $C_{2-4}$-alkenyl, $C_{2-6}$-alkynyl and $C_{3-8}$-cycloalkyl optionally comprising 1-4 heteroatoms selected from N, O and S and optionally substituted with one or more substituents of $R^9$;

$R^5$ is COOR$^7$, COOR$^8$, C(O)NR$^7$R$^7$, C(O)NR$^7$R$^8$, NR$^7$C(O)R$^1$, NR$^7$C(O)R$^8$, NR$^7$C(O)NR$^7$R$^7$, NR$^7$C(O)NR$^7$R$^8$, S(O)$_2$NR$^7$R$^7$, S(O)$_2$NR$^7$R$^8$, NR$^7$S(O)$_2$NR$^7$R$^8$, NR$^7$S(O)$_2$R$^7$ or NR$^7$S(O)$_2$R$^8$;

$R^{6a}$ is H, halo, haloalkyl, NO$_2$, CN, OR$^7$, NR$^7$R$^7$ or $C_{1-6}$-alkyl;

$R^{6b}$ is H, halo, haloalkyl, NO$_2$, CN, OR$^7$, NR$^7$R$^7$ or $C_{1-6}$-alkyl;

each $R^7$, independently, is H, $C_{1-6}$-alkyl or $C_{3-6}$-cycloalkyl, each of the $C_{1-6}$-alkyl, and $C_{3-6}$-cycloalkyl optionally substituted with one or more substituents of $R^9$;

$R^8$ is a ring selected from phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring is optionally substituted independently with 1-3 substituents of $R^9$; and $R^9$ is H, halo, haloalkyl, CN, OH, NO$_2$, NH$_2$, acetyl, oxo, $C_{1-10}$-alkyl, C210-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In another embodiment, the invention provides compounds of Formula I-C, and pharmaceutically acceptable salts thereof, wherein

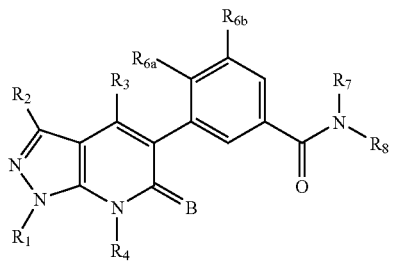

I-C

B is O, S or N—CN;

$R^1$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$, or $R^1$ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^9$;

each of $R^2$ and $R^3$, independently, is H or F;

$R^4$ is CN, $C(O)R^7$, $C_{1-4}$-alkyl, $C_{2-4}$-alkenyl, $C_{2-6}$-alkynyl or $C_{3-8}$-cycloalkyl, each of the $C_{1-6}$-alkyl, $C_{2-6}$-alkenyl, $C_{2-6}$-alkynyl and $C_{3-8}$-cycloalkyl optionally comprising 1-4 heteroatoms selected from N, O and S and optionally substituted with one or more substituents of $R^9$;

$R^{6a}$ is H, halo, haloalkyl, $NO_2$, CN, $OR^7$, $NR^7R^7$ or $C_{1-6}$-alkyl;

$R^{6b}$ is H, halo, haloalkyl, $NO_2$, CN, $OR^7$, $NR^7R^7$ or $C_{1-6}$-alkyl;

each $R^7$, independently, is H, $C_{1-4}$-alkyl or $C_{3-10}$-cycloalkyl, each of the $C_{1-6}$-alkyl, and $C_{3-6}$-cycloalkyl optionally substituted with one or more substituents of $R^9$;

$R^8$ is a ring selected from phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring is optionally substituted independently with 1-3 substituents of $R^9$; and $R^9$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In yet another embodiment, the compounds of Formulas I, I-B and I-C include each individual example, and each and every pharmaceutically acceptable salt form thereof, described hereinbelow.

DEFINITIONS

The following definitions should assist in understanding the invention described herein.

The term "comprising" is meant to be open ended, including the indicated component(s), but not excluding other elements.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$). Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Examples of alkenyl radicals include, without limitation, ethenyl, propenyl, alkyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of such radicals include, without limitation, ethynyl, propynyl (propargyl), butynyl, and the like.

The term "alkoxy" or "alkoxyl", when used alone or in combination, embraces linear or branched oxygen-containing radicals each having alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. Unless otherwise specified, the "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane and partially saturated monocyclic groups such as cyclopentene, cyclohexene or cyclohexadiene. The partially saturated groups are also encompassed in the term "cycloalkenyl" as defined below.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, aza-quinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heteroaryl" also embraces bicyclic radicals wherein 5- or 6-membered heteroaryl radicals are fused/condensed with aryl radicals or unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "aminocarbonyl" denotes an amide group of the formula —C(=O)NH$_2$.

The terms "alkylthio" and "thioalkoxyl" embrace radicals containing a linear or branched alkyl radical, of one to ten carbon atoms, attached to a divalent sulfur atom. An example of "alkylthio" is methylthio, (CH$_3$S—).

The term "Formula I" includes any sub formulas, such as Formulas I-B and I-C.

The term "pharmaceutically-acceptable" when used with reference to a compound of Formulas I, I-B and I-C is intended to refer to a form of the compound that is safe for administration. For example, a free base, a salt form, a solvate, a hydrate, a prodrug or derivative form of a compound of Formula I, I-B or of Formula I-C, which has been approved for mammalian use, via oral ingestion or any other route of administration, by a governing body or regulatory agency, such as the Food and Drug Administration (FDA) of the United States, is pharmaceutically acceptable.

Included in the compounds of Formulas I, I-B and I-C are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I and I-B may be prepared from an inorganic acid or from an organic acid. Examples of such inorganic acids are hydrochloric, hydrobromic, hydroiodic, hydrofluoric, nitric, carbonic, sulfonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I and II include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I and I-B.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid (HCl), hydrobromic acid (HBr), citric acid, sulphuric acid and phosphoric acid and such organic acids as oxalic acid, stearic and, salicylic acid, pamoic acid, gluconic acid, ethanesulfonic acid, methanesulfonic acid (MSA), benzenesulfonic acid (BSA), toluenesulfonic acid, tartaric acid, fumaric acid, medronic acid, napsylic acid, maleic acid, succinic acid and citric acid. Other examples include salts with alkali metals or alkaline earth metals such as sodium, potassium, calcium or magnesium, or with organic bases.

Additional examples of such salts can be found in Berge et al., J. Pharm. Sci., 66, 1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "pharmaceutically-acceptable derivative" as used herein, denotes a derivative, which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formulas I, I-B and I-C. A "pharmaceutically-acceptable prodrug" as used herein, denotes a prodrug, which is pharmaceutically acceptable. Pharmaceutically acceptable modifications to the compounds of Formula I are readily appreciated by those of ordinary skill in the art.

The compound(s) of Formulas I, I-B and I-C may be used to treat a subject by administering the compound(s) as a pharmaceutical composition. To this end, the compound(s) can be combined with one or more carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies.

The term "leaving groups" (also denoted as "LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I, I-B and I-C. The compounds of Formulas I, I-B and I-C can be synthesized according to the procedures described in the following Schemes 1-8 (corresponding to general Methods A, B, D, E, F, G, H and I, respectively) and scheme 9, wherein the substituents are as defined for Formulas I and I-B, above, except where further noted. The synthetic methods described below are merely exemplary, and the compounds of the invention may also be synthesized by alternate routes as appreciated by persons of ordinary skill in the art.

The following list of abbreviations used throughout the specification represent the following and should assist in understanding the invention:
ACN, MeCN—acetonitrile
BSA—bovine serum albumin
BOP—benzotriazol-1-yl-oxy hexafluorophosphate
$Br_2$—bromine
CDI—carbonyldiimidazole
$CS_2CO_3$—cesium carbonate
$CHCl_3$—chloroform
$CH_2Cl_2$, DCM—dichloromethane, methylene chloride
DCC—dicyclohexylcarbodiimide
DIC—1,3-diisopropylcarbodiimide
DIEA,$(iPr)_2$Net—diisopropylethylamine
DME—dimethoxyethane
DMF—dimethylformamide
DMAP—4-dimethylaminopyridine
DMSO—dimethylsulfoxide
EDC—1-(3-dimethylaminopropyl)-3-ethylcarbodiimide
$Et_2O$—diethyl ether
EtOAc—ethyl acetate
G, g, gm—gram
h,hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
LG—leaving group
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
$NaOCH_3$—sodium methoxide
NaOH—sodium hydroxide
$Na_2SO_4$—sodium sulfate
NBS—N-bromosuccinimide
$NH_4Cl$—ammonium chloride
$NH_4OH$—ammonium hydroxide
NMP—N-methylpyrrolidinone P(t-bu)₃—tri(tert-butyl)phosphine
PBS—phosphate buffered saline
Pd/C—palladium on carbon
Pd(PPh₃)₄—palladium(0)triphenylphosphine tetrakis
Pd(dppf)Cl₂-palladium(1,1-bisdiphenylphosphinoferrocene) II chloride
Pd(OAc)₂—palladium acetate
PyBop—benzotriazol-1-yl-oxy-tripyrrolidino-phosphonium hexafluorophosphate
RT, rt—room temperature
TBTU—O-benzotriazol-1-yl-N,N,N',N'-tetramethyluronium tetrafluoroborate
TEA, Et₃N—triethylamine
TFA—trifluoroacetic acid
THF—tetrahydrofuran
UV—ultraviolet light peratures, to afford the cyclized pyrazolo-pyridinone intermediate 4. Alkylation of pyridinone 4 generally yields a mixture of non-selective region-isomeric alkylated products 5 and 6, as shown. Upon purification and isolation of the desired $R^4$-substituted pyrazolo-pyridinone 5, it may be brominated to afford the corresponding bromine adduct 7, which can be subjected to suitable Suzuki Coupling conditions, such as those shown in scheme 1, with a desired boronic ester intermediate 9 to afford the desired substituted pyrazolo-pyridinone 8.

The boronic ester intermediates 9 may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as

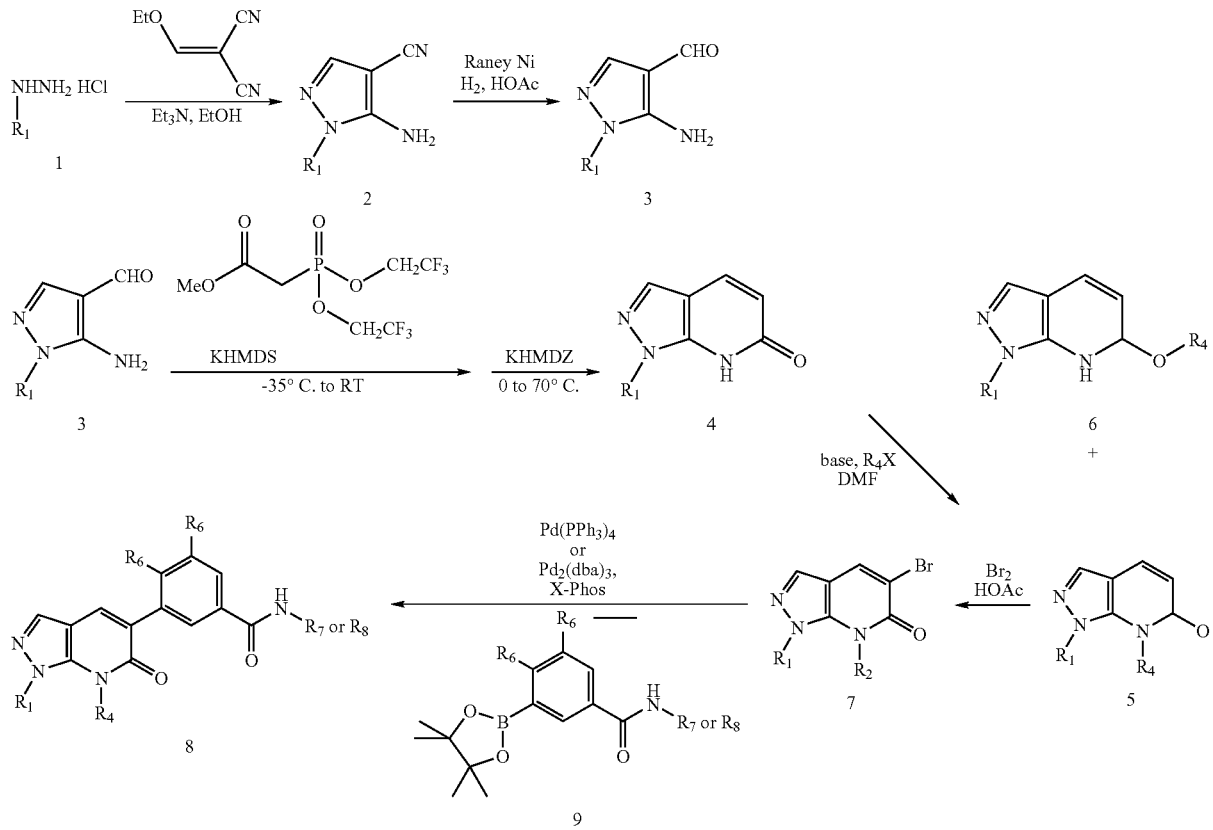

Scheme 1 (Method A)

Phenyl-substituted pyrazolo-pyridinones 8, (where each of $A^{1-4}$ in Formula I is CH or $CR^6$ and $R^5$ as shown is an amide linker; the ring shown as a phenyl ring in scheme 1 is generally referred to throughout the specification as the "B" ring) may be made by the method generally described in Scheme 1, also designated herein as Method A. As shown, an amino pyrazolo-carbaldehyde 3 may be made from the reaction of an appropriate substituted hydrazine 1 (or its HCl salt) with 2-(ethoxymethylene) malononitrile followed by the Raney-Nickel catalyzed hydrogenation of the 4-carbonitrile-pyrazole to the 4-carbaldehyde-pyrazole 3. Pyrazole 3 can then be reacted with methyl p,p-bis(2,2,2-trifluoroethyl)-phosphonoacetate in the presence of excess KHMDS, at suitable temperatures, to afford the cyclized pyrazolo-pyridinone intermediate 4.

protein kinase, especially p38 kinase, inhibitors for treating inflammation and related conditions", both publications of which are hereby incorporated herein by reference in their entirety.

The Suzuki method is a reaction using a borane reagent, such as a dioxaborolane intermediate 9 (also described in scheme 3 below as a borane B-A intermediate 8), and a suitable leaving group containing reagent, such as the Br-pyrazolo-pyridinone 7 (Br is a suitable halogen leaving group "LG"). As appreciated to one of ordinary skill in the art, Suzuki reactions also utilize a palladium catalyst. Suitable palladium catalysts include Pd(PPh₃)₄, Pd(OAc)₂ or Pd(dppf)Cl₂. Where LG is a halide, the halide may be an iodide, a bromide or even a chloride (chloro-pyridyl or chloro-picolinyl B rings undergo Suzuki reactions in the presence of Pd(OAc)$_2$). Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular pyrazolo-pyridinone 7 and/or boronic acid or ester 9, as appreciated by those skilled in the art. In addition, where the B ring is an aromatic moiety, such as phenyl, the reaction may be complete in a short period of time with heat.

Other methods of installing the boronate on a desired aromatic ring are known. For example metal coupling chemistry, such Stille, Kumada, Negishi coupling methods, and the like, may be employed to the pyrazolo-pyridinone cores 5 or 7 to prepare desired cyclic B-ring-substituted intermediates.

shown above, to provide the R$^4$ substituted intermediate 13, as appreciated by those of ordinary skill in the art. The corresponding bromine adduct 13, can be subjected to suitable Suzuki Coupling conditions, such as those shown in scheme 1, with a desired boronic ester intermediate 9 to afford the desired substituted pyrazolo-pyridinone 8.

Scheme 3 (Method D)

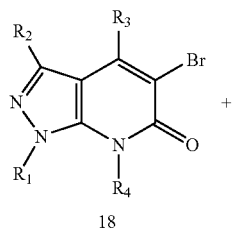

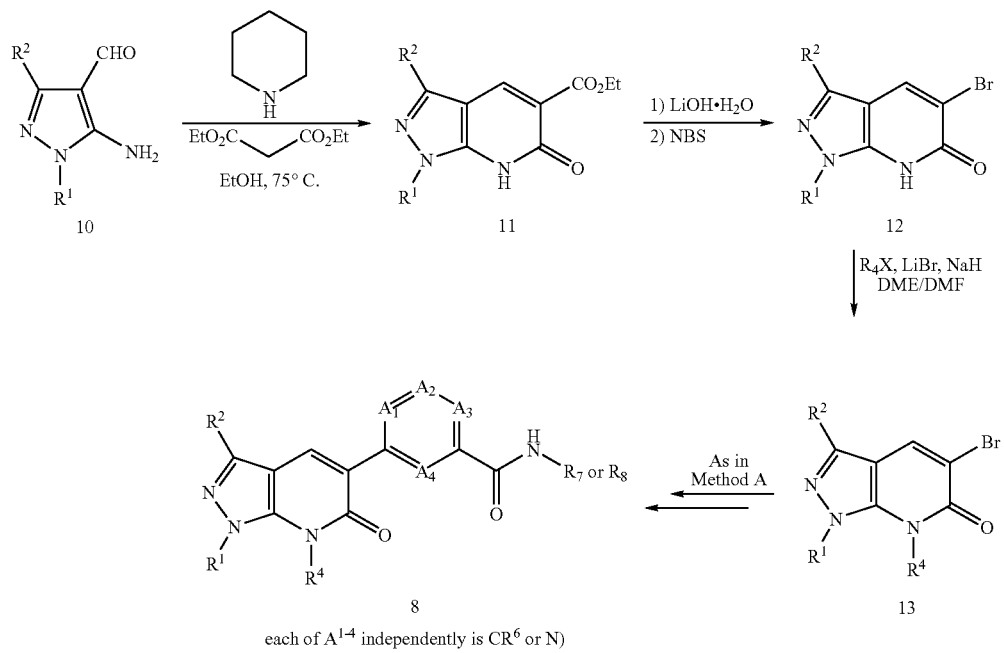

each of A$^{1-4}$ independently is CR$^6$ or N)

Alternatively, substituted pyrazolo-pyridinones 8, (where each of A$^{1-4}$ independently, is either N or CR$^6$ and R$^5$ as shown is an amide linker; the ring shown as a phenyl or pyridyl ring in scheme 2 is generally referred to throughout the specification as the "B" ring) may be made by the method generally described in Scheme 1, also designated herein as Method B. In method B, pyrazole 10 can be treated with diethyl malonate in the presence of piperidine to provide the bicyclic pyrazolo-pyridinone intermediate 11. Saponification of the ester group to the corresponding acid moiety of intermediate 11, followed by bromination with a suitable bromine delivery agent, such as NBS, affords the corresponding bromine intermediate 12. Compound 12 can be subject to alkylation or other functionalization, such as methylation as -continued

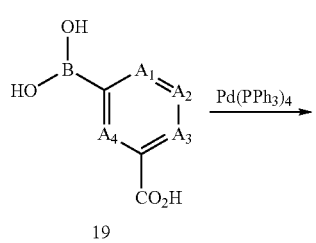

-continued

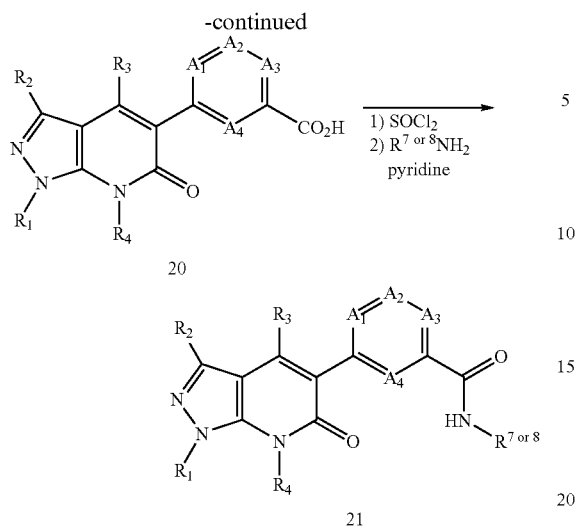

Alternatively, substituted pyrazolo-pyridinones 21, (where each of $A^{1-4}$ independently, of the B ring is either N or $CR^6$ and $R^5$ as shown is an amide linker) may be made by the method generally described in Scheme 3, also designated herein as Method D. In method D, bromo pyrazolo-pyridinone 18 can be reacted with a desired B-ring substituted boronic acid 19 in the presence of a suitable palladium catalyst, such as those shown or described in schemes 2 and 3 above, to provide the pyrazolo-pyridinone intermediate 11. Saponification of the ester group to the corresponding acid moiety of intermediate 20 with the carboxylid acid available to vary the linker region $R^5$ of Formulas I and II, as well the desired $R^7$, $R^8$ and $R^9$ groups which are attached therefrom. For example, and as shown in scheme 4, the acid of compounds 20 can be activated to coupling via various well known acid LG's, such as conversion to the corresponding acid chloride species as shown, followed by treatment with a suitable primary or secondary nucleophilic moiety, such as an appropriately substituted amine as shown, to afford the corresponding desired pyrazolo-pyridinone product 21.

Alternatively, substituted pyrazolo-pyridinones 21, (where each of $A^{1-4}$ independently, of the B ring is either N or $CR^6$ and $R^5$ as shown is an amide linker) may be made by the method generally described in Scheme 4, also designated herein as Method E. In method E, t-butyl protected pyrazolo-pyridinone 22 can be brominated by reaction with a suitable bromine source in the presence of a suitable acid, such as glacial acetic acid as shown. The bromide adduct 23 can then be alkylated (shown) or acylated (not shown), or a desired $R^1$ group can be inserted, on the available pyrazole nitrogen under basic conditions, such as those described in scheme 1 or those shown above. The corresponding $R^1$ group functionalized adduct 24 can be subjected to suitable Suzuki coupling conditions, such as those shown in scheme 1, with a desired boronic ester intermediate 9 (not shown in scheme 4) to afford the desired substituted pyrazolo-pyridinone 21.

Scheme 4 (Method E)

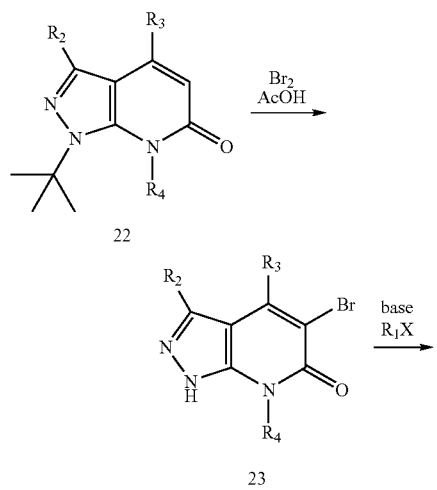

Scheme 5 (Method F)

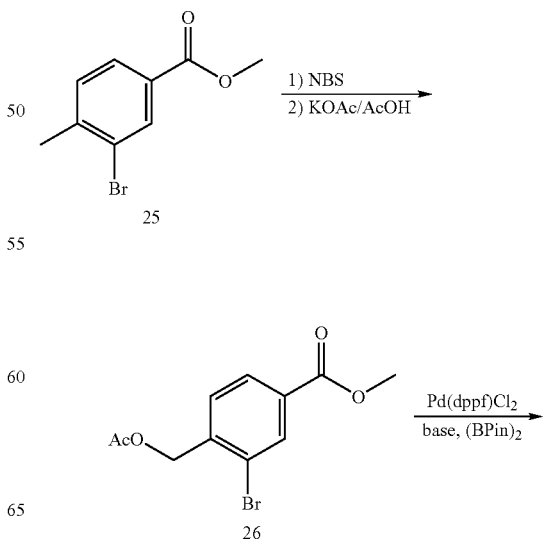

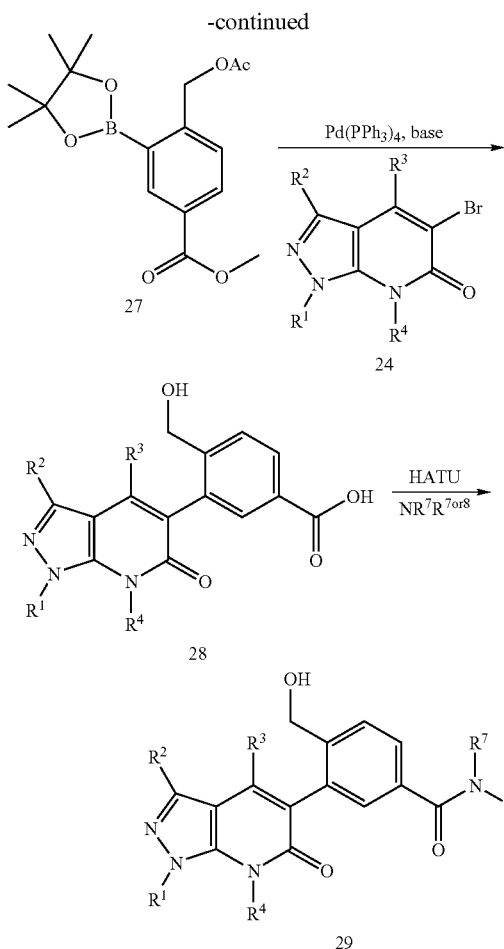

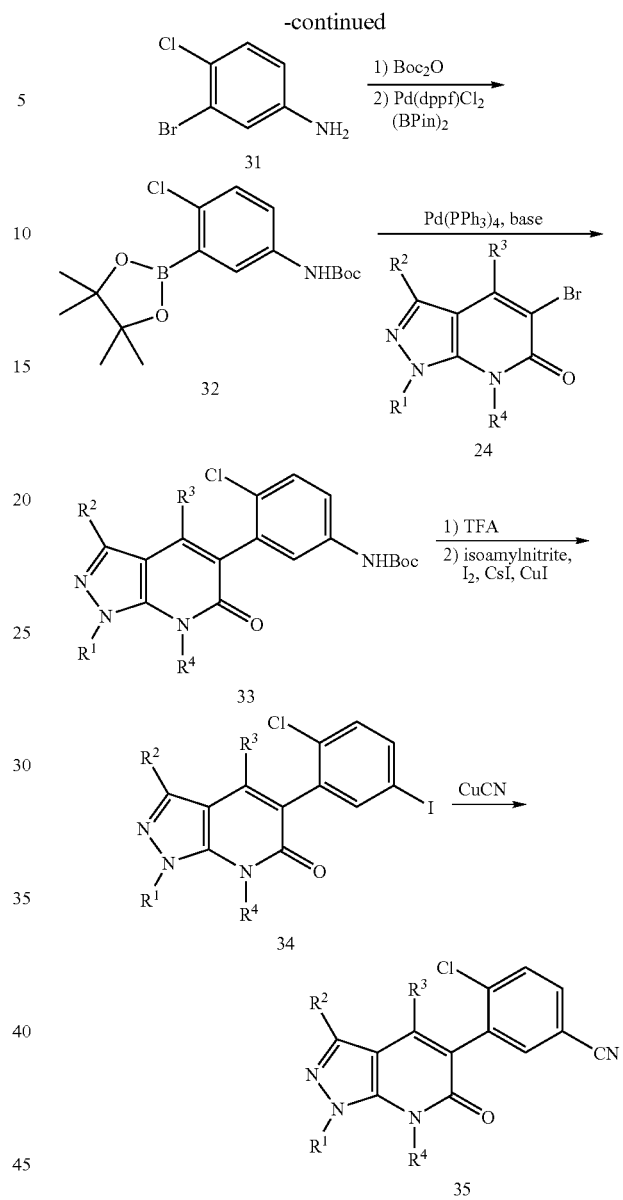

Substituted pyrazolo-pyridinones 29 (where each of $A^{1-4}$ independently, of the B ring is $CR^6$ and $R^5$ as shown is an amide linker) may be made by the method generally described in Scheme 5, also designated herein as Method F. In method F, the methyl group of bromo-benzoate 25 can be acetylated by first reaction with a suitable bromine source, such as NBS, in the presence of an acetate salt and a suitable acid, such as potassium acetate and acetic acid as shown. The bromide of the acetate adduct 26 can then be converted to the corresponding boronate 27 (as shown; see schemes 1 and 3), and the methyl benzoate intermediate 27 can be reacted with pyrazolo-pyridinone 24 under suitable Suzuki or Suzuki-like coupling conditions, such as those shown above and in scheme 1, to afford the coupled intermediate (not shown) which ester is hydrolized during basic work-up to afford acid 28. Acid 28 can be converted to the corresponding amide under conventional conditions using known reagents, such as those shown above and those described in scheme 3 above and scheme 9 below.

Scheme 6 (Method G)

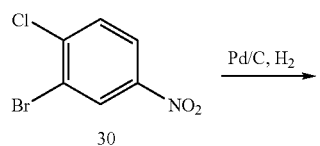

Substituted pyrazolo-pyridinones 35 (where each of $A^{1-4}$, independently, of the B ring is $CR^6$ and $R^5$ as shown is CN) may be made by the method generally described in Scheme 6, also designated herein as Method G. In method G, the nitro group of chloro-bromo-nitrobenzene 30 can be reduced using conventional methods, such as by hydrogenation, to afford the free amine 31. Amine 31 can be first protected with a suitable protecting group such as BOC, and then converted to the corresponding boronate 32 (as shown; see scheme 1). Boronate intermediate 32 can be reacted with pyrazolo-pyridinone 24 under suitable Suzuki or like coupling conditions, such as those shown above and in scheme 1, to afford the coupled intermediate 33. Boc amine 33 can be converted to the corresponding iodide 34 under conventional conditions, such as by first removing the BOc group and converting the resulting amine to iodide using known reagents, such as those shown above. Iodide 34 can be converted to the corresponding cyano group under conventional conditions, such as those described above.

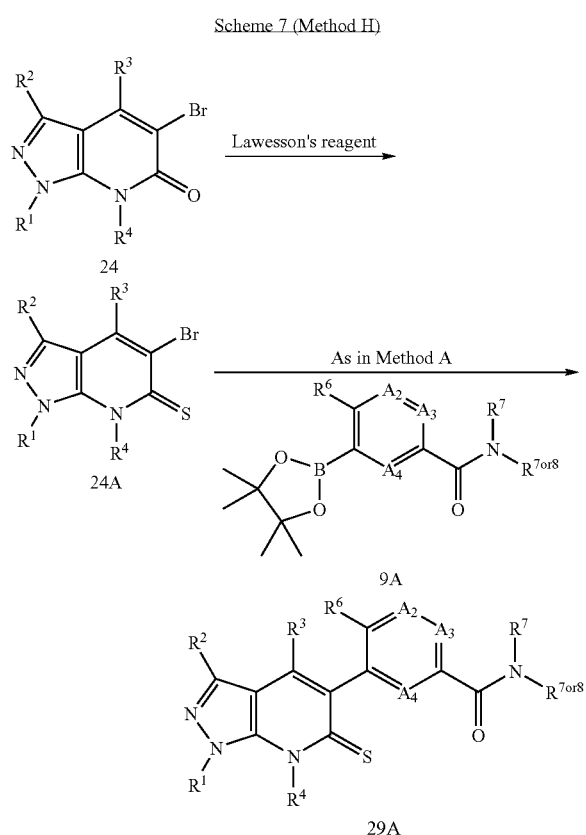

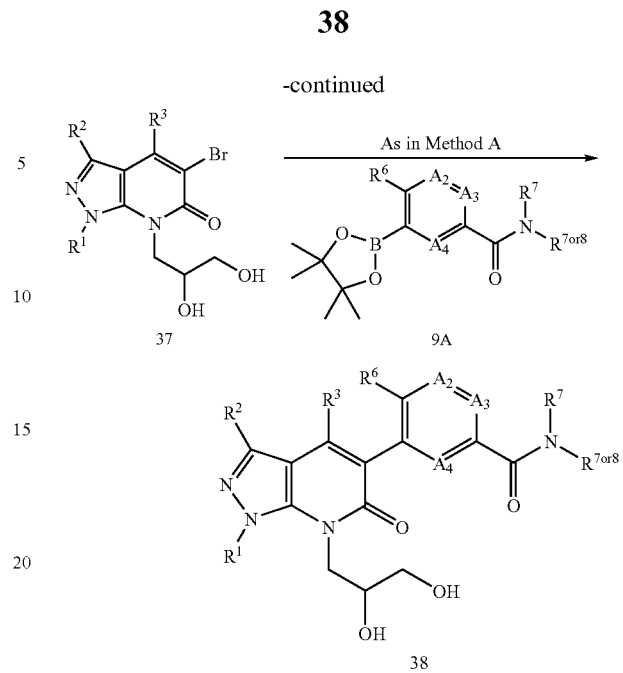

Substituted pyrazolo-pyridinethiones 29A may be made by the method generally described in Scheme 7, also designated herein as Method H, In method H, the ketone of the bromo-pyrazolo-pyridinone intermediate 24 can be converted to the corresponding thio-ketone 24A using conventional methods, such as with Lawessen's Reagent under suitable conditions. Thio-ketone 24A can be reacted with a boronate 9A (as shown in Method A, scheme 1) under suitable Suzuki or Suzuki-like coupling conditions to afford the coupled adduct 29A.

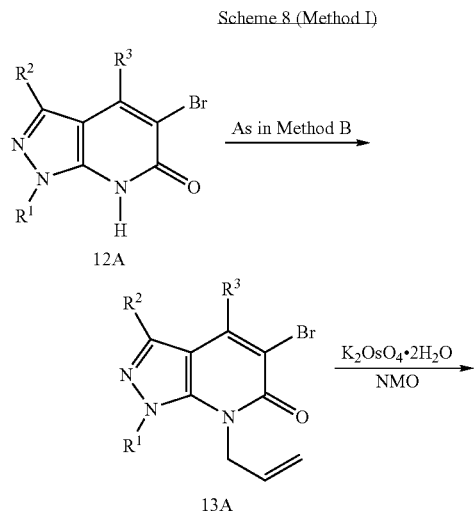

Substituted pyrazolo-pyridinones 38 may be made by the method generally described in Scheme 8, also designated herein as Method I. In method I, the amide nitrogen of the bromo-pyrazolo-pyridinone intermediate 12A can be functionalized or substituted using a method described in scheme 2, to install an allyl group (as shown) for example, and afford intermediate 13A. The allyl group of 13A may further be functionalized, such as oxidized (as shown) to the corresponding dihydroxide intermediate 37 using conventional oxidizing agents, such as osmium as shown. Intermediate 37 can be reacted with a boronate 9A (as shown in Method A, scheme 1) under suitable Suzuki or Suzuki-like coupling conditions to afford the coupled adduct 38. This method provides an effective process for varying the $R^4$ group in compounds of Formulas I, I-B and I-C.

Various other linker $R^5$ groups are within the scope of the present invention. Such other linkers may be made using the general methods described in scheme 9 below. As illustrate in scheme 9, desirable $R^1$ and $R^8$ groups are shown as a ring designated as ring A. However, the present invention is not so limited, and it is intended that what is depicted as "ring A" in scheme 9 should be read to also include non cyclic moieties attached to linker $R^5$, as described in Formulas I, I-B and I-C herein.

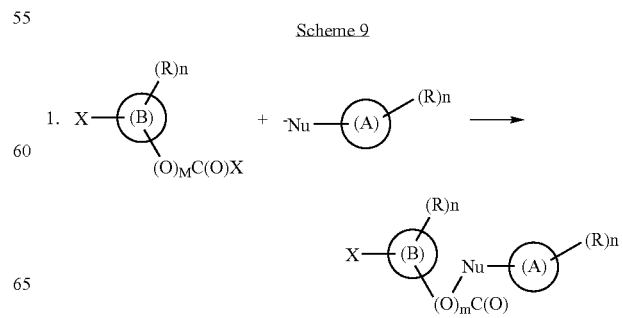

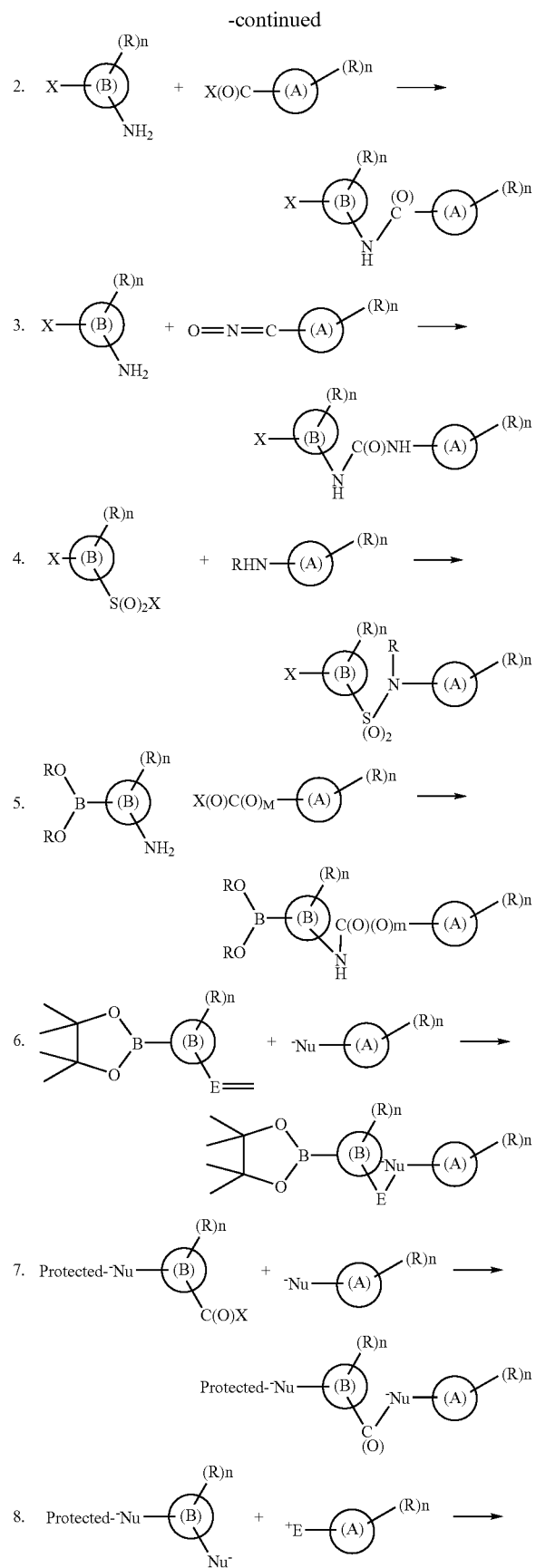
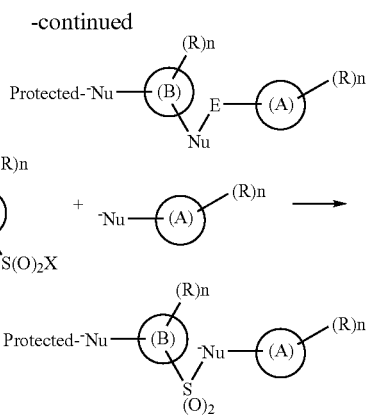

The B ring, as illustrated in scheme 9, is substituted by a linker group $R^5$. The $R^5$ linker group, including an amino, a carboxyl, a sulfonyl, an amido or a urea linker, as defined herein in Formulas I, I-B and I-C, connect various substitutions, including $R^7$ non-cyclic moieties or $R^7$ and $R^8$ cyclic rings (generally designated and referred to in Scheme 10, and throughout the specification, as the "A" group or "A" ring) to the "B" ring. This linker may be attached by various coupling methods as described in Scheme 9. Each of the nine sub-schemes, numbered 1-9 above and described below, utilize the following meanings for $(R)_n$, X, $Nu^-$, $E^+$ and m: $(R)_n$ refers to n number of $R^6$, $R^7$ and $R^8$ substitutions wherein n is an integer from 0-5; X refers generally to a "leaving group" (also referred to herein as "LG") such as a halide (bromine, chlorine, iodine or fluorine), alkylsulfonate and other known groups (also see definitions herein); $Nu^-$ refers generally to a nucleophilic species such as a primary or secondary amine, an oxygen, a sulfur or a anionic carbon species—examples of nucleophiles include, without limitation, amines, hydroxides, alkoxides and the like; E+refers generally to an electrophilic species, such as the carbon atom of a carbonyl, which is susceptible to nucleophilic attack or readily eliminates—examples of suitable electrophilic carbonyl species include, without limitation, acid halides, mixed anhydrides, aldehydes, carbamoyl-chlorides, sulfonyl chlorides, acids activated with activating reagents such as TBTU, HBTU, HATU, HOBT, BOP, PyBOP and carbodiimides (DCC, EDC, CDI and the like), and other electrophilic species including halides, isocyanates, daizonium ions and the like; and m is either 0 or 1.

The coupling of ring B to A, as shown as products in sub-schemes 1-9, can be brought about using various conventional methods to link ring B and A together. For example, an amide or a sulfonamide linkage, as shown in sub-schemes 2 and 4, and 7 and 9 where the Nu– is an amine, respectively, can be made utilizing an amine on either the B or A groups and an acid chloride or sulfonyl chloride on the other of either the B or A groups. The reaction proceeds generally in the presence of a suitable solvent and/or base. Suitable solvents include, without limitation, generally non-nucleophilic, anhydrous solvents such as toluene, $CH_2Cl_2$, THF, DMF, DMSO, N,N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates as illustrated in sub-schemes 5 and I where Nu– is an amine, anhydrides as illustrated in sub-scheme 1 where Nu– is an oxygen, reverse amides as generally illustrated in sub-scheme 8 where Nu– is an amine and E+ is an acid chloride, ureas as illustrated in sub-scheme 3, thioamides and thioureas where the respective carbonyl oxygen is a sulfur, thiocarbamates where the respective carbonyl oxygen and/or carbamate oxygen is a sulfur, and the like. While the above methods are so described, they are not exhaustive, and other methods for linking groups A and B together may be utilized as appreciated by those skilled in the art.

Although sub-schemes 1-9 are illustrated as having the nucleophilic and electrophilic coupling groups, such as the amino group and acid chloride groups illustrated in sub-scheme 2, directly attached to the substrate, either the A group or B ring, in question, the invention is not so limited. It is contemplated herein that these nucleophilic and/or electrophilic coupling groups may be tethered from their respective ring. For example, the amine group on the B ring, and/or the acid halide group on the A group or ring, as illustrated in sub-scheme 2, may be removed from direct attachment to the ring by a one or more atom spacer, such as by a methylene, ethylene spacer or the like. As appreciated by those skilled in the art, such spacer may or may not affect the coupling reactions described above, and accordingly, such reaction conditions may need to be modified to effect the desired transformation.

The coupling methods described in sub-schemes 1-9 of scheme 6 are also applicable for coupling desired A groups or rings to desired pyrazolo-pyridinone-B ring intermediates, such as to substituted B ring carboxylic acids (Example 2) to synthesize desired compounds of Formulas I, I-B and I-C. For example, a desirably substituted pyrazolo-pyridinone-benzoic acid maybe reacted with a desirably substituted primary or secondary, amine, such as an NHR$^7$R$^7$ or NHR$^7$R$^8$ group in the presence of a suitable solvent and a known coupling reagent, such as TBTU, HATU, CDI or others, to prepare the desired A-B amide bond, and the final compound of Formulas I or I-B.

Note that the B-A moiety is connected through a linker "L". "L" may be any linker generally defined by the R$^5$ groups in Formulas I, I-B and I-C, and particularly, it includes, without limitation, an amide, a urea, a thiourea, a thioamide, a carbamate, an anhydride, a sulfonamide and the like, allowing for spacer atoms either between ring B and L and/or between ring or group A and L, as described in Scheme 6 above.

To enhance the understanding and appreciation of the present invention, the following specific examples (starting reagents, intermediates and compounds of Formulas I, I-B and I-C) and methods of making compounds of the invention are set forth. It should be appreciated that the above general methods and specific examples below are merely for illustrative purposes only and are not to be construed as limiting the scope of this invention in any manner. The following analytical methods were used to purify and/or characterize the compounds, and intermediates, described in the examples below.

Analytical Methods:

Unless otherwise indicated, all HPLC analyses were run on a Agilent Model 1100 system with an Agilent Technologies Zorbax SB-C$_8$(5µ) reverse phase column (4.6×150 mm; Part no. 883975-906) run at 30° C. with a flow rate of about 1.50 mL/min. The mobile phase used solvent A (H$_2$O/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Method:

Samples were run on an Agilent model-1100 LC-MSD system with an Phenomenex Synergi MAX-RP (4.0µ) reverse phase column (2×50 mm) at 40° C. The flow rate was constraint and ranged from about 0.75 mL/min to about 1.0 mL/min.

The mobile phase used a mixture of solvent A (H$_2$O/0.1% TFA) and solvent B (ACN/0.1% TFA) with a5 min time period for a gradient from 10% to 100% solvent B. The gradient was followed by a 0.5 min period to return to 10% solvent B and a 1.5 min 10% solvent B re-equilibration (flush) of the column.

Preparative HPLC Method:

Where indicated, compounds of interest were purified via reverse phase HPLC using a Gilson workstation utilizing one of the following two columns and methods: (A) Using a 50×100 mm column (Waters, Exterra, C18, 5 microns) at 50 mL/min. The mobile phase used was a mixture of solvent A (H$_2$O/10 mM ammonium carbonate at pH about 10, adjusted with conc. NH$_4$OH) and solvent B (85:15 ACN/water, 10 mM ammonium carbonate at pH of about 10 adjusted with conc. NH$_4$OH). Each purification run utilized a 10 minute gradient from 40% to 100% solvent B followed by a 5 minute flow of 100% solvent B. The gradient was followed by a 2 min return to 40% solvent B. (B) Using a 20×50 mm column at 20 mL/min. The mobile phase used was a mixture of solvent A (H$_2$O/0.1% TFA) and solvent B (ACN/0.1% TFA) with a 10 min gradient from 5% to 100% solvent B. The gradient is followed by a 2 min return to 5% ACN.

Proton NMR Spectra:

Unless otherwise indicated, all $^1$H NMR spectra were run on a Varian series Mercury 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

Example 1 (via Method A)

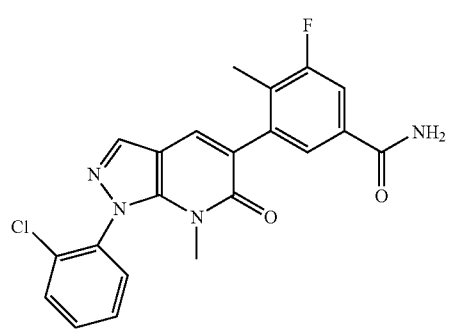

Synthesis of 3-(1-(2-chlorophenyl)-7-methyl-6-oxo-6,7-dihydro-1H-pyrazolo[3,4 b]pyridin-5-yl)-5-fluoro-4-methylbenzamide

Step 1A: Synthesis of 5-Amino-1-(2-chlorophenyl)-1H-pyrazole-4-carbaldehyde At RT, 2-(ethoxymethylene)malononitrile (5.77 g, 47.2 mmol) was added in portions to a stirred suspension of 1-(2-chlorophenyl)hydrazine hydrochloride (8.05 g, 45.0 mmol) and TEA (6.58 ml, 47.2 mmol) in absolute EtOH (56 mL). The mixture was heated to reflux for 1 h. The volatile solvents were removed under reduced pressure. The brown reside was dissolved in EtOAc, washed with water followed by saturated NaHCO$_3$ solution. The organic layer was dried over sodium sulfate, filtered, and concentrated under reduced pressure to obtain 5-amino-1-(2-chlorophenyl)-1H-pyrazole-4-carbonitrile as a rusty crystalline solid. MS (ESI, pos.ion) m/z: 219.0 (M+1).

Step 1B: To a solution of 5-amino-1-(2-chlorophenyl)-1H-pyrazole-4-carbonitrile (2.0 g, 9.1 mmol) in glacial acetic acid (12.0 mL) was added Raney 2400 Nickel (1.1 g, 18 mmol). The mixture was hydrogenated at RT with a balloon overnight. The reaction mixture was filtered through a short plug of Celite, washing with water then wet EtOAc. The water layer was separated and extracted with EtOAc. The combined EtOAc layers were washed with 1.0 N NaOH followed by brine, dried over MgSO$_4$, filtered and concentrated. The brown residue was loaded on an ISCO 40 g column (eluted with 25-65% EtOAc in Hexanes) to afford the title compound, 5-amino-1-(2-chlorophenyl)-1H-pyrazole-4-carbaldehyde, as a tan crystalline solid. MS (ESI, pos.ion) m/z: 220.0 (M+1).

Step 2: Synthesis of 1-(2-Chlorophenyl)-1H-pyrazolo[3,4-b]pyridin-6(7H)-one At −35° C., KHMDS (8.03 mL of 0.5 M in toluene, 4.01 mmol) was added to a slurry of methyl p,p-bis(2,2,2-trifluoroethyl)-phosphonoacetate (1.21 g, 3.82 mmol) and 18-crown-6 (506 mg, 1.91 mmol) in 3.0 mL of THF. After the resulting mixture was stirred at −35° C. for 10 min, a solution of 5-amino-1-(2-chlorophenyl)-1H-pyrazole-4-carbaldehyde (424 mg, 1.91 mmol) in THF (1.5 mL+1.5 mL rinsing) was added in via a syringe. The reaction mixture was slowly warmed to RT overnight, quenched with saturated NH$_4$Cl, and extracted with EtOAc twice. The combined EtOAc layers were dried and concentrated to dryness. The resulting brown residue in THF (3.0 mL) at RT was treated with KHMDS (12 mL of 0.5 M in toluene, 6.0 mmol) and heated at 70° C. in an oil bath for 3 h. After the reaction mixture was cooled to RT, it was treated with saturated NH$_4$Cl, and extracted with EtOAc twice. The combined EtOAc layers were dried and concentrated. The brown residue was loaded on an ISCO 12 g column (eluted with 25-65% EtOAc in Hexanes) to give the title compound (352 mg) as a yellow amorphous solid. MS (ESI, pos.ion) m/z: 246.0 (M+1).

Step 3: Synthesis of 1-(2-Chlorophenyl)-7-methyl-1H-pyrazolo[3,4-b]pyridin-6(7H)-one At RT, 1-(2-chlorophenyl)-1H-pyrazolo[3,4-b]pyridin-6(7H)-one (542 mg, 2.20 mmol) in 4.0 mL of DMF was treated with anhydrous potassium carbonate (610 mg, 4.40 mmol) followed by iodomethane (0.2 mL, 3.21 mol). After the mixture was stirred at RT overnight, it was filtered through a fritted funnel, and rinsed with EtOAc. The filtrate was concentrated and the residue was purified on an ISCO 40 g column (eluted with 25-90% EtOAc in Hexanes) to provide: 1) 1-(2-chlorophenyl)-6-methoxy-1H-pyrazolo[3,4-b]pyridine (150 mg) as a yellow thick oil, MS (ESI, pos.ion) m/z: 260.1 (M+1); 2) 1-(2-chlorophenyl)-7-methyl-1H-pyrazolo[3,4-b]pyridin-6(7H)-one (320 mg) as a light yellow crystalline solid, MS (ESI, pos.ion) m/z: 260.1 (M+1).

Step 4: Synthesis of 5-bromo-1-(2-chlorophenyl)-7-methyl-1H-pyrazolo[3,4-b]pyridin-6(7H)-one At RT, bromine (206 mg, 1.29 mmol) was added to a solution of 1(2-chlorophenyl)-7-methyl-1H-pyrazolo[3,4-b]pyridin-6(7H)-one (319 mg, 1.23 mmol) in 1.5 mL of glacial acetic acid. After stirring at RT for 30 min, it was diluted with water and stirred for 5 min. The precipitated white solid was filtered off and rinsed with water, collected and dried to afford 5-bromo-1-(2-chlorophenyl)-7-methyl-1H-pyrazolo[3,4-b]pyridin-6(7H)-one (323 mg). The filtrate was extracted three times with EtOAc. The combined EtOAc layers were washed with 2 N NaOH followed by brine, dried and concentrated to afford additional 5-bromo-1-(2-chlorophenyl)-7-methyl-1H-pyrazolo[3,4-b]pyridin-6(7H)-one (82 mg). The crude material was used without further purification. MS (ESI, pos.ion) m/z: 338.0/340.0 (M+1).

Step 5: Synthesis of 3-(1-(2-chlorophenyl)-7-methyl-6-oxo-6,7-dihydro-1H-pyrazolo[3,4-b]pyridin-5-yl)-5-fluoro-4-methylbenzamide A mixture of 3-fluoro-4-methyl-5-(4,4,5,5-tetramethyl-1,3,2-dioxaborolan-2-yl)benzamide (118 mg, 422 μmol), 5-bromo-1-(2-chlorophenyl)-7-methyl-1H-pyrazolo[3,4-b]pyridin-6(7H)-one (130 mg, 384 μmol), Pd(PPh$_3$)$_4$ (0.016 mmol, 19 mg), and sodium carbonate (2 M) (0.576 ml, 1.15 μmol) in 2.0 mL of dioxane in a sealed tube was heated in a microwave at 125° C. for 25 min. The mixture was treated with 2 mL of 1 N NaOH solution, extracted with 2×5 mL of EtOAc. The combined organic phases were washed with 2 mL of brine, dried and concentrated. The brown residue was loaded on an ISCO 12 g column (eluting with a gradient of 1-6% MeOH in DCM) to provide the title compound (140 mg) as an off white crystalline solid. MS (ESI, pos.ion) m/z: 411.2 (M+1).

Example 2 (via Method B)

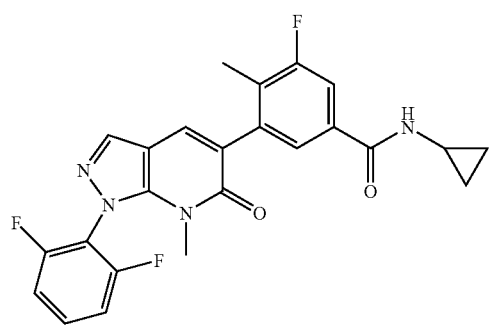

Synthesis of N-cyclopropyl-3-(1-(2,6-difluorophenyl)-7-methyl-6-oxo-6,7-dihydro-1H-pyrazolo[3,4-b]pyridin-5-yl)-5-fluoro-4-methylbenzamide Step 1: Synthesis of Ethyl 1-(2,6-difluorophenyl)-6-oxo-6,7-dihydro-1H-pyrazolo[3,4-b]pyridine-5-carboxylate In a 500 mL round-bottomed flask was added 5-amino-1-(2,6-difluorophenyl)-1H-pyrazole-4-carbaldehyde (7.77 g, 35 mmol; prepared in a fashion similar to that described for 5-amino-1-(2-chlorophenyl)-1H-pyrazole-4-carbaldehyde in Example 1 above) followed by ethanol (100 ml, 35 mmol). To the solution was added diethyl malonate (11 ml, 70 mmol) and piperidine (3.4 ml, 35 mmol) and the mixture was heated to 75° C. overnight. The reaction mixture was concentrated under reduced pressure and the brown residue was treated with 200 mL of a 1:1 solution of EtOAc:Hexanes. The precipitated solid was then filtered through a sintered glass frit and rinsed with hexanes. It was dried under high vacuum to afford the title compound (11.13 g, 100% yield) as a beige crystalline solid. MS (ESI, pos.ion) m/z: 306.0 (M+1).

Step 2: 5-Bromo-1-(2,6-difluorophenyl)-1H-pyrazolo[3,4-b]pyridin-6(7H)-one

Ethyl 1-(2,6-difluorophenyl)-6-oxo-6,7-dihydro-1H-pyrazolo[3,4-b]pyridine-5-carboxylate (9.40 g, 0.29 mmol) was treated with 80 mL $CH_3CN$ and 80 mL water and lithium hydroxide monohydrate (3.10 g, 74 mmol). The resulting suspension was then heated to 90° C. for 1 h. The solution was allowed to cool to 35° C. and treated with N-bromosuccimide (5.20 g, 29 mmol) in one portion. It was allowed to stir for 1 h at RT then treated with another equiv. of N-bromosuccimide (5.20 g, 29 mmol) in one portion. After stirring for an additional 1 h at RT, it was treated with a saturated solution of $NaHCO_3$ and extracted with 2×150 mL EtOAc. The combined organic solution was washed with brine, dried over $MgSO_4$, filtered and concentrated to afford the title compound (8.31 g) as an orange foam in ca. 90% purity. No further purification was carried out prior to use in the next step. MS (ESI, pos.ion) m/z: 326.0/327.9 (M+1). For a related reference, see: Chowdhury, S.; Roy, S. *J. Org. Chem.* 1997, 62, 199-200.

Step 3: 5-Bromo-1-(2,6-difluorophenyl)-7-methyl-1H-pyrazolo[3,4-b]pyridin-6(7H)-one 5-Bromo-1-(2,6-difluorophenyl)-1H-pyrazolo[3,4-b]pyridin-6(7H)-one (11.3 g, 34.7 mmol) in DME (78 mL) and DMF (7.7 mL) was cooled to 0° C. under argon. NaH (1.24 g of 95% wt., 49 mmol) was then added in small portions and the solution was allowed to stir at 0° C. for 10 min. Finely ground lithium bromide (8.83 g, 102 mmol) was then added and the solution stirred at RT for 20 min at which point MeI (4.37 ml, 68.9 mmol) was added. The suspension was heated at 40° C. for 16 h then cooled to RT. The reaction mixture was quenched with water and extracted with EtOAc (3×100 mL). The combined organic solution was washed with 2×50 mL brine, dried over $MgSO_4$, filtered and concentrated. The resulting crude solid was then suspended in 300 mL of 1:1 solution of EtOAc:Hexanes with stirring over 30 min. The solution was then allowed to precipitate in the freezer for 2 h. The resulting solid was then collected by filtration washing with MTBE affording 5-bromo-1-(2,6-difluorophenyl)-7-methyl-1H-pyrazolo[3,4-b]pyridin-6(7H)-one (5.27 g) in >95% purity as a beige solid. The mother liquor was then concentrated to ca. 15 ml in vacuo (rotary evaporator) and treated with 50 mL of MTBE and again chilled in the freezer overnight. The resulting solid was collected by filtration and washing with MTBE to afford a second crop of 5-bromo-1-(2,6-difluorophenyl)-7-methyl-1H-pyrazolo[3,4-b]pyridin-6(7H)-one (1.54 g) in ca. 95% purity. MS (ESI, pos.ion) m/z: 340.0/342.0 (M+1). For a related reference, see: Liu, H.; Ko, S.-B.; Josien, H.; Curran, D. P. *Tetrahedron Lett.* 1995, 36, 8917-8920.

Step 4: N-cyclopropyl-3-(1-(2,6-difluorophenyl)-7-methyl-6-oxo-6,7-dihydro-1H-pyrazolo[3,4-b]pyridin-5-yl)-5-fluoro-4-methylbenzamide A mixture of 5-bromo-1-(2,6-difluorophenyl)-7-methyl-1H-pyrazolo[3,4-b]pyridin-6(7H)-one (110 mg, 0.32 mmol), N-cyclopropyl-3-fluoro-4-methyl-5-(4,4,5,5-tetramethyl-1,3,2-dioxaborolan-2-yl)benzamide (122 mg, 0.38 mmol) and 15 mg of $Pd(PPh_3)_4$ in 2.0 mL dioxane and 0.8 mL of 1 M $Na_2CO_3$ in a sealed glass tube was heated at 130° C. for 30 min. The reaction mixture was diluted in EtOAc, washed with 1 N NaOH solution. The organic phase was dried over $MgSO_4$, filtered and concentrated. Purification of the brown residue on an ISCO 12 g column (40-80% EtOAc in Hexanes) afforded the title compound (96 mg) as an off white amorphous solid. MS (ESI, pos.ion) m/z: 453.1 (M+1).

Example 3 (via Method D)

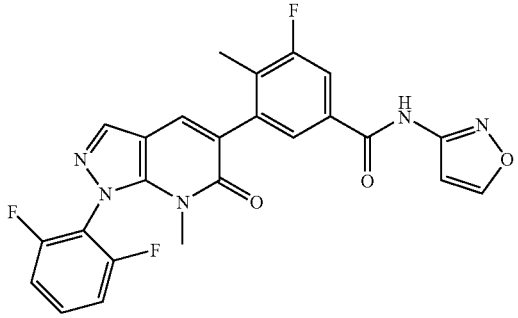

Synthesis of 3-(1-(2,6-Difluorophenyl)-7-methyl-6-oxo-6,7-dihydro-1H-pyrazolo[3,4-b]pyridin-5-yl)-5-fluoro-N-(isoxazol-3-yl)-4-methylbenzamide Step 1: 3-(1-(2,6-Difluorophenyl)-7-methyl-6-oxo-6,7-dihydro-1H-pyrazolo[3,4-b]pyridin-5-yl)-5-fluoro-4-methylbenzoic acid In a 25 mL sealed glass tube, a mixture of tetrakis(triphenylphosphine)palladium(0) (42 mg, 37 μmol), 3-borono-5-fluoro-4-methylbenzoic acid (218 mg, 1101 μmol), and 5-bromo-1-(2,6-difluorophenyl)-7-methyl-1H-pyrazolo[3,4-b]pyridin-6(7H)-one (312 mg, 917 μmol) in 4.6 mL of dioxane and 1.0 M solution of sodium carbonate (2.3 mL, 2.3 mmol) was heated in a microwave at 130° C. for 30 min. The reaction mixture was treated with 15 mL of ether and washed with 5 mL of 2 N NaOH, The ether layer was discarded. The aqueous extracts were acidified to pH 4 with 5 N HCl and extracted with 3×25 mL EtOAc. The combined EtOAc layers were dried over $MgSO_4$, filtered and concentrated in vacuo (rotovap) affording the title compound (296 mg) as a viscous oil which solidified to an off-white amorphous solid under vacuum overnight. MS (ESI, pos.ion) m/z: 414.0 (M+1).

Step 2: 3-(1-(2,6-Difluorophenyl)-7-methyl-6-oxo-6,7-dihydro-1H-pyrazolo[3,4-b]pyridin-5-yl-5-fluoro-N-(isoxazol-3-yl)-4-methylbenzamide In a 100 mL round-bottom flask was weighed 3-(1-(2,6-difluorophenyl)-7-methyl-6-oxo-6,7-dihydro-1H-pyrazolo[3,4-b]pyridin-5-yl)-5-fluoro-4-methylbenzoic acid (295 mg, 0.714 mmol) followed by SOCl$_2$ (5.00 mL, 6.85 mmol) under nitrogen. It was heated to 95° C. for 3 h then cooled to RT and the excess thionyl chloride removed in vacuo (rotovap). The residue was then treated with pyridine (3.00 mL) at 0° C. and isoxazol-3-amine (1.00 mL, 1.42 mmol) was added. It was heated at 45° C. for 2 h. The reaction mixture was then concentrated in vacuo (rotovap) and the crude residue was dissolved in DCM, washed sequentially with water, 1 N NaOH and brine. The DCM solution was dried and concentrated. The brown residue was purified on the ISCO (40 g column, eluted with 20-80% EtOAc:Hexanes) affording the title compound (87.9 mg) as a white amorphous solid. MS (ESI, pos.ion) m/z: 480.0 (M+1).

Example 4 (via Method E)

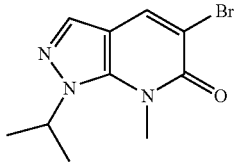

Synthesis of 5Bromo-1-isopropyl-7-methyl-1H-pyrazolo[3,4b]pyridin-6(7H)-one

Step 1: 5-Bromo-7-methyl-1H-pyrazolo[3,4-b]pyridin-6(7H)-one acetic acid adduct

1-Tert-butyl-7-methyl-1H-pyrazolo[3,4-b]pyridin-6(7H)-one was prepared in a fashion similar to that described for 1-(2-fluorophenyl)-7-methyl-1H-pyrazolo[3,4-b]pyridin-6(7H)-one (155 mg) as a light yellow crystalline solid (Example 1—step 3).

To a solution of 1-tert-butyl-7-methyl-1H-pyrazolo[3,4-b]pyridin-6(7H)-one (240 mg, 1.17 mmol) in glacial AcOH (5.5 mL) at RT was added bromine (0.060 mL, 1169 µmol) slowly. An orange suspension resulted and it was allowed to stir at RT for 1 h. 5.0 mL water was added, and the pH was adjusted to pH 6 using 5 N NaOH, It was extracted with 2×50 mL EtOAc, dried over MgSO$_4$, filtered and concentrated in vacuo (rotovap) affording 5-bromo-7-methyl-1H-pyrazolo[3,4-b]pyridin-6(7H)-one acetic acid adduct (305 mg) as a beige solid. MS (ESI, pos.ion) m/z: 227.9 (M+1) and 229.9 (M+1). This crude product was used in the next step.

Step 2: 5-Bromo-1-isopropyl-7-methyl-1H-pyrazolo[3,4-b]pyridin-6(7H)-one

At RT, to a solution of 5-bromo-7-methyl-1H-pyrazolo[3,4-b]pyridin-6(7H)-one acetic acid adduct (202 mg, 0.701 mmol) in THF (10 mL) was treated with potassium carbonate (290 mg, 2.10 mmol) and 2-iodopropane (0.50 mL, 5.0 mmol). It was heated to reflux for 48 h. The reaction mixture was then treated with water and extracted 2×20 mL EtOAc, dried over MgSO$_4$, filtered and concentrated in vacuo (rotovap). The crude residue was purified on the ISCO (12 g column, 25-90% EtOAc:Hexanes) affording the title compound (88 mg) as a white amorphous solid in >95% purity. MS (ESI, pos.ion) m/z: 270.0/272.0 (M+1).

These detailed descriptions of Examples fall within the scope, and serve to exemplify the above-described General Synthetic Procedures which form part of the invention. These detailed descriptions are not intended as a restriction on the scope of the invention.

The following Examples in Table 1 will further assist in understanding and appreciating the invention. The compounds of examples 6-34 were made in accordance with exemplary methods A, B, D and E which correspond to above Examples 1-4, respectively, and more generally to schemes 1-4. The compound examples were named according to the ACD naming convention, as associated with ISIS software. The mass spectral data is recorded M+H$^+$, which is the positive ion as measured by an electrospray ionization method. The biological assay data is provided for those exemplary compounds in Table 1 which were tested in, and data calculated from, the human whole blood and cellular assays. Not every compound example was run in the assays at the time of filing of this application, and accordingly no data is provided in the Table.

TABLE 1

| Ex. No | Name | MS (M + H+) | Method | WB TNF/IL8 IC50 (nM) | p38a IC50 (nM) |
|---|---|---|---|---|---|
| 6 | N-cyclopropyl-3-(7-ethyl-1-(2-fluorophenyl)-6-oxo-6,7-dihydro-1H-pyrazolo[3,4-b]pyridin-5-yl)-5-fluoro-4-methylbenzamide | 449.2 | A | 1.2 | 2.5 |
| 2 | N-cyclopropyl-3-(1-(2,6-difluorophenyl)-7-methyl-6-oxo-6,7-dihydro-1H-pyrazolo[3,4-b]pyridin-5-yl)-5-fluoro-4-methylbenzamide | 453.0 | B | 1.5 | 1.8 |
| 7 | N-cyclopropyl-3-(1-(2,6-difluorophenyl)-7-methyl-6-oxo-6,7-dihydro-1H-pyrazolo[3,4-b]pyridin-5-yl)-4-methylbenzamide | 435.1 | B | 1.3 | 2.5 |
| 8 | 3-(1-(2-chlorophenyl)-7-methyl-6-oxo-6,7-dihydro-1H-pyrazolo[3,4-b]pyridin-5-yl)-N-cyclopropyl-5-fluoro-4-methylbenzamide | 451.1 | A | 2.5 | 2.3 |

TABLE 1-continued

| Ex. No | Name | MS (M + H+) | Method | WB TNF/IL8 IC50 (nM) | p38a IC50 (nM) |
|---|---|---|---|---|---|
| 9 | N-cyclopropyl-3-fluoro-5-(1-(2-fluorophenyl)-7-methyl-6-oxo-6,7-dihydro-1H-pyrazolo[3,4-b]pyridin-5-yl)-4-methylbenzamide | 435.1 | A | 1.7 | 2.2 |
| 10 | 3-(1-(2,6-difluorophenyl)-7-methyl-6-oxo-6,7-dihydro-1H-pyrazolo[3,4-b]pyridin-5-yl)-4-methyl-N-(1-methyl-1H-pyrazol-5-yl)benzamide | 475.1 | B | 2.2 | 2.9 |
| 11 | N-cyclopropyl-3-(1-(2,4-difluorophenyl)-7-methyl-6-oxo-6,7-dihydro-1H-pyrazolo[3,4-b]pyridin-5-yl)-5-fluoro-4-methylbenzamide | 453.0 | B | 2.0 | 2.6 |
| 12 | 3-(1-(2-chlorophenyl)-7-methyl-6-oxo-6,7-dihydro-1H-pyrazolo[3,4-b]pyridin-5-yl)-N-cyclopropyl-4-methylbenzamide | 433.2 | A | 8.2 | 1.8 |
| 13 | N-cyclopropyl-3-(1-(2,4-difluorophenyl)-7-methyl-6-oxo-6,7-dihydro-1H-pyrazolo[3,4-b]pyridin-5-yl)-4-methylbenzamide | 435.1 | B | 2.8 | 5.2 |
| 14 | N-cyclopropyl-4-methyl-3-(7-methyl-1-(2-methylphenyl)-6-oxo-6,7-dihydro-1H-pyrazolo[3,4-b]pyridin-5-yl)benzamide | 413.1 | B | 10.3 | 4.2 |
| 1 | 3-(1-(2-chlorophenyl)-7-methyl-6-oxo-6,7-dihydro-1H-pyrazolo[3,4-b]pyridin-5-yl)-5-fluoro-4-methylbenzamide | 411.1 | A | 18.0 | 2.3 |
| 15 | N-cyclopropyl-3-fluoro-4-methyl-5-(7-methyl-1-(2-methylphenyl)-6-oxo-6,7-dihydro-1H-pyrazolo[3,4-b]pyridin-5-yl)benzamide | 431.1 | B | 1.7 | 5.2 |
| 16 | N-(3-(1-(2,4-difluorophenyl)-7-methyl-6-oxo-6,7-dihydro-1H-pyrazolo[3,4-b]pyridin-5-yl)-4-methylphenyl)cyclopropanecarboxamide | 435.1 | B | 73.6 | |
| 17 | N-cyclopropyl-3-fluoro-4-methyl-5-(7-methyl-1-(1-methylethyl)-6-oxo-6,7-dihydro-1H-pyrazolo[3,4-b]pyridin-5-yl)benzamide | 383.1 | E | 35.3 | |
| 18 | 3-(1-(2,6-difluorophenyl)-7-methyl-6-oxo-6,7-dihydro-1H-pyrazolo[3,4-b]pyridin-5-yl)-N-3-isoxazolyl-4-methylbenzamide | 462 | D | 1.3 | 3 |
| 3 | 3-(1-(2,6-difluorophenyl)-7-methyl-6-oxo-6,7-dihydro-1H-pyrazolo[3,4-b]pyridin-5-yl)-5-fluoro-N-3-isoxazolyl-4-methylbenzamide | 480.0 | D | 0.8 | 2.4 |
| 19 | N-cyclopropyl-4-(1-(2,6-difluorophenyl)-7-methyl-6-oxo-6,7-dihydro-1H-pyrazolo[3,4-b]pyridin-5-yl)-5-methyl-2-pyridinecarboxamide | 436.1 | B | 13.3 | 18 |
| 20 | 4-chloro-N-cyclopropyl-3-(1-(2,6-difluorophenyl)-7-methyl-6-oxo-6,7-dihydro-1H-pyrazolo[3,4-b]pyridin-5-yl)benzamide | 455.2 | B | 4.0 | 2.5 |
| 21 | 3-(1-(2,6-difluorophenyl)-7-methyl-6-oxo-6,7-dihydro-1H-pyrazolo[3,4-b]pyridin-5-yl)-5-fluoro-4-methyl-N-(1-methylethyl)benzamide | 455.1 | B | 26.3 | 7 |
| 22 | 3-(1-(2,6-difluorophenyl)-7-methyl-6-oxo-6,7-dihydro-1H-pyrazolo[3,4-b]pyridin-5-yl)-5-fluoro-N,4-dimethylbenzamide | 427 | B | 9.1 | 6.2 |
| 23 | N-cyclopropyl-3-(1-(2,5-difluorophenyl)-7-methyl-6-oxo-6,7-dihydro-1H-pyrazolo[3,4-b]pyridin-5-yl)-5-fluoro-4-methylbenzamide | 453 | B | 1.3 | 3.9 |
| 24 | N-cyclopropyl-3-(1-(2,5-difluorophenyl)-7-methyl-6-oxo-6,7-dihydro-1H-pyrazolo[3,4-b]pyridin-5-yl)-4-methylbenzamide | 435.1 | B | 2.3 | 6.2 |
| 25 | 3-(1-(2,5-difluorophenyl)-7-methyl-6-oxo-6,7-dihydro-1H-pyrazolo[3,4-b]pyridin-5-yl)-4-methyl-N-(1-methylcyclopropyl)benzamide | 449 | B | 24.1 | 1.1 |
| 26 | 3-(1-(2,5-difluorophenyl)-7-methyl-6-oxo-6,7-dihydro-1H-pyrazolo[3,4-b]pyridin-5-yl)-N-3-isoxazolyl-4-methylbenzamide | 462 | D | 1.4 | 2.3 |
| 27 | 3-(1-(2,4-difluorophenyl)-7-methyl-6-oxo-6,7-dihydro-1H-pyrazolo[3,4-b]pyridin-5-yl)-N-3-isoxazolyl-4-methylbenzamide | 462 | D | 1.7 | 2.4 |
| 28 | 3-(1-(2,6-difluorophenyl)-7-methyl-6-oxo-6,7-dihydro-1H-pyrazolo[3,4-b]pyridin-5-yl)-4-methyl-N-1,3-thiazol-2-ylbenzamide | 478 | D | 16.7 | 1.1 |
| 29 | 4-chloro-N-cyclopropyl-3-(1-(2,5-difluorophenyl)-7-methyl-6-oxo-6,7-dihydro-1H-pyrazolo[3,4-b]pyridin-5-yl)benzamide | 455.2 | B | 13.6 | |

TABLE 1-continued

| Ex. No | Name | MS (M + H+) | Method | WB TNF/IL8 IC50 (nM) | p38a IC50 (nM) |
|---|---|---|---|---|---|
| 30 | 3-(1-(2,6-difluorophenyl)-7-methyl-6-oxo-6,7-dihydro-1H-pyrazolo[3,4-b]pyridin-5-yl)-4-methyl-N-(1-methylcyclopropyl)benzamide | 449 | B | 6.3 | |
| 31 | 3-(1-(2,6-difluorophenyl)-7-methyl-6-oxo-6,7-dihydro-1H-pyrazolo[3,4-b]pyridin-5-yl)-5-fluoro-4-methylbenzamide | 413 | A | 1.6 | 1 |

Example 32 (via Method F)

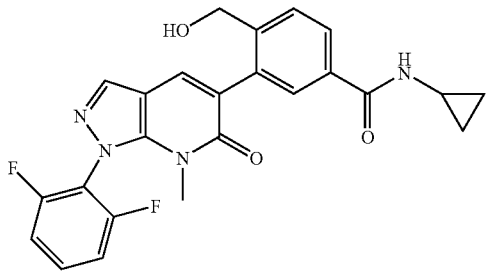

Synthesis of N-cyclopropyl-3-(1-(2,6-difluorophenyl)-7-methyl-6-oxo-6,7-dihydro-1H-pyrazolo[3,4b]pyridin-5-yl-4(hydroxymethyl)benzamide Step 1A: Synthesis of methyl 3-bromo-4-(bromomethyl)benzoate Methyl 3-bromo-4-methylbenzoate (6.56 g, 28.64 mmol), carbon tetrachloride (100 mL), NBS (6.07 g, 34.10 mmol) and AIBN (150 mg, 0.91 mmol) were heated at reflux for 18 h. The reaction mixture was cooled and diluted with DCM (200 mL) and water (100 ml) and washed with 5% NaHCO$_3$ saturated solution (50 mL), dried over MgSO$_4$, filtered and concentrated under reduced pressure (rotary evaporator) affording an oily residue.

Step 1B: Synthesis of methyl 4-(acetoxymethyl)-3-bromobenzoate

The residue from above was treated with glacial AcOH (30 mL) and KOAc (4.00 g, 40.76 mmol) and heated to 100° C. for 18 h. The reaction mixture was treated with crushed ice, CHCl$_3$ (150 mL) and neutralized with 10 N NaOH and NaHCO$_3$ saturated solution. The organic layer was separated and dried over MgSO$_4$, filtered and concentrated. The crude residue was purified on the ISCO 80 g column (eluted with 0-10% EtOAc in hexanes) affording the title compound as a white crystalline solid. MS (ESI, pos.ion) m/z: 313.1 (M+26).

Step 2: Synthesis of methyl 4-(acetoxymethyl)-3-(4,4,5,5-tetramethyl-1,3,2-dioxaborolan-2-yl)benzoate Methyl 4-(acetoxymethyl)-3-bromobenzoate (215 mg, 749 µmol), Pd(dppf)Cl$_2$ (55 mg, 75 mol), KOAc (169 mg, 1722 µmol), 4,4,5,5-tetramethyl-2-(4,4,5,5-tetramethyl-1,3,2-dioxaborolan-2-yl)-1,3,2-dioxaborolane (285 mg, 1123 µmol) and 1,4-dioxane (2.0 mL) were heated in a microwave at 130° C. for 23 min. The crude reaction mixture was filtered through a plug of celite washing with EtOAc. The residue was purified on the ISCO 40 g column (5-25% EtOAc in hexanes) affording the title compound as a white solid. MS (ESI, pos.ion) m/z: 357.1 (M+Na$^+$).

Step 3: Synthesis of 3-(1-(2,6-difluorophenyl)-7-methyl-6-oxo-6,7-dihydro-1H-pyrazolo[3,4-b]pyridin-5-yl)-4-(hydroxymethyl)benzoic acid Tetrakis(triphenylphosphine)palladium(0) (38 mg, 33 µmol), 5-bromo-1-(2,6-difluorophenyl)-7-methyl-1H-pyrazolo[3,4-b]pyridin-6(7H)-one (373 mg, 1096 µmol), methyl 4-(acetoxymethyl)-3-(4,4,5,5-tetramethyl-1,3,2-dioxaborolan-2-yl)benzoate (403 mg, 1206 µmol) were treated with 1,4-dioxane (5.4 mL) and 1 M aqueous Na$_2$CO$_3$ (2.74 mL, 2741 µmol) under argon and heated in a microwave at 130° C. for 30 min. The reaction mixture was treated with EtOAc (20 mL) and extracted with 1N NaOH (2×15 mL). The pH was adjusted to ca. pH 6 with 5N HCl and extracted with DCM (3×20 mL), dried over MgSO$_4$, filtered and concentrated affording the title compound (186 mg) as a yellow tar. The crude residue was used in the next step without further purification. MS (ESI, pos.ion) m/z: 412.1 (M+1).

Step 4: Synthesis of N-cyclopropyl-3-(1-(2,6-difluorophenyl)-7-methyl-6-oxo-6,7-dihydro-1H-pyrazolo[3,4-b]pyridin-5-yl)-4-(hydroxymethyl)benzamide 3-(1-(2,6-difluorophenyl)-7-methyl-6-oxo-6,7-dihydro-1H-pyrazolo[3,4-b]pyridin-5-yl)-4-(hydroxymethyl)benzoic acid (310 mg, 754 µmol) was treated with cyclopropanamine (0.21 mL, 3014 µmol) and HATU (430 mg, 1130 µmol) in THF (5.00 mL) under nitrogen and allowed to stir at RT. After 2 h the reaction was quenched by the addition of 1N NaOH (10 mL). The reaction mixture was extracted with EtOAc (2×25 mL), dried over MgSO$_4$, filtered and concentrated. The crude residue was purified on the ISCO 12 g column (70-100% EtOAc in hexanes) affording the title compound as an amorphous white solid. MS (ESI, pos.ion) m/z: 451.1 (M+1).

Example 33 (via Method G)

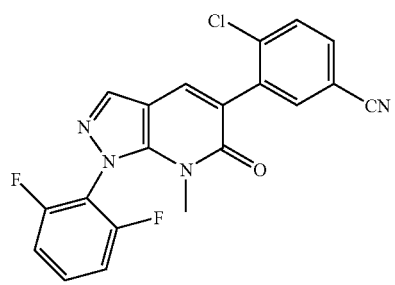

Synthesis of 4-chloro-3-(1-(2,6-difluorophenyl)-7-methyl-6-oxo-6,7-dihydro-1H-pyrazolo[3,4b]pyridin-5-yl)benzonitrile Step 1: Synthesis of 3-Bromo-4-chlorobenzenamine A mixture of 2-bromo-1-chloro-4-nitrobenzene (1.57 g, 6.6 mmol) and 10% palladium on charcoal (297 mg, 2.8 mmol) in EtOAc (50 mL) was stirred under an atmosphere of hydrogen (balloon) for 4 h. The reaction mixture was filtered through a pad of celite washing with EtOAc. The EtOAc was removed under reduced pressure affording the title compound as brown oil which solidified upon standing. It was used in the next step without further purification. MS (ESI, pos.ion) m/z: 206.0/208.0 (M+1).

Step 2A: Synthesis of tert-Butyl 3-bromo-4-chlorophenylcarbamate

Boc$_2$O (852 mg, 3.90 mmol) and 3-bromo-4-chlorobenzenamine (733 mg, 3.55 mmol) in THF (10 mL) were cooled in an ice bath and treated with NaH (102 mg, 4.26 mmol). It was stirred at 0° C. for 30 min then at RT for 2 h. The flask was fitted with a condenser and heated to 75° C. for 16 h. The solution was then cooled to RT, treated with brine (50 mL) and extracted with EtOAc (2×25 mL), dried over MgSO$_4$, filtered and concentrated. The crude residue was then purified on the ISCO 40 g column (0-25% EtOAc in hexanes) affording the title compound (813 mg) as a colorless crystalline solid. MS (ESI, pos.ion) m/z: 249.9/252.0 (M-t-Bu+1).

Step 2B: Synthesis of tert-Butyl-4-chloro-3-(4,4,5,5-tetramethyl-1,3,2-dioxaborolan-2-yl)phenylcarbamate A mixture of Pd(dppf)Cl$_2$ (126 mg, 0.17 mmol), KOAc (390 mg, 3.97 mmol), 4,4,5,5-tetramethyl-2-(4,4,5,5-tetramethyl-1,3,2-dioxaborolan-2-yl)-1,3,2-dioxaborolane (658 mg, 2.59 mmol) and tert-butyl 3-bromo-4-chlorophenylcarbamate (530 mg, 1.73 mmol) in 1,4-dioxane (5 mL) was heated in a microwave at 130° C. for 25 min. The crude reaction mixture was filtered through a pad of celite, and rinsed with EtOAc. The filtrate was concentrated and the crude residue was purified on the ISCO 40 g column (0-30% EtOAc in hexanes) to afford the title compound as a light yellow oil that crystallized upon standing. MS (ESI, pos.ion) m/z: 376.1 (M+Na$^+$).

Step 3: Synthesis of tert-Butyl 4-chloro-3-(1-(2,6-difluorophenyl)-7-methyl-6-oxo-6,7-dihydro-1H-pyrazolo[3,4-b]pyridin-5-yl)phenylcarbamate A mixture of tetrakis(triphenylphosphine)palladium(0) (42 mg, 0.037 mmol), 5-bromo-1-(2,6-difluorophenyl)-7-methyl-1H-pyrazolo[3,4-b]pyridin-6(7,H)-one (415 mg, 1.22 mmol) and tert-butyl 4-chloro-3-(4,4,5,5-tetramethyl-1,3,2-dioxaborolan-2-yl)phenylcarbamate (475 mg, 1.3 mmol) in 1,4-dioxane (5 mL) and 1M aqueous solution of Na$_2$CO$_3$ (2.44 mL, 2.44 mmol) was heated in a microwave at 130° C. for 35 min. The reaction mixture was treated with brine (20 mL) and extracted with EtOAc (2×25 mL). The organic extracts were dried over MgSO$_4$, filtered and concentrated. The crude residue was used in the subsequent step without further purification. MS (ESI, pos.ion) m/z: 487.1 (M+1).

Step 4A: Synthesis of 5-(5-Amino-2-chlorophenyl)-1-(2,6-difluorophenyl)-7-methyl-1H-pyrazolo[3,4-b]pyridin-6(7H)-one The crude residue from above in DCM (15 mL) at RT was treated with TFA (0.5 mL). The reaction mixture was stirred at RT for 1 h then 45° C. in an oil bath for 2 h. The volatiles were removed under reduced pressure. The remaining brown residue was dissolved in DCM, and neutralized with a saturated solution of NaHCO$_3$. The DCM solution was dried over MgSO$_4$, filtered and concentrated. The crude residue was purified on the ISCO 40 g column (30-90% EtOAc in hexanes) affording the title compound as an off-white amorphous solid. MS (ESI, pos.ion) m/z: 387.0 (M+1).

Step 4B: Synthesis of 5-(2-Chloro-5-iodophenyl)-1-(2,6-difluorophenyl)-7-methyl-1H-pyrazolo[3,4-b]pyridin-6(7H)-one At RT, a mixture of 5-(5-amino-2-chlorophenyl)-1-(2,6-difluorophenyl)-7-methyl-1H-pyrazolo[3,4-b]pyridin-6(7H)-one (230 mg, 0.59 mmol), iodine (151 mg, 0.59 mmol), copper(I) iodide (34 mg, 0.18 mmol) and cesium iodide (154 mg, 0.59 mmol) in DME (4.40 mL) was treated with isoamyl nitrite (0.48 mL, 3.57 mmol) drop wise over 3 min. The reaction mixture was stirred for 4 h, and filtered through a pad of celite washing with EtOAc (100 mL). The organic layer was washed sequentially with ~2% NH$_4$OH (20 mL), a solution of sodium thiosulfate (20 mL) and brine (20 mL), dried over MgSO$_4$, filtered and concentrated. The crude residue was purified on the ISCO 12 g column (10-60% EtOAc in hexanes) affording the title compound as a white crystalline solid. MS (ESI, pos.ion) m/z: 497.9 (M+1).

Step 5: Synthesis of 4-chloro-3-(1-(2,6-difluorophenyl)-7-methyl-6-oxo-6,7-dihydro-1H-pyrazolo[3,4-b]pyridin-5-yl)benzonitrile A mixture of 5-(2-chloro-5-iodophenyl)-1-(2,6-difluorophenyl)-7-methyl-1H-pyrazolo[3,4-b]pyridin-6(7H)-one (60 mg, 0.12 mmol) and copper(I) cyanide (54 mg, 0.6 mmol) in DMF (1.5 mL) were heated in a microwave at 140° C. for 1 h. LC-MS indicates ~60% conversion to the desired product. Additional copper(I) cyanide (100 mg) was added and the reaction mixture was heated for another 1 h in the microwave at 140° C. The reaction mixture was diluted in DCM (20 mL), washed with brine (2×15 mL), dried over MgSO$_4$, filtered and concentrated. The crude residue was purified on the ISCO 12 g column (15-50% EtOAc in hexanes) affording the title compound as a white amorphous solid. MS (ESI, pos.ion) m/z: 397.0 (M+1).

Example 34 (via Method H)

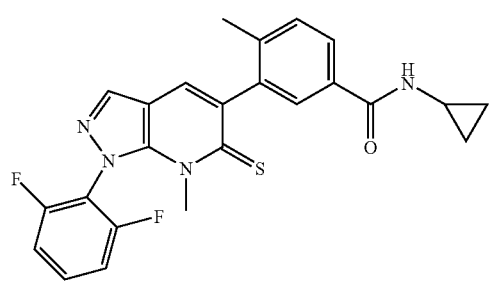

Synthesis of N-cyclopropyl-3-(1-(2,6-difluorophenyl)-7-methyl-6-thioxo-6,7-dihydro-1H-pyrazolo[3,4-b]pyridin-5-yl-4-methylbenzamide Step 1: Synthesis of 5-Bromo-1-(2,6-difluorophenyl)-7-methyl-1H-pyrazolo[3,4-b]pyridine-6(7H)-thione A mixture of Lawesson's reagent (297 mg, 0.73 mmol) and 5-bromo-1-(2,6-difluorophenyl)-7-methyl-1H-pyrazolo[3,4-b]pyridin-6(7H)-one (125 mg, 0.68 mmol) in toluene (8 mL) was heated to 125° C. for 15 h. The solvent was removed under reduced pressure (rotary evaporator) and the crude residue was purified on the ISCO 40 g column (5-40% EtOAc in hexanes) affording the title compound (101.6 mg) as a bright yellow crystalline solid. MS (ESI, pos.ion) m/z: 355.9/357.9 (M+1).

Step 2: N-Cyclopropyl-3-(1-(2,6-difluorophenyl)-7-methyl-6-thioxo-6,7-dihydro-1H-pyrazolo[3,4-b]pyridin-5-yl)-4-methylbenzamide The title compound was prepared by a method similar to that described in Example 1, step 5 (Method A), starting from the 1-cyclopropyl-3-(4-methyl-3-(4,4,5,5-tetramethyl-1,3,2-dioxaborolan-2-yl)phenyl)urea and 5-bromo-1-(2,6-difluorophenyl)-7-methyl-1H-pyrazolo[3,4-b]pyridine-6(7H)-thione. MS (ESI, pos.ion) m/z: 451.1 (M+1).

Example 35 (via Method I)

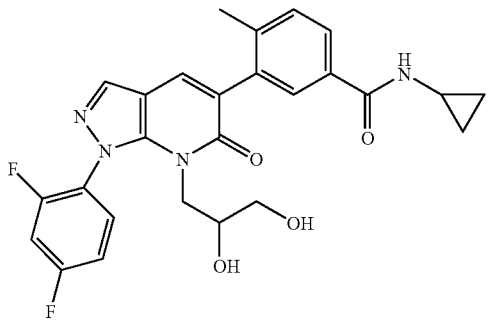

Synthesis of N-cyclopropyl-3-(1-(2,4-difluorophenyl)-7-(2,3-dihydroxypropyl)-6-oxo-6,7-dihydro-1H-pyrazolo[3,4b]pyridin-5-yl)-4-methylbenzamide Step 1: Synthesis of 7-Allyl-5-bromo-1-(2,4-difluorophenyl)-1H-pyrazolo[3,4-b]pyridin-6(7H)-one A solution of 5-bromo-1-(2,4-difluorophenyl)-1H-pyrazolo[3,4-b]pyridin-6(7H)-one (1.05 g, 3.22 mmol) in DME (10 mL) and DMF (0.9 mL) at 0° C. was treated with NaH (116 mg, 4.8 mmol). After stirring for 20 min at RT, lithium bromide (1.67 g, 19.32 m mol) was added and the reaction mixture was allowed to stir for 1 h at RT before addition of 3-bromoprop-1-ene (0.28 ml, 3.22 mmol). The mixture was allowed to stir at 40° C. for 18 h. The mixture was quenched with brine and extracted with 2×30 mL EtOAc. The combined EtOAc layers were washed with brine, dried and concentrated. Purification on the ISCO (40 g column, 10-80% EtOAc in Hexanes) afforded 7-allyl-5-bromo-1-(2,4-difluorophenyl)-1H-pyrazolo[3,4-b]pyridin-6(7H)-one as a tan amorphous solid. MS (ESI, pos.ion) m/z: 365.9/367.9 (M+1).

Step 2: Synthesis of 5-Bromo-1-(2,4-difluorophenyl)-7-(2,3-dihydroxypropyl)-1H-pyrazolo[3,4-b]pyridin-6(7H)-one A solution of 7-allyl-5-bromo-1-(2,4-difluorophenyl)-1H-pyrazolo[3,4-b]pyridin-6(7H)-one (265 mg, 0.724 mmol) in tert-BuOH (5 mL) and water (5 mL) at RT was treated with 4-methylmorpholine N-oxide (127 mg, 1.09 mmol) and potassium osmate dihydrate (10 mg, 0.027 mmol). The resulting mixture was allowed to stir for 16 h at RT, then diluted with an aqueous solution of sodium sulfite (10 mL) and extracted with EtOAc (3×25 mL). The organic extracts were dried over MgSO$_4$, filtered and concentrated. The crude residue was purified on the ISCO 12 g column (0-5% MeOH:DCM) affording the title compound as a white amorphous solid. MS (ESI, pos.ion) m/z: 399.0/401.0 (M+1).

Step 3: Synthesis of N-cyclopropyl-3-(1-(2,4-difluorophenyl)-7-(2,3-dihydroxypropyl)-6-oxo-6,7-dihydro-1H-pyrazolo[3,4-b]pyridin-5-yl)-4-methylbenzamide The title compound was prepared by a method similar to that described in Example 1, step 5 (Method A), starting from the 1-cyclopropyl-3-(4-methyl-3-(4,4,5,5-tetramethyl-1,3,2-dioxaborolan-2-yl)phenyl)urea and 5-bromo-1-(2,4-difluorophenyl)-7-(2,3-dihydroxypropyl)-1H-pyrazolo[3,4-b]pyridin-6(7H)-one. MS (ESI, pos.ion) m/z: 495.1 (M+1).

Example 36

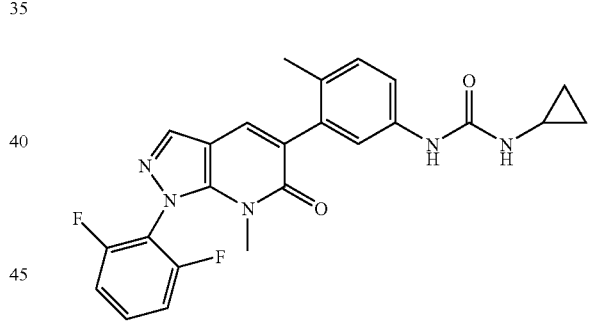

Synthesis of 1-Cyclopropyl-3-(3-(1-(2,6-difluorophenyl)-7-methyl-6-oxo-6,7-dihydro-1H-pyrazolo[3,4-b]pyridin-5-yl)-4-methylphenyl)urea Step 1: Synthesis of 1-cyclopropyl-3-(4-methyl-3-(4,4,5,5-tetramethyl-1,3,2-dioxaborolan-2-yl)phenyl)urea A mixture of CDI (254 mg, 1.57 mmol) and 4-methyl-3-(4,4,5,5-tetramethyl-1,3,2-dioxaborolan-2-yl)benzenamine (332 mg, 1.42 mmol) under nitrogen was treated with THF (10 mL) and heated to 50° C. for 45 min. The solution was then cooled to RT and treated with cyclopropylamine (113 μl, 1.64 mmol) and again heated to 40° C. for 11 h. The volatiles were then removed in vacuo (rotary evaporator) and the crude solid was purified on the ISCO 40 g column (15-70% EtOAc in hexanes) affording the title compound as a white amorphous solid. MS (ESI, pos.ion) m/z: 317.2 (M+1).

Step 2: Synthesis of 1-cyclopropyl-3-(3-(1-(2,6-difluorophenyl)-7-methyl-6-oxo-6,7-dihydro-1H-pyrazolo[3,4-b]pyridin-5-yl)-4-methylphenyl)urea The title compound was prepared by a method similar to that described in Example 1, step 5 (Method A), starting from the 1-cyclopropyl-3-(4-methyl-3-(4,4,5,5-tetramethyl-1,3,2-dioxaborolan-2-yl)phenyl)urea and 5-bromo-1-(2,6-difluorophenyl)-7-methyl-1H-pyrazolo[3,4-b]pyridin-6(7H)-one. MS (ESI, pos.ion) m/z: 317.2 (M+1).

The following Examples in Table 2 will further assist in understanding and appreciating the invention. The compounds of examples 37-53 were made in accordance with exemplary methods A, B and D-I, which correspond to Examples 1-4 and 32-35 above, respectively, and named according to the ACD naming convention, as associated with ISIS software. The mass spectral data is recorded M+H+, which is the positive ion as measured by an electrospray ionization method. The biological assay data is provided for those exemplary compounds in Table 2 which were tested in, and data calculated from, the human whole blood and p38α cellular assays. Not every compound example was run in these assays at the time of filing of this application, and accordingly no data is provided in the Table.

TABLE 2

| Ex. No. | Name | MS (M + H+) | Method | WB TNF/IL8 IC50 (nM) | p38a IC50 (nM) |
|---|---|---|---|---|---|
| 37 | 5-(5-amino-2-methylphenyl)-1-(2,4-difluorophenyl)-7-methyl-1,7-dihydro-6H-pyrazolo[3,4-b]pyridin-6-one | 367 | G | 326 | |
| 38 | 3-(1-(2,6-difluorophenyl)-7-methyl-6-oxo-6,7-dihydro-1H-pyrazolo[3,4-b]pyridin-5-yl)-4-methylbenzoic acid | 396.1 | B | 2500 | 704 |
| 39 | 5-(5-amino-2-methylphenyl)-1-(2,6-difluorophenyl)-7-methyl-1,7-dihydro-6H-pyrazolo[3,4-b]pyridin-6-one | 367 | G | 60 | |
| 40 | 1-(2,6-difluorophenyl)-5-(5-iodo-2-methylphenyl)-7-methyl-1,7-dihydro-6H-pyrazolo[3,4-b]pyridin-6-one | 478 | G | 2500 | |
| 41 | 3-(1-(2,4-difluorophenyl)-7-methyl-6-oxo-6,7-dihydro-1H-pyrazolo[3,4-b]pyridin-5-yl)-4-methylbenzoic acid | 396 | B | 2500 | 1000 |
| 42 | 4-chloro-3-(1-(2,6-difluorophenyl)-7-methyl-6-oxo-6,7-dihydro-1H-pyrazolo[3,4-b]pyridin-5-yl)benzoic acid | 416.0 | B | 2500 | |
| 43 | 1-(2,4-difluorophenyl)-5-(5-iodo-2-methylphenyl)-7-methyl-1,7-dihydro-6H-pyrazolo[3,4-b]pyridin-6-one | 478 | G | 2500 | |
| 44 | 3-(1-(2,6-difluorophenyl)-7-methyl-6-oxo-6,7-dihydro-1H-pyrazolo[3,4-b]pyridin-5-yl)-4-methylbenzamide | 395 | B | 5.4 | 3.4 |
| 45 | 3-(1-(2,6-difluorophenyl)-7-methyl-6-oxo-6,7-dihydro-1H-pyrazolo[3,4-b]pyridin-5-yl)-4-methyl-N-(2-(methyloxy)-5-(trifluoromethyl)phenyl)benzamide | 569.1 | D | 2500 | 7.8 |
| 32 | N-cyclopropyl-3-(1-(2,6-difluorophenyl)-7-methyl-6-oxo-6,7-dihydro-1H-pyrazolo[3,4-b]pyridin-5-yl)-4-(hydroxymethyl)benzamide | 451.1 | F | 16 | 21 |
| 46 | N-cyclopropyl-3-(1-(2,4-difluorophenyl)-7-ethyl-6-oxo-6,7-dihydro-1H-pyrazolo[3,4-b]pyridin-5-yl)-4-methylbenzamide | 449.1 | B | 2.5 | 4.9 |
| 33 | 3-(1-(2,6-difluorophenyl)-7-methyl-6-oxo-6,7-dihydro-1H-pyrazolo[3,4-b]pyridin-5-yl)-4-methylbenzonitrile | 377.1 | G | 2500 | |
| 34 | N-cyclopropyl-3-(1-(2,6-difluorophenyl)-7-methyl-6-thioxo-6,7-dihydro-1H-pyrazolo[3,4-b]pyridin-5-yl)-4-methylbenzamide | 451.1 | H | 4.4 | 2.6 |
| 47 | N-cyclopropyl-3-(1-(cyclopropylsulfonyl)-7-methyl-6-oxo-6,7-dihydro-1H-pyrazolo[3,4-b]pyridin-5-yl)-4-methylbenzamide | 427.1 | E | 662 | |
| 48 | 5-(5-amino-2-chlorophenyl)-1-(2,6-difluorophenyl)-7-methyl-1,7-dihydro-6H-pyrazolo[3,4-b]pyridin-6-one | 387 | G | 327 | |
| 49 | 5-(2-chloro-5-iodophenyl)-1-(2,6-difluorophenyl)-7-methyl-1,7-dihydro-6H-pyrazolo[3,4-b]pyridin-6-one | 497.9 | G | | |
| 50 | 4-chloro-3-(1-(2,6-difluorophenyl)-7-methyl-6-oxo-6,7-dihydro-1H-pyrazolo[3,4-b]pyridin-5-yl)benzonitrile | 397 | G | 2500 | |
| 51 | N-cyclopropyl-3-(1-(2,4-difluorophenyl)-7-methyl-6-thioxo-6,7-dihydro-1H-pyrazolo[3,4-b]pyridin-5-yl)-4-methylbenzenecarbothioamide | 581.3 | H | 225 | |

TABLE 2-continued

| Ex. No. | Name | MS (M + H+) | Method | WB TNF/IL8 IC50 (nM) | p38a IC50 (nM) |
|---|---|---|---|---|---|
| 35 | N-cyclopropyl-3-(1-(2,4-difluorophenyl)-7-(2,3-dihydroxypropyl)-6-oxo-6,7-dihydro-1H-pyrazolo[3,4-b]pyridin-5-yl)-4-methylbenzamide | 495.1 | I | 22 | 34 |
| 52 | N-cyclopropyl-3-(1-(4-fluorophenyl)-7-methyl-6-oxo-6,7-dihydro-1H-pyrazolo[3,4-b]pyridin-5-yl)-4-methylbenzamide | 417.1 | B | 7.2 | 6.1 |
| 53 | 4-chloro-N-cyclopropyl-3-(1-(4-fluorophenyl)-7-methyl-6-oxo-6,7-dihydro-1H-pyrazolo[3,4-b]pyridin-5-yl)benzamide | 437.1 | B | 27 | 6 |
| 36 | 1-cyclopropyl-3-(3-(1-(2,6-difluorophenyl)-7-methyl-6-oxo-6,7-dihydro-1H-pyrazolo[3,4-b]pyridin-5-yl)-4-methylphenyl)urea | 450.1 | A | 261 | |

The following compounds in Table 3 are additional representative examples of Formula I as provided by the present invention.

TABLE 3

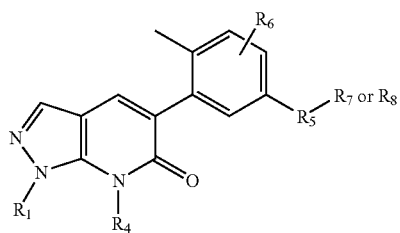

| Ex. No. | R$^1$ | R$^4$ | R$^6$ | R$^5$ | R$^7$ or R$^8$ |
|---|---|---|---|---|---|
| 54 | 3,5-difluoro-Ph | —CH$_2$CH$_3$— | H | —C(O)NH— | oxazolyl |
| 55 | morpholine | —CH$_3$— | H | —C(O)NH— | methyl or cyclopropyl |
| 56 | piperazine | —CH$_2$CH$_3$— | H | —C(O)NH— | methyl or cyclopropyl |
| 57 | piperidine | —CH$_3$— | H | —C(O)NH— | methyl or cyclopropyl |
| 58 | phenyl | —CH$_3$— | F | —C(O)NH— | methyl or cyclopropyl |
| 59 | m-CH$_3$-phenyl- | —CH$_2$CH$_3$— | Cl | —C(O)NH— | methyl or cyclopropyl |
| 60 | m-Cl-phenyl- | —CH$_2$CH$_3$— | OCH$_3$ | —C(O)NH— | methyl or cyclopropyl |
| 61 | 3,5-difluoro-Ph | —CH$_2$CH$_3$— | H | —C(O)NH— | isoxazolyl |
| 62 | morpholine | —CH$_3$— | H | —C(O)NH— | pyrazolyl |
| 63 | piperazine | —CH$_2$CH$_3$— | H | —C(O)NH— | imidazolyl |
| 64 | piperidine | —CH$_3$— | H | —C(O)NH— | triazolyl |
| 65 | phenyl | —CH$_3$— | F | —C(O)NH— | tetrazolyl |
| 66 | m-CH$_3$-phenyl- | —CH$_2$CH$_3$— | Cl | —C(O)NH— | thioazolyl |
| 67 | 2-cl-phenyl | —CH$_2$CH$_3$— | OCH$_3$ | —C(O)NH— | isothiazolyl |
| 68 | 2-CH$_3$-phenyl | —CH$_2$CH$_3$— | H | —NHC(O)— | phenyl |
| 69 | 4-CH$_3$-phenyl | —CH$_3$— | H | —NHC(O)— | cyclopropyl |
| 70 | 4-cl-phenyl | —CH$_2$CH$_3$— | di-F | —NHC(O)— | ethyl |
| 71 | 3-cl-phenyl | —CH$_3$— | di-Cl | —NHC(O)— | propyl |
| 72 | 3-CH$_3$-phenyl | —CH$_3$— | OCH$_3$ | —NHC(O)— | butyl |
| 73 | 2-thiophene | —CH$_2$CH$_3$— | CF$_3$ | —NHC(O)— | isopropyl |
| 74 | 3-thiophene | —CH$_3$— | OCF$_3$ | —NHC(O)— | isobutyl |
| 75 | 2-pyridine | —CH$_2$CH$_3$— | OH | —NHC(O)— | cyclopentyl |
| 76 | 1-morpholinyl | —(CH$_2$)$_2$CH$_3$— | F | —C(O)NH— | ethyl |
| 77 | 1-piperazinyl | —CH$_3$— | Cl | —C(O)NH— | ethyl |
| 78 | 1-piperidinyl | —CH$_2$CH$_3$— | OCH$_3$ | —C(O)NH— | ethyl |
| 79 | 3,5-difluoro-Ph | —CH$_3$— | F | —C(O)NH— | ethyl |
| 80 | 3-cl-phenyl | —CH$_2$CH$_3$— | Cl | —C(O)NH— | ethyl |
| 81 | 3-CH$_3$-phenyl | —CH$_3$— | OCH$_3$ | —C(O)NH— | ethyl |
| 82 | 2-thiophene | —CH$_2$CH$_3$— | H | —C(O)NH— | ethyl |
| 83 | phenyl | —NH— | —NHCH$_3$ | —NH— | isoxazolyl |
| 84 | 3-amido-1-pyrrolidinyl | —CH$_3$— | H | —NH— | pyrazolyl |
| 85 | 3-amido-1-piperidinyl | —CH$_2$CH$_3$— | H | —NH— | imidazolyl |
| 86 | 4-amido-1-piperidinyl | —CH$_3$— | F | —NH— | triazolyl |
| 87 | 4N-CH$_3$-1-piperizinyl | —CH$_2$CH$_3$— | Cl | —C(O)— | tetrazolyl |
| 88 | 2-cl-phenyl | —(CH$_2$)$_2$CH$_3$— | OCH$_3$ | —C(O)— | thioazolyl |

TABLE 3-continued

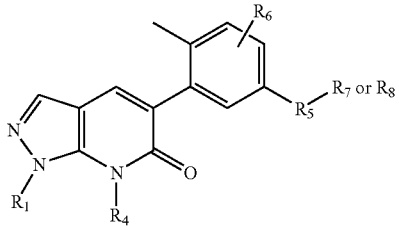

| Ex. No. | R$^1$ | R$^4$ | R$^6$ | R$^5$ | R$^7$ or R$^8$ |
|---|---|---|---|---|---|
| 89 | 2-CH$_3$-phenyl | —CH$_3$— | F | —C(O)— | isothiazolyl |
| 90 | 4-CH$_3$-phenyl | —CH$_2$CH$_3$— | Cl | —C(O)— | phenyl |
| 91 | 4-cl-phenyl | —CH$_2$CH$_3$— | OCH$_3$ | —C(O)NH— | cyclopropyl |
| 92 | 3-cl-phenyl | —CH$_3$— | F | —C(O)NH— | ethyl |
| 93 | 3-CH$_3$-phenyl | —CH$_3$— | —NHCH$_3$ | —C(O)NH— | propyl |
| 94 | 2-thiophene | —CH$_2$CH$_3$— | H | —C(O)NH— | ethyl |
| 95 | 3-thiophene | —(CH$_2$)$_2$CH$_3$— | H | —C(O)NH— | ethyl |
| 96 | 2-pyridine | —CH$_3$— | F | —C(O)NH— | ethyl |
| 97 | 1-morpholinyl | —CH$_2$CH$_3$— | Cl | —C(O)NH— | cyclopropyl |
| 98 | 1-piperazinyl | —CH$_2$CH$_3$— | CN | —NHC(O)— | propyl |
| 99 | 1-piperidinyl | —CH$_3$— | CF$_3$ | —NHC(O)— | cyclopropyl |
| 100 | cyclohexyl-N— | —CH$_3$— | OH | —NHC(O)— | cyclopropyl |
| 101 | morpholine-(CH$_2$)$_2$—N— | —CH$_2$CH$_3$— | NHCH$_3$ | —NHC(O)— | propyl |
| 102 | (CH$_3$)$_2$N—(CH$_2$)$_2$— | —(CH$_2$)$_2$CH$_3$— | H | —NHC(O)— | propyl |
| 103 | (C$_2$H$_5$)$_2$N—(CH$_2$)$_2$— | —CH$_3$— | acetyl | —NHC(O)— | cyclopropyl |
| 104 | 3-OH-1-pyrrolidinyl | —CH$_2$CH$_3$— | H | —NHC(O)— | propyl |
| 105 | —CH$_2$CH$_3$— | —CH$_2$CH$_3$— | H | —NHC(O)— | propyl |
| 106 | —(CH$_2$)$_2$CH$_3$— | —CH$_2$CH$_3$— | acetyl | —C(O)NH— | isoxazolyl |
| 107 | —CH$_3$— | —(CH$_2$)$_2$CH$_3$— | H | —C(O)NH— | pyrazolyl |
| 108 | 4N-CH$_3$-1-piperizinyl | —CH$_3$— | H | —C(O)NH— | imidazolyl |
| 109 | 2-cl-phenyl | —CH$_2$CH$_3$— | H | —C(O)NH— | triazolyl |
| 110 | 2-CH$_3$-phenyl | —CH$_2$CH$_3$— | H | —C(O)NH— | tetrazolyl |
| 111 | 4-CH$_3$-phenyl | —CH$_3$— | CN | —C(O)NH— | thioazolyl |
| 112 | 4-cl-phenyl | —CH$_3$— | H | —S(O)$_2$NH— | isothiazolyl |
| 113 | 3-cl-phenyl | —CH$_2$CH$_3$— | H | —NH— | phenyl |
| 114 | 3-CH$_3$-phenyl | —(CH$_2$)$_2$CH$_3$— | H | —NH— | cyclopropyl |
| 115 | 2-thiophene | —CH$_3$— | H | —NH— | ethyl |
| 116 | 3-thiophene | —CH$_2$CH$_3$— | H | —NH— | propyl |
| 117 | 2-pyridine | —CH$_2$CH$_3$— | H | —C(O)— | isoxazolyl |
| 118 | 4-F-phenyl | —CH$_3$— | CH$_3$ | —C(O)— | pyrazolyl |

The following compounds in Table 4 are additional representative examples of Formula II as provided by the present invention.

TABLE 4

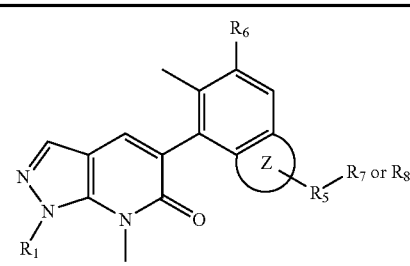

| Ex. No. | R$^1$ | Z | R$^6$ | R$^5$ | R$^7$ or R$^8$ |
|---|---|---|---|---|---|
| 119 | 3-thiophene | isoxazolyl | H | —C(O)NH— | Methyl or cyclopropyl |
| 120 | 2-pyridine | pyrazolyl | F | —C(O)NH— | Methyl or cyclopropyl |
| 121 | 1-morpholinyl | imidazolyl | Cl | —C(O)NH— | Methyl or cyclopropyl |
| 122 | 1-piperizinyl | triazolyl | Br | —NHC(O)— | Methyl or cyclopropyl |
| 123 | 1-piperidinyl | tetrazolyl | OH | —NHC(O)— | Methyl or cyclopropyl |
| 124 | cyclohexyl-N- | thioazolyl | CN | —NHC(O)— | Methyl or cyclopropyl |
| 125 | morpholine-(CH$_2$)$_2$—N— | isothiazolyl | H | —NHC(O)— | Methyl or cyclopropyl |

TABLE 4-continued

| Ex. No. | R¹ | Z | R⁶ | R⁵ | R⁷ or R⁸ |
|---|---|---|---|---|---|
| 126 | (CH₃)₂N—(CH₂)₂— | oxazolyl | H | —NHC(O)— | Methyl or cyclopropyl |
| 127 | (C₂H₅)₂N—(CH₂)₂— | pyrrole | H | —NHC(O)— | Methyl or cyclopropyl |
| 128 | 3-OH-1-pyrrolidinyl | pyridyl | H | —NHC(O)— | Methyl or cyclopropyl |
| 129 | —CH₂CH₃— | pyrimidyl | H | —NHC(O)— | Methyl or cyclopropyl |
| 130 | —(CH₂)₂CH₃— | pyridinonyl | H | —C(O)NH— | Methyl or cyclopropyl |
| 131 | —CH₃— | oxazolyl | H | —C(O)NH— | Methyl or cyclopropyl |
| 132 | 4N-CH₃-1-piperizinyl | isoxazolyl | H | —C(O)NH— | Methyl or cyclopropyl |
| 133 | 2-cl-phenyl | 2-thiophene | H | —C(O)NH— | Methyl or cyclopropyl |
| 134 | 2-CH₃-phenyl | 3-thiophene | H | —C(O)NH— | Methyl or cyclopropyl |
| 135 | 4-CH₃-phenyl | 2-pyridine | H | —C(O)NH— | Methyl or cyclopropyl |
| 136 | 4-cl-phenyl | 3-pyridine | H | —S(O)₂NH— | Methyl or cyclopropyl |
| 137 | 3-cl-phenyl | pyrazolyl | H | —NH— | Methyl or cyclopropyl |
| 138 | 3-CH₃-phenyl | imidazolyl | H | —NH— | Methyl or cyclopropyl |
| 139 | 2-thiophene | triazolyl | H | —NH— | Methyl or cyclopropyl |
| 140 | 3-thiophene | tetrazolyl | H | —NH— | ethyl |
| 141 | 2-pyridine | thioazolyl | H | —C(O)— | ethyl |
| 142 | 4-F-phenyl | isothiazolyl | H | —C(O)— | ethyl |
| 143 | 3-thiophene | oxazolyl | H | —C(O)— | ethyl |
| 144 | morpholine-(CH₂)₂— | isoxazolyl | H | —NH— | ethyl |
| 145 | (CH₃)₂N—(CH₂)₂— | pyrazolyl | H | —NH— | ethyl |
| 146 | (C₂H₅)₂N—(CH₂)₂— | imidazolyl | H | —NH— | cyclopropyl |
| 147 | 3-OH-1-pyrrolidinyl | triazolyl | H | —NH— | propyl |
| 148 | 3-amido-1-pyrrolidinyl | tetrazolyl | H | —NH— | cyclopropyl |
| 149 | 3-amido-1-piperidinyl | thioazolyl | H | —NH— | cyclopropyl |
| 150 | 4-amido-1-piperidinyl | isothiazolyl | H | —NH— | propyl |
| 151 | 4N-CH₃-1-piperizinyl | oxazolyl | H | —NH— | propyl |
| 152 | 2-cl-phenyl | pyrrole | H | —NH— | cyclopropyl |
| 153 | 2-CH₃-phenyl | pyridyl | H | —NH— | propyl |
| 154 | 4-CH₃-phenyl | pyrimidyl | H | —NH— | propyl |
| 155 | 4-cl-phenyl | pyridinonyl | H | —NH— | isoxazolyl |
| 156 | 3-cl-phenyl | oxazolyl | H | —NH— | pyrazolyl |
| 157 | 3-CH₃-phenyl | isoxazolyl | H | —NH— | imidazolyl |
| 158 | 2-thiophene | 2-thiophene | H | —NH— | triazolyl |
| 159 | 3-thiophene | 3-thiophene | H | —NH— | tetrazolyl |
| 160 | 2-pyridine | 2-pyridine | H | —NH— | thioazolyl |
| 161 | 1-morpholinyl | 3-pyridine | H | —NH— | isothiazolyl |
| 162 | 1-piperazinyl | pyrazolyl | H | —NH— | phenyl |
| 163 | 1-piperidinyl | imidazolyl | H | —NH— | cyclopropyl |
| 164 | cyclohexyl- | triazolyl | H | —NH— | ethyl |
| 165 | morpholine-(CH₂)₂— | tetrazolyl | H | —NH— | propyl |
| 166 | (CH₃)₂N—(CH₂)₂— | thioazolyl | H | —C(O)NH— | isoxazolyl |
| 167 | (C₂H₅)₂N—(CH₂)₂— | isothiazolyl | H | —C(O)NH— | pyrazolyl |
| 168 | 3-OH-1-pyrrolidinyl | oxazolyl | H | —C(O)NH— | ethyl |
| 169 | 3-amido-1-pyrrolidinyl | isoxazolyl | H | —C(O)NH— | ethyl |
| 170 | 3-amido-1-piperidinyl | pyrazolyl | H | —NH— | cyclopropyl |
| 171 | 4-amido-1-piperidinyl | imidazolyl | H | —NH— | propyl |
| 172 | 4N-CH₃-1-piperizinyl | isoxazolyl | H | —NH— | propyl |
| 173 | 2-cl-phenyl | pyrazolyl | H | —NH— | propyl |
| 174 | 2-CH₃-phenyl | imidazolyl | H | —NH— | isopropyl |
| 175 | 4-CH₃-phenyl | triazolyl | H | —NH— | propyl |
| 176 | 4-cl-phenyl | tetrazolyl | H | —NH— | propyl |
| 177 | 3-cl-phenyl | thioazolyl | H | —NH— | isopropyl |
| 178 | 3-CH₃-phenyl | isothiazolyl | H | —NH— | propyl |
| 179 | 2-thiophene | oxazolyl | H | —NH— | isopropyl |
| 180 | 3-thiophene | pyrrole | H | —NH— | allyl |
| 181 | 2-pyridine | pyridyl | H | —NH— | propyl |
| 182 | 4-F-phenyl | pyrimidyl | CH₃ | —NH— | cyclopropyl |

While the examples and schemes described above provide processes for synthesizing compounds, and intermediates thereof, of Formulas I, I-B and I-C, it should be appreciated that other methods may be utilized to prepare such compounds. Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. Persons of ordinary skill in the art know, or can easily establish, which protecting groups are suitable with the reactions described herein.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, 4$^{th}$ edition, Volume 15/1, Georg Thieme Verlag, Stuttgart (1974), in H.-D. Jakubke and H, Jescheit, Aminosäuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., ethyl acetate; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, —CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise provided by this invention. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

In synthesizing a compound of formulas I, I-B and I-C according to a desired procedure, the steps may be performed in an order suitable to prepare the compound, including a procedure described herein or by an alternate order of steps described herein, and may be preceded, or followed, by additional protection/deprotection steps as necessary. The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

In one embodiment, the present invention provides a method of making a compound of Formula I, the method comprising the step of reacting a compound 7,

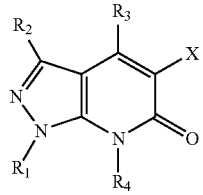

7 wherein $R^1$, $R^2$, $R^3$ and $R^4$ are as defined herein and X is a halogen, with a boronic acid having a general formula

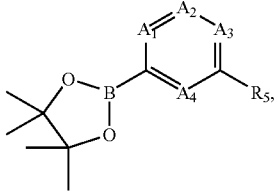

wherein $A^1$, $A^2$, $A^3$, $A^4$ and $R^5$ are as defined herein, to make a compound of Formula I.

In another embodiment, the present invention provides a method of making a compound of Formula I-B, the method comprising the step of reacting a compound 7-B,

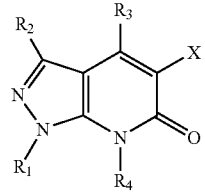

7-B wherein $R^1$, $R^2$, $R^3$ and $R^4$ are as defined herein and X is a halogen, with a boronic acid having a general formula

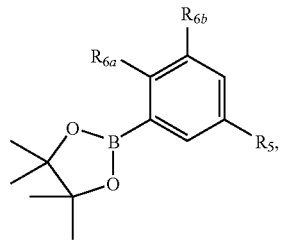

wherein $R^{6a}$, $R^{6b}$, and $R^5$ are as defined herein, to make a compound of Formula I-B.

In another embodiment, the present invention provides a method of making a compound of Formula I-C, the method comprising the step of reacting a compound 7-C,

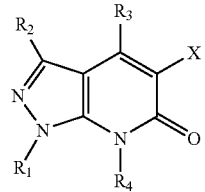

7-C wherein $R^1$, $R^2$, $R^3$ and $R^4$ are as defined herein and X is a halogen, with a boronic acid having a general formula

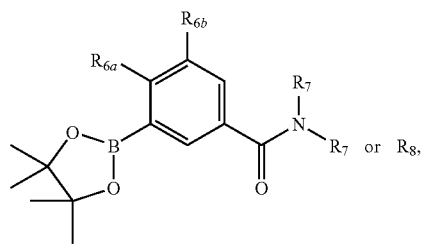

wherein $R^{6a}$, $R^{6b}$, $R^7$ and $R^8$ are as defined herein, to make a compound of Formula I-C.

Compounds of the present invention can possess, in general, one or more asymmetric carbon atoms and are thus capable of existing in the form of optical isomers including, without limitation, racemates and racemic mixtures, scalemic mixtures, single enantiomers, individual diastereomers and diastereomeric mixtures. All such isomeric forms of these compounds are expressly included in the present invention. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

BIOLOGICAL EVALUATION

The compounds of the invention may be modified by appending appropriate functionalities to enhance selective biological properties. Such modifications are known in the art and include those which increase biological penetration into a given biological compartment (e.g., blood, lymphatic system, central nervous system), increase oral bioavailability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I, I-B and I-C) vary with structural change, in general, activity possessed by compounds of Formulas I and II may be demonstrated both in vitro as well as in vivo. Particularly, the pharmacological properties of the compounds of this invention may be confirmed by a number of pharmacological in vitro assays, as well as in-vivo animal models.

The following assays were used to characterize the ability of compounds of the invention to modulate the activity of human p38 enzyme, inhibit the production of TNF-α and interleukin cytokines, including IL-1, IL-1-β, IL-6 and IL-8 and/or evaluate efficacy of a compound in an in vivo animal model. Another assay, a cyclooxygenase enzyme (COX-1 and COX-2) inhibition activity in vitro assay, can be used to characterize the ability of compounds of the invention to inhibit COX-1 and/or COX-2.

Purified and Activated Recombinant Human p38α Assay

Kinase Reaction Buffer: Kinase reaction buffer for p38α HTRF assays consists of 50 mM Tris-pH 7.5, 5 mM $MgCl_2$, 0.1 mg/mL BSA, 100 µM $Na_3VO_4$ and 0.5 mM DTT.

HTRF Detection Buffer: HTRF detection buffer contains 100 mM HEPES-pH 7.5, 100 mM NaCl, 0.1% BSA, 0.05% Tween-20, and 10 mM EDTA.

Serial Dilution of Compounds: Compounds were dissolved in 100% DMSO and serially diluted (3 fold, 10 point) in a polypropylene 96-well microtiter plate (drug plate). The final starting concentration of compounds in the p38α enzymatic assays was 1 µM. Columns 6 and 12 (HI controls and LO controls respectively) in the drug plate were reserved as controls and contained only DMSO.

Kinase Reaction The p38α kinase reactions were carried out in a polypropylene 96-well black round bottom assay plate in total volume of 30 µL kinase reaction buffer. Appropriate concentration of purified and activated enzyme (recombinant human) was mixed with indicated concentration of ATP and 100 nM GST-ATF2-Avitag, in the presence or absence (HI control) of Compound. See table below for actual concentrations. In the absence of substrate, the background was measured as LO control. The reaction was allowed to incubate for 1 hour at RT.

Assay Reagent Concentrations: The final reagent concentrations were 1 nM p38α and 50 µM ATP. The Km for ATP of the enzyme was 103 µM, giving a ratio of ATP concentration to Km of 0.49.

HTRF Detection: The kinase reaction was terminated and phospho-ATF2 was revealed by addition of 30 µL of HTRF detection buffer supplemented with 0.1 nM Eu-anti-pTP and 4 nM SA-APC. After 60 minutes incubation at room temperature, the assay plate was read in a Discovery Plate Reader. The wells were excited with coherent 320 nm light and the ratio of delayed (50 ms post excitation) emissions at 620 nM (native europium fluorescence) and 665 nm (europium fluorescence transferred to allophycocyanin—an index of substrate phosphorylation) was determined (Park et al, 1999).

Data Analysis: The proportion of substrate phosphorylated in the kinase reaction in the presence of compound compared with that phosphorylated in the presence of DMSO vehicle alone (HI control) was calculated using the formula: % control (POC)=(compound−average LO)/(average HI−average LO)*100. Data (consisting of POC and inhibitor concentration in µM) was fitted to a 4-parameter equation $(y=A+((B-A)/(1+((x/C)^D)))$, where A is the minimum y (POC) value, B is the maximum y (POC), C is the x (compound concentration) at the point of inflection and D is the slope factor, using a Levenburg-Marquardt non-linear regression algorithm.

The inhibition constant (Ki) of the inhibitor was estimated from the $IC_{50}$ (compound concentration at the point of inflection C) using the Cheng-Prussof equation: $Ki=IC_{50}/(1+S/Km)$, where S is the ATP substrate concentration, and Km is the Michaelis constant for ATP as determined experimentally. All results were expressed as the mean±the standard error of the mean. Data acquisition and non-linear regression algorithms were performed using Activity Base v5.2 and XL-fit software v4.1 respectively. All data was archived using Activity Base v5.2 software. Data for Exemplary compounds in the human p38-alpha enzyme assay is provided in Tables 1 and 2.

Examples 1-3, 6-15, 18-28, 31-32, 34-35, 37, 44-46 and 51-53 exhibited $IC_{50}$ values of less than or equal to 100 nM.

Lipopolysaccharide-Activated PBMC Cytokine Production Assay

Isolation of PBMC

Test compounds were evaluated in vitro for the ability to inhibit the production of IL-1β, IL-6, and TNF-α by PBMC activated with bacterial lipopolysaccharide (LPS). Fresh leukocytes were obtained from a local blood bank, and peripheral blood mononuclear cells (PBMCs) were isolated by density gradient centrifugation on Ficol-Paque Plus (Pharmacia).

Preparation of Test Compound Stock Solutions

All reagents were prepared in RPMI 1640+10% v/v human AB serum+1×Pens/Strep/Glu (assay medium). Test compounds were dissolved in 100% DMSO and serially diluted in 96-well polypropylene round bottom micro titer plates (drug plate). Serial dilutions were then diluted 1:250 into assay medium to a 4× working concentration. Compound serial dilutions were half-log, 10 point titrations with a final starting concentration of 1 µM.

Treatment of Cells with Test Compounds and Activation with Lipopolysaccharide

LPS was prepared to a 4× concentration in assay medium. 100 µl of PBMC (1×10⁶ cells/ml) were plated in a 96-well polystyrene flat bottom micro titer tissue culture plate and incubated with 50 µl of 4× compound serial dilution for 1 hour at 37° C., 5% $CO_2$ in a tissue culture incubator. 50 µl 4×LPS or control was added and the plates were incubated at 37° C., 5% $CO_2$ in a tissue culture incubator for 18 hours. The final DMSO concentration was 0.1%. The total volume was 200 µL. The final LPS concentration was 100 ng/mL. After 18 hours culture supernatants were removed and IL-1β, IL-6, and TNF-α presence in the supernatants was quantified using MSD ECL based technology.

Cytokine Measurements 20 µL of culture supernatant were added to MSD plates, and incubated for one hour at room temperature. 20 µL of detection antibody diluted in antibody diluent (1 µg/mL), and 110 µL of 2× Read Buffer P was added, and incubated for one hour at RT. Electrochemiluminescence was measured using the SECTOR HTS Imager (MSD, Gaithersburg, Md.).

Data Analysis

Compound $IC_{50}$ values were calculated as follows: The proportion of cytokine production in the presence of compound compared to the cytokine production in the presence of the DMSO vehicle alone (Hi control) was calculated using the formula: Percent Control (POC)=(compound−average Lo)/(average Hi−average Lo)*100. To derive $IC_{50}$ values, POC was plotted against the Log of compound concentration (µM) and fitted to a 4-parameter equation (y=A+((B−A)/(1+((x/C)^D))), where A is the minimum y (POC) value, B is the maximum y (POC), C is the concentration of compound at the inflection point, and D is the slope factor, using a Levenburg-Marquardt non-linear regression algorithm. Data acquisition and non-linear regression were performed using Activity Base and XL-fit respectively. The compounds of Examples 2, 3, 7, 8, 12, 13, 20, 27, 31 and 44 exhibited activities in the whole blood PMBC assay with $IC_{50}$ values of equal to 125 nM or less.

Compounds of the invention can also be shown to inhibit LPS-induced release of IL-1β, IL-6 and/or IL-8 from PBMC by measuring concentrations of IL-1, IL-6 and/or IL-8 by methods well known to those skilled in the art. In a similar manner to the above described assay involving the LPS induced release of TNF-α from PBMC, compounds of this invention can also be shown to inhibit LPS induced release of IL-1β, IL-6 and/or IL-8 from PBMC by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Lipopolysaccharide-Activated THP1 Cell TNF Production Assay

THP1 cells were resuspended in fresh THP1 media (RPMI 1640, 10% heat-inactivated FBS, 1×PGS, 1×NEAA, plus 30 µM βME) at a concentration of 1.5×10⁶ cells per mL. One hundred microliters of cells per well were plated in a polystyrene 96-well tissue culture plate. 1.5 micrograms per mL of bacterial LPS was prepared in THP1 media and transferred to the first 11 columns of a 96-well polypropylene plate. Column 12 contained only THP1 media for the LO control. Compounds were dissolved in 100% DMSO and serially diluted 3 fold in a polypropylene 96-well microtiter plate (drug plate). Columns 6 and 12 were reserved as controls (HI controls and LO controls respectively) and contained only DMSO. 10 µL of LPS followed by one microliter of inhibitor compound from the drug plate was transferred to the cell plate. The treated cells were induced to synthesize and secrete TNF-α in a 37° C. humidified incubator with 5% $CO_2$ for 3 hours. Fifty microliters of conditioned media was transferred to a 96-well MULTI-ARRAY™ 96-well small spot plate—custom coated with MAB610 containing 100 µL of 2× Read Buffer P supplemented with 0.34 nM AF210NA polyclonal Ab labeled with ruthenium (MSD-Sulfo-TAG™-NHS ester). After an overnight incubation at room temperature with shaking, the reaction was read on the Sector Imager™ 6000. A low voltage was applied to the ruthenylated TNF-α immune complexes, which in the presence of TPA (the active component in the ECL reaction buffer, Read Buffer P), resulted in a cyclical redox reaction generating light at 620 nm. The amount of secreted TNF-α in the presence of AMG compounds compared with that in the presence of DMSO vehicle alone (HI control) was calculated using the formula: % control (POC)=(cpd−average LO)/(average HI−averageLO)*100. Data (consisting of POC and inhibitor concentration in µM) was fitted to a 4-parameter equation (y=A+((B−A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm. The compounds of Examples 1-3, 6-32, 34-37, 39, 41-42, 44-46, 48 and 51-53 exhibited activities in the THP-1 cellular TNF production assay with $IC_{50}$ values of 175 nM or less. A majority of these exemplary compounds exhibited $IC_{50}$ values of 50 nM or less.

Inhibition of TNF-α Induced IL-8 in 50% Human Whole Blood

Test compounds were evaluated in vitro for the ability to inhibit the production of secreted IL-8 by whole blood activated with TNF-α. Fresh human whole blood was obtained from healthy, non-medicated volunteers in sodium heparin tubes.

Compound Dilution—Assay Procedure

Test compounds are serially diluted 1:3 in DMSO and then diluted 1:250 into R10 (RPMI 1640, 10% human serum AB;

1×pen/strep/glutamine) to the 4× working concentration to be used in the assay. 100 ul heparinized whole blood is plated into wells of 96 well flat bottom plates. 50 ul of either 4× compound or DMSO control (Final DMSO concentration is 0.1%) are added to the appropriate wells. Plates are incubated for 1 hour at 37 degrees Celsius. 50 ul of 4×TNF-α (4 mM TNF-α, for a final concentration of 1 nM) or control (media alone) is added to the appropriate wells (Total volume=200 ul). Plates are incubated overnight (16-18 hours). 100 ul of supernatant is collected and stored in 96-well round bottom polypropylene plates at −80 degrees Celsius or assayed immediately for IL-8.

Cytokine Measurement

Cytokines are measured on antibody (Ab) sandwich ECL based 96-well detection plates. 20 ul of supernatant are added to plate and plate is sealed and shaken at RT for 1 hour. 130 ul of detection Ab cocktail is added and plates are sealed and shaken for 1 hour in the dark at RT. Plates are read on MSD Sector HTS instrument. Data are analyzed and $IC_{50}$ values generated using Activity Base and XI-fit programs. Data for exemplary compounds in the human p38-alpha enzyme assay is provided in Tables 1 and 2. Examples 1-3, 6-32, 34-35, 39, 44, 46 and 52-53 exhibited $IC_{50}$ values of less than or equal to 100 nM.

Inhibition of LPS-Induced TNF-α Production Rats

LPS was diluted in PBS (100 μg per rat). Rats (n=6) were pretreated with vehicle or compound (0.03, 0.1, 0.3 and 1.0 mg/kg, PO) 60 minutes prior to the injection of LPS (100 μg per rat/IV, tail vein). Blood was harvested via decapitation 90 minutes following the administration of LPS. Blood was centrifuged at 12,000 rpm for 12 minutes to obtain plasma. Plasma samples were stored at −80° C. TNF-α levels were determined by ELISA for treatment groups that received LPS. Rat TNF-α levels were analyzed using rat TNF-α CytoSet kit from Biosource International. ELISA was completed according to the manufacturer's instructions. The concentration of TNF-α was interpolated from absorbance using the standard curve generated. For each individual sample, the TNF value from the dilution series that fell in the most linear portion of the standard curve was chosen and used for data analysis. The limit of quantitation of the ELISA was 1,000 pg/mL.

Compounds of the invention may be shown to have anti-inflammatory properties in animal models of inflammation, including carageenan paw edema, collagen induced arthritis and adjuvant arthritis, such as the carageenan paw edema model (C. A. Winter et al., Proc. Soc. Exp. Biol. Med., 111: 544 (1962); K. F. Swingle, in R. A. Scherrer and M. W. Whitehouse, Eds., Anti-inflammatory Agents, Chemistry and Pharmacology, 13(II):33, Academic, New York (1974) and collagen induced arthritis (D. E. Trentham et al., J. Exp. Med., 146:857 (1977); J. S. Courtenay, Nature (New Biol.), 283:666 (1980)).

Collagen-Induced Arthritis (CIA) Model in Rats

Porcine type II collagen (10 mg) was dissolved in 0.1N acetic acid (5 mL) two days prior to use on a rotating plate in the refrigerator. Subsequently, collagen was emulsified 1:1 with Freund's incomplete adjuvant using an emulsification needle and glass syringes yielding a final concentration of 1 mg/mL.

Disease was induced in each animal by intradermal injection of emulsified collagen in IFA at 10 different sites (100 μL per site) over the back. The clinical onset of arthritis varied between days 10 to 12 as indicated by hind paw swelling and ambulatory difficulties. At onset (defined as Day 0), rats were randomized to treatment groups and therapy was initiated with drug or vehicle control as noted in table above. Rats were treated for 7 days and were sacrificed on Day 8. Paw swelling and other measurements of efficacy is described Schett et al (Schett et al. Arthritis and Rheum. 52:1604 (2005). Compound examples 7, 13, 20 and 44 exhibited $ED_{50}$'s of 0.01, 0.02, 0.1 and 0.07 mg/kg, respectively, in the rat CIA model.

Cyclooxygenase Enzyme Activity Assay

The human monocytic leukemia cell line, THP-1, differentiated by exposure to phorbol esters expresses only COX-1; the human osteosarcoma cell line 143B expresses predominantly-COX-2. THP-1 cells are routinely cultured in RPMI complete media supplemented with 10% FBS and human osteosarcoma cells (HOSC) are cultured in minimal essential media supplemented with 10% fetal bovine serum (MEM-10% FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 h on a shaker to prevent attachment. Cells are pelleted and resuspended in Hank's Buffered Saline (HBS) at a concentration of $2.5 \times 10^6$ cells/mL and plated in 96-well culture plates at a density of $5 \times 10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-1b/mL, plated in 96-well tissue culture plates at a density of $3 \times 10^4$ cells per well, incubated on a shaker for 1 hour to evenly distribute cells, followed by an additional 2 hour static incubation to allow attachment. The media is then replaced with MEM containing 2% FBS (MEM-2% FBS) and 1 ng human IL-1b/mL, and the cells incubated for 18-22 h. Following replacement of media with 190 mL MEM, 10 mL of test compound diluted in HBS is added to achieve the desired concentration and the cells incubated for 4 h. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls. Various compounds of the invention may be shown to inhibit the COX-1 and/or COX-2 activity.

Indications

Accordingly, compounds of the invention are useful for, but not limited to, the prevention or treatment of inflammation, pro-inflammatory cytokines levels including, without limitation, TNF, IL-1, IL-2, IL-6 and/or IL-8, and disease associated therewith. The compounds of the invention have p38 kinase modulatory activity. In one embodiment of the invention, there is provided a method of treating a disorder related to the activity of p38 enzyme in a subject, the method comprising administering to the subject an effective dosage amount of a compound of a compound of Formulas I, I-B or I-C.

Accordingly, the compounds of the invention would be useful in therapy as anti-inflammatory agents in treating inflammation, or to minimize deleterious effects of p38. Based on the ability to modulate pro-inflammatory cytokine production, the compounds of the invention are also useful in treatment and therapy of cytokine-mediated diseases.

Particularly, these compounds can be used for the treatment of rheumatoid arthritis, Pagets disease, osteoporosis, multiple myeloma, uveitis, acute or chronic myelogenous leukemia, pancreatic β cell destruction, osteoarthritis, rheumatoid spondylitis, gouty arthritis, inflammatory bowel disease, adult restpiratory distress syndrome (ARDS psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection, or any combination thereof, in a subject.

An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further applicable to the treatment of inflammation, e.g. inflammatory disease or condition, of connective tissues including dermatomyositis and myositis.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration.

The compounds of the invention are also useful in the treatment of diabetic conditions such as diabetic retinopathy and microangiopathy.

The compounds of the present invention are also useful for treating ankylosing spondylitis, inflammatory bowel disease, inflammatory pain, ulcerative colitis, Crohn's disease, asthma, chronic obstructive pulmonary disease, myelodysplastic syndrome, endotoxic shock, chronic hepatitis C or a combination thereof.

Thus, the present invention provides methods for the treatment of p38 protein kinase-associated disorders, comprising the step of administering to a subject, including human subjects, prophylactically or therapeutically, at least one compound of the Formula I or of Formula II in an amount effective therefore. Other therapeutic agents such as those described below may be employed with the inventive compounds in the present methods. In the methods of the present invention, such other therapeutic agent(s) may be administered prior to, simultaneously with or following the administration of the compound(s) of the present invention. The present invention also provides for a method for treating atopic dermatitis by administration of a therapeutically effective amount of a compound of the present invention to a patient, whether or not in need of such treatment.

In yet another embodiment, the compounds are useful for decreasing the level of, or lowering plasma concentrations of one or more of TNF-α, IL-1β, IL-6 and IL-8 in a subject, including human subjects, generally a mammal and typically a human.

In yet another embodiment, the compounds are useful for treating a pain disorder in a subject, including human subjects, by administering to the subject an effective dosage amount of a compound according to formulas I, I-B or I-C.

In yet another embodiment, the compounds are useful for treating diabetes in a subject, including human subjects, by administering to the subject an effective dosage amount of a compound according to formulas I, I-B or I-C, to produce a glucagon antagonist effect.

In yet another embodiment, the compounds are useful for decreasing prostaglandin production in a subject, including human subjects, by administering to the subject an effective dosage amount of a compound according to formulas I, I-B or I-C.

In yet another embodiment, the compounds are useful for decreasing cyclooxygenase enzyme activity in a subject, including human subjects, by administering to the subject an effective amount of a compound according to formulas I, I-B or I-C.

In yet another embodiment, the cyclooxygenase enzyme is COX-2.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating TNF-α, IL-1, IL-6, and IL-8 mediated diseases, cancer, and/or hyperglycemia with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.001 mg/kg to 500 mg/kg, advantageously between about 0.005 and about 50 mg/kg, more advantageously about 0.005 and about 30 mg/kg, even more advantageously between about 0.005 and about 10 mg/kg, and even more advantageously about 0.01 and about 5 mg/kg, and should be useful for all methods of use disclosed herein. The daily dose can be administered in one to four doses per day.

While it may be possible to administer a compound alone, the compound of Formulas I, I-B or I-C is normally administered as an active pharmaceutical ingredient (API) in a composition comprising other suitable and pharmaceutically acceptable excipients. This admixture is typically referred to as a pharmaceutical composition. This composition should be pharmaceutically acceptable. In another embodiment, the invention provides a pharmaceutical composition comprising a compound of the present invention in combination with a pharmaceutically acceptable excipient. Pharmaceutical excipients generally include diluents, carriers, adjuvants and the like (collectively referred to herein as "excipient" materials) as described herein, and, if desired, other active ingredients. A pharmaceutical composition of the invention may comprise an effective amount of a compound of the invention or an effective dosage amount of a compound of the invention. An effective amount of the compound is typically that amount capable of bring about a desired physiological effect in the subject. An effective dosage amount of a compound of the invention may constitute administering to the subject one or more than one individual dosage units of the pharmaceutically acceptable composition comprising said compound. For example, where two or more unit dosages of a pharmaceutical composition, such as a tablet, pill, capsule, liquid, suspension and the like, may be required to administer an effective amount of the compound, then the effective dosage amount of the API is less than the effective amount of the API. Thus, an effective dosage amount may include an amount less than, equal to or greater than an effective amount of the compound. A suitable pharmaceutically acceptable composition, such as a powder, a liquid and the like, may exist in which the effective amount of the compound is administered by administering a portion of the composition and requiring the subject to take multiple doses over a specified period of time.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of API from about 1 to 2000 mg, advantageously from about 1 to 500 mg, and typically from about 5 to 150 mg.

A suitable daily dose for a human or other mammal may vary widely depending on the condition of the patient and other factors, but, once again, can be determined using routine methods and practices.

For therapeutic purposes, the compounds of this invention are ordinarily combined with one or more adjuvants or "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the APIs may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene-glycol, propylene glycol, ethanol, cormoil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The API may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment, the present invention provides the use of a medicament for the treatment of inflammatory conditions, including RA, psoriasis, psoriatic arthritis, pain, COPD, Crohns disease, and other indications described herein.

In yet another embodiment, there is provided a method of manufacturing a medicament for the treatment of inflammation, the method comprising combining an amount of a compound according to Formulas I, I-B or I-C with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of TNF-$\alpha$, IL-1, IL-6, and IL-8 mediated diseases, cancer, and/or hyperglycemia.

If formulated as a fixed dose, such combination products employ the compounds of this invention within the accepted dosage ranges. Compounds of Formulas I, I-B or I-C may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The compounds of the invention may also be used in co-therapies with anti-neoplastic agents such as other kinase inhibitors, including CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing descrip-

What is claimed is:

1. A compound of Formula I:

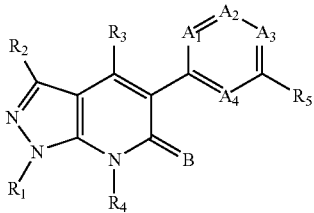

I or a pharmaceutically acceptable salt thereof, wherein
each of $A^1$, $A^2$, $A^3$ and $A^4$, independently, is $CR^6$ or N, provided that no more than two of $A^1$, $A^2$, $A^3$ and $A^4$ is N;
B is O, S or N—CN;
$R^1$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$,
or $R^1$ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^9$;
each of $R^2$ and $R^3$, independently, is H, halo, haloalkyl, $NO_2$, CN, $OR^7$, $SR^7$, $NR^7R^7$, $NR^7R^8$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$;
$R^4$ is CN, $C(O)R^7$, $C_{1-10}$-alkyl, $C_{2-10}$-alkenyl, $C_{2-10}$-alkynyl or $C_{3-8}$-cycloalkyl, each of the $C_{1-10}$-alkyl, $C_{2-10}$-alkenyl, $C_{2-10}$-alkynyl and $C_{3-8}$-cycloalkyl optionally comprising 1-4 heteroatoms selected from N, O and S and optionally substituted with one or more substituents of $R^9$;
$R^5$ is $NR^7R^7$, $NR^7R^8$, $C(O)R^7$, $C(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $NR^7(COOR^7)$, $NR^7(COOR^8)$, $S(O)_2R^7$, $S(O)_2R^8$, $S(O)_2NR^7R^7$, $S(O)_2NR^7R^8$, $NR^7S(O)_2NR^7R^8$, $NR^7S(O)_2R^7$ or $NR^7S(O)_2R^8$;
each $R^6$, independently, is H, halo, haloalkyl, $NO_2$, CN, $OR^7$, $NR^7R^7$ or $C_{1-10}$-alkyl, the $C_{1-10}$-alkyl optionally comprising 1-4 heteroatoms selected from N, O and S and optionally substituted with one or more substituents of $R^9$;
each $R^7$, independently, is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;
$R^8$ is a partially or fully saturated or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;
alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-5 substituents of $R^9$; and
$R^9$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

2. The compound of claim 1, or a pharmaceutically acceptable salt thereof, wherein one of $A^1$, $A^2$, $A^3$ and $A^4$, independently, is N and the remaining of $A^1$, $A^2$, $A^3$ and $A^4$, independently, is $CR^6$ wherein each $R^6$, independently, is H, F, Cl, Br, $CF_3$, —$OCF_3$, $C_2F_5$, —$OC_2F_5$, —O—$C_{1-6}$-alkyl, —$C_{1-4}$-alkyl-O—$C_{1-6}$-alkyl, —S—$C_{1-6}$-alkyl, —$C_{1-4}$-alkyl-S—$C_{1-6}$-alkyl, —NH—$C_{1-6}$-alkyl, —N($C_{1-6}$-alkyl)$_2$, —$C_{1-4}$-alkyl-NH—$C_{1-6}$-alkyl, —$C_{1-3}$-alkyl-N($C_{1-4}$-alkyl)$_2$, $NO_2$, $NH_2$, CN, $C_{1-10}$-alkyl, the $C_{1-10}$-alkyl optionally substituted with one or more substituents of $R^9$.

3. The compound of claim 1, or a pharmaceutically acceptable salt thereof,
wherein each of $A^1$, $A^2$, $A^3$ and $A^4$, independently, is $CR^6$ wherein each $R^6$, independently, is H, F, Cl, Br, $CF_3$, —$OCF_3$, $C_2F_5$, —$OC_2F_5$, —O—$C_{1-6}$-alkyl, —$C_{1-4}$-alkyl-O—$C_{1-6}$-alkyl, —S—$C_{1-6}$-alkyl, —$C_{1-4}$-alkyl- S—$C_{1-6}$-alkyl, —NH—$C_{1-6}$-alkyl, —N($C_{1-6}$-alkyl)$_2$, —$C_{1-4}$-alkyl-NH—$C_{1-6}$-alkyl, —$C_{1-3}$-alkyl-N($C_{1-4}$-alkyl)$_2$, NO$_2$, NH$_2$, CN, $C_{1-10}$alkyl, the $C_{1-10}$alkyl optionally substituted with one or more substituents of R$^9$; and each of R$^2$ and A$^3$, independently, is H or halo.

4. The compound of claim 3, or a pharmaceutically acceptable salt thereof, wherein R$^1$ is $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of R$^9$.

5. The compound of claim 3, or a pharmaceutically acceptable salt thereof, wherein R$^1$ is phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, tetrahydrofuryl, pyrrolyl, tetrahydropyrrolyl, pyrazolyl, imidazolyl, triazolyl, tetrazolyl, thiazolyl, oxazolyl, oxazolinyl, isoxazolyl, isoxazolinyl, oxadiazolyl, isothiazolyl, indolyl, indolinyl, isoindolyl, benzofuranyl, dihydrobenzofuranyl, benzothiophenyl, benzisoxazolyl, benzopyrazolyl, benzothiazolyl, benzimidazolyl, piperidinyl, pyranyl, cyclopropyl, cyclobutyl or cyclorhexyl, each of which is optionally substituted as defined in claim 1.

6. The compound of claim 1, or a pharmaceutically acceptable salt thereof, wherein each of R$^2$ and R$^3$, independently, is H, halo, haloalkyl, NO$_2$, CN, OR$^7$, NR$^7$R$^7$ or $C_{1-10}$-alkyl.

7. The compound of claim 1, or a pharmaceutically acceptable salt thereof, wherein R$^4$ is CN, C(O)R$^7$, $C_{1-4}$-alkylC(O)R$^7$, methyl, ethyl, propyl, isopropyl, cyclopropyl, butyl, isobutyl, tert-butyl, pentyl, neopentyl or $C_{1-4}$-alkyl-amino-$C_{1-4}$-alkyl or $C_{1-10}$-dialkylamino$C_{1-4}$-alkyl-.

8. The compound of claim 1, or a pharmaceutically acceptable salt thereof, wherein R$^8$ is a ring selected from phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring is optionally substituted independently with 1-3 substituents of R$^9$.

9. The compound of claim 1, or a pharmaceutically acceptable salt thereof, wherein B is O;

R$^l$ is phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, tetrahydrofuryl, pyrrolyl, tetrahydropyrrolyl, pyrazolyl, imidazolyl, triazolyl, tetrazolyl, thiazolyl, oxazolyl, oxazolinyl, isoxazolyl, isoxazolinyl, oxadiazolyl, isothiazolyl, indolyl, indolinyl, isoindolyl, benzofuranyl, dihydrobenzofuranyl, benzothiophenyl, benzisoxazolyl, benzopyrazolyl, benzothiazolyl, benzimidazolyl, piperidinyl, pyranyl, cyclopropyl, cyclobutyl or cyclohexyl, each of which is optionally substituted independently with 1-3 substituents of R$^9$;

each of R$^2$ and R$^3$, independently, is H, halo, haloalkyl or $C_{1-10}$-alkyl;

R$^4$ is CN, C(O)R$^7$, $C_{1-4}$-alkylC(O)R$^7$, methyl, ethyl, propyl, isopropyl, cyclopropyl, butyl, isobutyl, tert-butyl, pentyl, neopentyl or $C_{1-4}$-alkyl-amino-$C_{1-4}$-alkyl or $C_{1-10}$-dialkylamino$C_{1-4}$-alkyl-;

R$^5$ is NR$^7$R$^7$, NR$^7$R$^8$, C(O)NR$^7$R$^7$, C(O)NR$^7$R$^8$, NR$^7$C(O)R$^7$, NR$^7$C(O)R$^8$, NR$^7$C(O)NR$^7$R$^7$, NR$^7$C(O)NR$^7$R$^8$, NR$^7$(COOR$^7$), NR$^7$(COOR$^8$), S(O)$_2$R$^7$, S(O)$_2$R$^8$, S(O)$_2$NR$^7$R$^7$, S(O)$_2$NR$^7$R$^8$, NR$^7$S(O)$_2$NR$^7$R$^8$, NR$^7$S(O)$_2$R$^7$ or NR$^7$S(O)$_2$R$^8$;

each R$^6$, independently, is H, F, Cl, Br, CF$_3$, —OCF$_3$, C$_2$F$_5$, —OC$_2$F$_5$, —O—$C_{1-6}$-alkyl, —$C_{1-4}$-alkyl-O—$C_{1-6}$-alkyl, —S—$C_{1-6}$-alkyl, —$C_{1-4}$-alkyl-S—$C_{1-6}$-alkyl, —NH—$C_{1-6}$-alkyl, —N($C_{1-6}$-alkyl)$_2$, —$C_{1-4}$-alkyl-NH—$C_{1-6}$-alkyl, —$C_{1-3}$-alkyl-N($C_{1-4}$-alkyl)$_2$, NO$_2$, NH$_2$, CN or $C_{1-10}$-alkyl, the $C_{1-10}$-alkyl optionally substituted with one or more substituents of R$^9$;

each R$^7$, independently, is H, $C_{1-10}$-alkyl or $C_{3-10}$-cycloalkyl, wherein the $C_{1-10}$-alkyl and $C_{3-10}$-cycloalkyl optionally comprising 1-4 heteroatoms selected from N, O and S and optionally substituted with 1-3 substituents of R$^9$;

R$^8$ is a ring selected from phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring is optionally substituted independently with 1-3 substituents of R$^9$; and R$^9$ is H, halo, haloalkyl, CN, OH, NO$_2$, NH$_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

10. The compound of claim 1, or a pharmaceutically acceptable salt thereof, selected from:

N-cyclopropyl-3-(7-ethyl-1-(2-fluorophenyl)-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-4-methylbenzamide;

3-(1-(2-chlorophenyl)-7-methyl-6-oxo-6,7-dihydro-1H-pyrazolo[3,4-b]pyridin-5-yl)-N-cyclopropyl-5-fluoro-4-methylbenzamide;

N-cyclopropyl-3-(7-ethyl-1-(2-fluorophenyl)-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-4-methylbenzamide;

3-(1-(2-chlorophenyl)-7-methyl-6-oxo-6,7-dihydro-1H-pyrazolo[3,4-b]pyridin-5-yl)-N-cyclopropyl-5-fluoro-4-methylbenzamide;

N-cyclopropyl-3-(7-ethyl-1-(2-fluorophenyl)-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-5-fluoro-4-methylbenzamide;

N-cyclopropyl-3-(1-(2,6-difluorophenyl)-7-methyl-6-oxo-6,7-dihydro-1H-pyrazolo[3,4-b]pyridin-5-yl)-4-methylbenzamide;

3-(1-(2-chlorophenyl)-7-methyl-6-oxo-6,7-dihydro-1H-pyrazolo[3,4-b]pyridin-5-yl)-N-cyclopropyl-5-fluoro-4-methylbenzamide;

11. A pharmaceutical composition comprising a compound according to claim 1 and a pharmaceutically acceptable excipient.

12. A pharmaceutical composition comprising a compound according to claim 10 and a pharmaceutically acceptable excipient.

13. A method of preparing a compound according to claim 1, the method comprising the step of reacting a compound 7

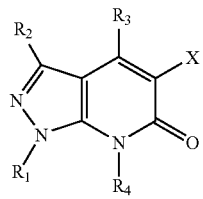

, wherein $R^1$, $R^2$, $R^3$ and $R^4$ are as defined in claim 1 and X is a halogen, with a boronic acid having a general formula

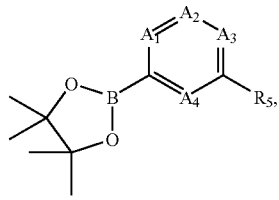

wherein $A^1$, $A^2$, $A^3$, $A^4$ and $R^5$ is as defined in claim 1, to make a compound of claim 1.

14. The compound of claim 9, or a pharmaceutically acceptable salt thereof, wherein each of $A^1$ and $A^2$, independently, is $CR^6$ wherein each $R^6$, independently, is H, F, Cl, Br, $CF_3$, —$OCF_3$, $C_2F_5$, —$OC_2F_5$, —O—$C_{1-4}$-alkyl, —S—$C_{1-4}$-alkyl, —NH—$C_{1-4}$-alkyl, OH, $NO_2$, $NH_2$, CN, methyl, ethyl or propyl;

each of $A^3$ and $A^4$, independently, is CH;

$R^1$ is phenyl or pyridyl, each of which is optionally substituted independently with 1-3 substituents of $R^9$;

each of $R^2$ and $R^3$, independently, is H, F, Cl, methyl or ethyl;

$R^4$ is methyl, ethyl, propyl, isopropyl, cyclopropyl, butyl, isobutyl, tert-butyl, pentyl or neopentyl;

$R^5$ is $C(O)NR^7R^7$, $C(O)NR^7R^8$, $NR^7C(O)R^7$ or $NR^7C(O)R^8$;

each $R^7$, independently, is H, $C_{1-10}$-alkyl or $C_{3-10}$-cycloalkyl, wherein the $C_{1-10}$-alkyl and $C_{3-10}$- cycloalkyl optionally comprising 1-4 heteroatoms selected from N, O and S and optionally substituted with 1-3 substituents of $R^9$;

$R^8$ is a ring selected from phenyl, naphthyl, pyridyl, pyrimidyl, triazinyl, pyridazinyl, pyrazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring is optionally substituted independently with 1-3 substituents of $R^9$; and $R^9$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

15. The compound of claim 14, of a pharmaceutically acceptable salt thereof, wherein $R^8$ is cyclopropyl optionally substituted independently with 1-3 substituents of $R^9$.

16. The compound of claim 1, or a pharmaceutically acceptable salt thereof, that is N-cyclopropyl-3-(1-(2,4-difluorophenyl)-7-methyl-6-oxo-6,7-dihydro-1H-pyrazolo[3,4-b]pyridin-5-yl)-4-methylbenzamide, having a chemical structure of

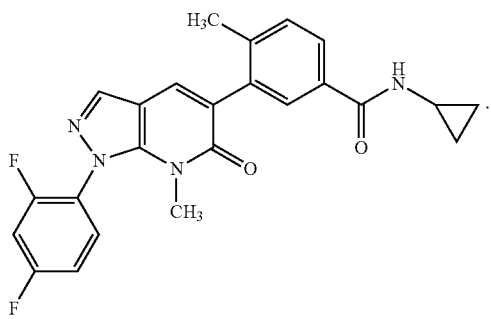
17. The compound of claim 16 that is N-cyclopropyl-3-(1-(2,4-difluorophenyl)-7-methyl-6-oxo-6,7-dihydro-1H-pyrazolo[3,4-b]pyridin-5-yl)-4-methylbenzamide, having a chemical structure of
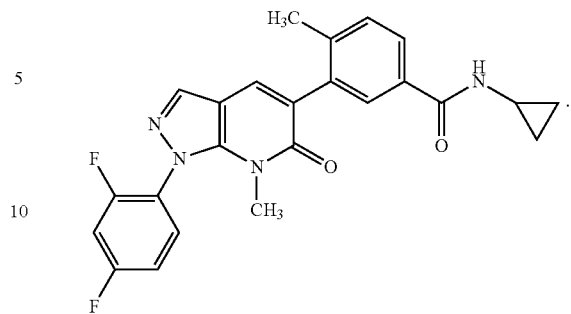
18. A pharmaceutical compositon comprising the compound or a pharmaceutically acceptable salt thereof according to claim 16 and a pharmaceutically acceptable excipient.
* * * * *